US009994626B2

(12) United States Patent
Nilsson et al.

(10) Patent No.: US 9,994,626 B2
(45) Date of Patent: Jun. 12, 2018

(54) STABLE POLYPEPTIDES BINDING TO HUMAN COMPLEMENT C5

(71) Applicant: Swedish Orphan Biovitrum AB (publ), Stockholm (SE)

(72) Inventors: Joakim Nilsson, Danderyd (SE); Erik Nordling, Danderyd (SE); Patrik Strömberg, Sollentuna (SE)

(73) Assignee: Swedish Orphan Biovitrum AB (publ), Stockholm (SE)

( * ) Notice: Subject to any disclaimer, the term of this patent is extended or adjusted under 35 U.S.C. 154(b) by 0 days. days.

(21) Appl. No.: 14/914,290

(22) PCT Filed: Aug. 28, 2014

(86) PCT No.: PCT/EP2014/068282
§ 371 (c)(1),
(2) Date: Feb. 25, 2016

(87) PCT Pub. No.: WO2015/028558
PCT Pub. Date: Mar. 5, 2015

(65) Prior Publication Data
US 2016/0311870 A1 Oct. 27, 2016

(30) Foreign Application Priority Data

Aug. 28, 2013 (SE) ...................................... 1350986

(51) Int. Cl.
*A61K 38/00* (2006.01)
*C07K 14/47* (2006.01)
*C07K 14/315* (2006.01)

(52) U.S. Cl.
CPC ............ *C07K 14/47* (2013.01); *C07K 14/315* (2013.01); *A61K 38/00* (2013.01)

(58) Field of Classification Search
None
See application file for complete search history.

(56) References Cited

U.S. PATENT DOCUMENTS

| 9,187,535 | B2 | 11/2015 | Lindborg et al. |
| 2005/0090448 | A1 | 4/2005 | Johnson et al. |
| 2014/0140366 | A1 | 5/2014 | Tamatani et al. |
| 2015/0011474 | A1 | 1/2015 | Berghard et al. |
| 2016/0200772 | A1 | 7/2016 | Nording et al. |

FOREIGN PATENT DOCUMENTS

| WO | 9101743 A1 | 2/1991 |
| WO | 9529697 A1 | 11/1995 |
| WO | 0230985 A2 | 4/2002 |
| WO | 02059148 A2 | 8/2002 |
| WO | WO 02/059148 | * 8/2002 |
| WO | 03015819 A1 | 2/2003 |
| WO | 2004007553 A1 | 1/2004 |
| WO | 2005023866 A2 | 3/2005 |
| WO | 2005075507 | 8/2005 |
| WO | 2007028968 A1 | 3/2007 |
| WO | 2007106585 A1 | 9/2007 |
| WO | 2009016043 A2 | 2/2009 |
| WO | 2009077175 A1 | 6/2009 |
| WO | 2009080810 A1 | 7/2009 |
| WO | 2010015608 A1 | 2/2010 |
| WO | 2011063980 A1 | 6/2011 |
| WO | 2012004384 A2 | 1/2012 |
| WO | 2013126006 A1 | 8/2013 |
| WO | 2014096163 A1 | 6/2014 |

OTHER PUBLICATIONS

NCBI Reference Sequence NP_001726-2, download on Mar. 17, 2017 from URL <https://www.ncbi.nlm.nih.gov/protein/NP_001726.2>.*
GenBank CPA33816.1, downloaded on Jun. 12, 2017 from URL:<https://www.ncbi.nlm.nih.gov/protein/CPA33816.1>.*
Kraulis et al., FEBS Letters 378 (1996) 190 194 (Year: 1996).*
"Mutant Streptococcus G148 ABD/SPA Z domain fusion protein"; XP002731913; retreived from EBI accession No. GSP: AAB01886.
International Preliminary Report on Patentability for International Application No. PCT/EP2014/068259; International Filing Date Aug. 28, 2014; dated Mar. 10, 2016; 5 pages.
International Search Report for International Application No. PCT/EP2014/068259; International Filing Date Aug. 28, 2014; dated Nov. 18, 2014; 4 pages.
International Search Report for the International Searching Authority for International Patent Application No. PCT/SE2013/050139; International Filing Date: Feb. 19, 2013; dated May 28, 2013; 6 Pages.
Larghi et al., "Modulatiors of Complement Activation: A Patent Review", Expert Opinion on Therapeutic Patents; vol. 24; No. 6; Jun. 1, 2014; pp. 665-686.
Supplementary European Search Report of the European Searching Authority for European Patent Application No. 13752233.0; dated Aug. 5, 2015; 10 Pages.
Written Opinion for International Application No. PCT/EP2014/068259; International Filing Date Aug. 28, 2014; dated Nov. 18, 2014; 4 pages.

(Continued)

*Primary Examiner* — Jennifer Pitrak McDonald
*Assistant Examiner* — Sergio Coffa
(74) *Attorney, Agent, or Firm* — Wolf, Greenfield & Sacks, P.C.

(57) ABSTRACT

The invention relates to a polypeptide capable of binding human complement component 5 (C5), said polypeptide comprising the amino acid sequence (SEQ ID NO: 296)
[BM]-[L2]-QSX$_{42}$X$_{43}$LLX$_{46}$EAKKLX$_{52}$X$_{53}$X$_{54}$Q wherein [BM] is a C5 binding motif; [L2] is an interconnecting loop; X$_{42}$ is selected from A and S; X$_{43}$ is selected from N and E; X$_{46}$ is selected from A, S and C; X$_{52}$ is selected from E, N and S; X$_{53}$ is selected from D, E and S, provided that X$_{53}$ is not D when X$_{52}$ is N; and X$_{54}$ is selected from A and S.

14 Claims, 19 Drawing Sheets

(56) References Cited

OTHER PUBLICATIONS

Written Opinion of the International Searching Authority for International Patent Application No. PCT/SE2013/050139; International Filing Date: Feb. 19, 2013; dated May 28, 2013; 5 Pages.
International Preliminary Report on Patentability for International Application No. PCT/EP2014/068282; International Filing Date Aug. 28, 2014; dated Nov. 5, 2015; 10 pages.
International Search Report and Written Opinion of the International Searching Authority for International Application No. PCT/EP2014/068282; International Filing Date Aug. 28, 2014; dated Jan. 7, 2015; 14 pages.
Stromberg et al., "Development of Affibody C5 Inhibitors for Versatile and Efficient Therapeutic Targeting of the Terminal Complement Pathway", Abstracts/Molecular Immunology; vol. 61; No. 2; Oct. 1, 2014; p. 256.
Written Opinion of the International Preliminary Examining Authority for International Application No. PCT/EP2014/068282; International Filing Date Aug. 28, 2014; dated Jul. 30, 2015; 8 pages.
Frankel et al.; "Characterization of diphtheria fusion proteins targeted to the human interleukin-3 receptor"; Protein Eng., vol. 13, No. 8; 2000; pp. 575-581.
Paukla et al.; Abstract of "Genetic analysiws of protein stability and function"; Annu. Rev. Genet., vol. 23; 1989; 1 page.
A. Lapeyraque et al., "Eculizumab in Severe Shiga-Toxin-Associated HUS," New England Journal of Medicine; Jun. 30, 2011, pp. 2561-2563, vol. 364, No. 26.
A. Manderson et al., "The Role of Complement in the Development of Systemic Lupus Erythematosus," Annual Review of Immunology; 2004, pp. 431-456, vol. 22.
B. Tack et al., "Fifth Component of Human Complement: Purification from Plasma and Polypeptide Chain Structure," American Chemical Society; 1979, pp. 1490-1497, vol. 18, No. 8.
C. Gronwall et al., "Selection and Characterization of Affibody Ligands Binding to Alzheimer Amyloid B Peptides;" Journal of Biotechnology; 2007, pp. 162-183, vol. 128.
D. Copland et al., "Systemic and Local Anti-C5 Therapy Reduces the Disease Severity in Experimental Autoimmune Uveoretinitis," Clinical and Experimental Immunology 2009, pp. 303-314, vol. 159.
D. Haviland et al., "Cellular Expression of the C5a Anaphylatoxin Recepter (C5aR): Demonstration of C5aR on Nonmyeloid Cells of the Liver and Lung," The Journal of Immunology; 1995, pp. 1861-1869, vol. 154.
D. Ricklin et al., "Complement—A Key System for Immune Surveillance and homeostasis," Sep. 2010, pp. 785-797, vol. 11, No. 9.
F. Fredslund et al., "Structure of and Influence of a Tick Complement Inhibitor on Human Complement Component 5," Nature Immunology; Jul. 2008, pp. 753-760, vol. 9., No. 7.
G. Cazander et al., "Complement Activation and Inhibition in Wound Healing," Clincial and Development Immunology; 2012, pp. 1-14, vol. 2012, Article ID: 534291.
J. Howard Jr. et al., "A Randomized, Double-Blind, Placebo-Controlled Phase II Study of Eculizumab in Patients with Refractory Generalized Myasthenia Gravis," Muscle & Nerve; Jul. 2013, pp. 76-84.
K. Kaida et al., "Antibodies to Gangliosides and Ganglioside Complexes in Guillain-Barre Syndrome and Fisher Syndrome: Mini-review," Journal of Neuroimmunology; 2010, pp. 5-12, vol. 223.
M. Chen et al., "The Complement System in Systemic Autoimmune Disease," Journal of Autoimmunity; 2010, pp. J276-J286, vol. 34.
M. Fung et al., "Pre-neutralization of C5a-mediated Effects by the Monoclonal Antibody 137-26 Reacting with the C5a Moiety of Native C5 Without Preventing C5 Cleavage," Clin. Exp Immunol; 2003, pp. 160-169, vol. 133.
M. Markiewski et al., "Modulation of the Anti-tumor Immune Response by Complement," Nature Immunology; Nov. 2008, pp. 1225-1235, vol. 9, No. 11.
M. Nunn, et al., Complement Inhibitor of C5 Activation from the Soft Tick *Ornithodoros moubata*,: The Journal of Immunology; 2005, pp. 2084-2091, vol. 174.
M. Stegall et al., "Terminal Complement Inhibition Decreases Antibody-Mediated Rejection in Sensitized Renal Transplant Recipients," American Journal of Transplantation; 2011, pp. 2405-2413, vol. 11.
S. Pittock et al., "Eculizumab in AQP4-IgG-positive Relapsing Neuromyelitis Optica Spectrum Disorders: An Open-label Pilot Study," Lancet Neurology; Jun. 2013, pp. 554-562, vol. 12.
T. Abe et al., "Local Complement-Targeted Intervention in Periodontitis: Proof-of-Concept Using a C5a Receptor (CD88) Antagonist," The Journal of Immunology; 2012, pp. 5442-5448, vol. 189, No. 11.
T. Woodruff et al., "Inhibiting the C5-C5a Receptor Axis," Molecular Immunology; 2011, pp. 1631-1642, vol. 48.
K. Maida et al., "Antibodies to Gangliosides and Ganglioside Complexes in Guillain-Barre Syndrome and Fisher Syndrome: Mini-review," Journal of Neuroimmunology; 2010, pp. 5-12, vol. 223.
T. Abe et al., "Local Complement-Targeted Intervention in Periodontitis: Proof-of-Concept Using a C5a Receptor (CD88) Antagonist," The Journal of Immunology: 2012, pp. 5442-5448, vol. 189, No. 11.
Unknown [online]; [retrieved on Mar. 17, 2017]; retrieved from the internet https://www.ncbi.nlrn.nih.gov/protein/NP_001726.2.
NCBI. "Complement C5 isoform 1 Preproprotein [*Homo sapiens*]," NCBI Reference Sequence: NP_0017262., Oct. 6, 2016.

\* cited by examiner

| Polypeptide | Amino Acid Sequence | SEQ ID NO: |
|---|---|---|
| CBM06175 | EVLEAWDEIDRLPNLTIEQWLAFINKLDD | 1 |
| CBM08044 | EVLEAWNEIDRLPNLTIEQWLAFINKLDD | 2 |
| CBM05998 | EVIEAWNEIDRLPNLTIEQWLAFINKLDD | 3 |
| CBM06009 | EVLEAWDEIDRLPNLTLDQWLAFINKLDD | 4 |
| CBM06079 | EVLDAWDEIDALPNLTIEQWLAFINKLDD | 5 |
| CBM06126 | EVIDAWDEIDRLPNLTLDQWLAFINKLDD | 6 |
| CBM06140 | ETLEAWDEIDRLPNLTIEQWLAFINKLDD | 7 |
| CBM06189 | EVIDAWNEIDALPNLTLDQWLAFINKLDD | 8 |
| CBM06214 | EVLDAWDEIDKLPNLTIDQWLAFINKLDD | 9 |
| CBM06215 | EVLDAWDEIDHLPNLTLDQWLAFINKLDD | 10 |
| CBM06226 | EVLEAWDEIDALPNLTIEQWLAFINKLDD | 11 |
| CBM06018 | EVLDAWDEIDKLPNLTIEQWLAFINKLDD | 12 |
| CBM05477 | ETITAWDEIDKLPNLTIEQWLAFIGKLED | 13 |
| CBM05363 | ESMKAWDEIDRLPNLNINQWVAFIDSLYD | 14 |
| CBM05483 | ESIEAWTEIDHLPNLTIEQWLAFINKLTD | 15 |
| CBM05538 | EVLDAWHEIDTLPNLTVRQWLAFISKLED | 16 |
| CBM05692 | EHIQANEEIDRLPNLTIKQWLAFINKLHD | 17 |
| CBM05994 | EVLHAWAEIDALPNLTIEQWLAFINKLDD | 18 |
| CBM05995 | EVLAAWDEIDSLPNLTLQQWLAFINKLDD | 19 |
| CBM05996 | EVIDAWNEIDALPNLTIEQWLAFINKLDD | 20 |
| CBM05997 | EVLDAWNEIDALPNLTIDQWLAFINKLSD | 21 |
| CBM05999 | EVLEAWDEIDGLPNLTIEQWLAFINKLDD | 22 |
| CBM06000 | EVLEAWDEIDHLPNLTLQQWLAFINKLDD | 23 |
| CBM06001 | EVIEAWNEIDALPNLTIEQWLAFINKLDD | 24 |

Figure 7A

| | | |
|---|---|---|
| CBM06002 | EVTAAWNEIDRLPNLTLTQWLAFINKLDD | 25 |
| CBM06003 | EVTEAWDEIDALPNLTLTLQQWLAFINKLDD | 26 |
| CBM06004 | EVTAAWDEIDKLPNLTLTEQWLAFINKLDD | 27 |
| CBM06005 | EVTAAWDEIDKLPNLTLQQWLAFINKLDD | 28 |
| CBM06006 | ETTAAWDEIDKLPNLTLTEQWLAFINKLDD | 29 |
| CBM06007 | ETTEAWNEIDRLPNLTLTEQWLAFINKLDD | 30 |
| CBM06008 | EVLEAWREIDALPNLTLTQQWLAFINKLDD | 31 |
| CBM06010 | EVLEAWDEIDQLPNLTLTEQWLAFINKLDD | 32 |
| CBM06011 | EVLRAWDEIDHLPNLTLTEQWLAFINKLDD | 33 |
| CBM06012 | EVLEAWDEIDRLPNLTLNQWLAFINKLDD | 34 |
| CBM06013 | EVLDAWNEIDHLPNLTLTEQWLAFINKLDD | 35 |
| CBM06014 | EVIDAWNEIDKLPNLTLTEQWLAFINKLDD | 36 |
| CBM06015 | ETLEAWDEIDQLPNLTLQQWLAFINKLDD | 37 |
| CBM06016 | EVIEAWNEIDALPNLTLDQWLAFINKLDD | 38 |
| CBM06017 | EVIDAWNEIDRLPNLTLTEQWLAFINKLDD | 39 |
| CBM06019 | EVIDAWNEIDQLPNLTLTEQWLAFINKLDD | 40 |
| CBM06020 | ETTAAWDEIDHLPNLTLTEQWLAFINKLDD | 41 |
| CBM06024 | EVLQAWDEIDHLPNLTIQQWLAFINKLDD | 42 |
| CBM06025 | ETLHAWAEIDRLPNLTLTEQWLAFINKLSD | 43 |
| CBM06026 | EVLEAWNEIDHLPNLTLAQWLAFINKLDD | 44 |
| CBM06027 | EVLEAWDEIDKLPNLTLTIAQWLAFINKLDD | 45 |
| CBM06028 | EVLDAWDEIDHLPNLTLQQWLAFINKLDD | 46 |
| CBM06029 | ETTEAWNEIDKLPNLTLTQWLAFINKLDD | 47 |
| CBM06030 | EVLEAWNEIDLLPNLTLTEQWLAFINKLDD | 48 |
| CBM06031 | EVIEAWDEIDHLPNLTIDQWLAFINKLDD | 49 |
| CBM06032 | EVISAWNEIDALPNLTLQQWLAFINKLDD | 50 |

Figure 7B

| | | |
|---|---|---|
| CBM06033 | EVIAAWNEIDKLPNLTLEQWLAFINKLDD | 51 |
| CBM06034 | ETIEAWNEIDSLPNLTLDQWLAFINKLDD | 52 |
| CBM06035 | EVLDAWNEIDQLPNLTLQQWLAFINKLDD | 53 |
| CBM06037 | EVLAAWNEIDHLPNLTIEQWLAFINKLDD | 54 |
| CBM06038 | EVLEAWDEIDHLPNLTITQWLAFINKLDD | 55 |
| CBM06039 | ETIDAWNEIDHLPNLTIEQWLAFINKLDD | 56 |
| CBM06040 | EVIEAWNEIDHLPNLTIQQWLAFINKLDD | 57 |
| CBM06041 | EVIQAWNEIDALPNLTISQWLAFINKLDD | 58 |
| CBM06043 | EVIAAWDEIDSLPNLTIEQWLAFINKLDD | 59 |
| CBM06044 | EHIEAWNEIDALPNLTLDQWLAFINKLQD | 60 |
| CBM06045 | EVLEAWNEIDHLPNLTLDQWLAFINKLDD | 61 |
| CBM06047 | EVIDAWNEIDHLPNLTIEQWLAFINKLAD | 62 |
| CBM06048 | ETIDAWDEIDKLPNLTIEQWLAFINKLDD | 63 |
| CBM06049 | EVIAAWDEIDLLPNLTLQQWLAFINKLAD | 64 |
| CBM06050 | EVIHAWDEIDKLPNLTIEQWLAFINKLDD | 65 |
| CBM06051 | EVIAAWNEIDHLPNLTLEQWLAFINKLDD | 66 |
| CBM06052 | ETLDAWNEIDKLPNLTLSQWLAFINKLDD | 67 |
| CBM06053 | EVLEAWNEIDALPNLTLEQWLAFINKLDD | 68 |
| CBM06054 | EVIQAWDEIDHLPNLTISQWLAFINKLDD | 69 |
| CBM06055 | EVLQAWDEIDSLPNLTIEQWLAFINKLDD | 70 |
| CBM06056 | ETLEAWDEIDHLPNLTIAQWLAFINKLDD | 71 |
| CBM06057 | ETIDAWNEIDRLPNLTISQWLAFINKLDD | 72 |
| CBM06058 | EVLDAWHEIDHLPNLTIQQWLAFINKLDD | 73 |
| CBM06059 | EQIRAWDEIDKLPNLTIEQWLAFINKLAD | 74 |
| CBM06060 | ETLYAWNEIDKLPNLTIEKLAFIEKLQD | 75 |
| CBM06061 | EVIEAWNEIDALPNLTIDQWLAFINKLDD | 76 |

Figure 7C

| | | |
|---|---|---|
| CBM06062 | EVLEAWNEIDHLPNLTIQQWLAFINKLDD | 77 |
| CBM06063 | ETTEAWDEIDALPNLTIEQWLAFINKLDD | 78 |
| CBM06065 | EVTEAWNEIDHLPNLTIQQWLAFINKLDD | 79 |
| CBM06066 | EVTEAWNEIDKLPNLTIQQWLAFINKLDD | 80 |
| CBM06068 | ETLDAWAEIDHLPNLTLDQWLAFINKLDD | 81 |
| CBM06069 | EHIDAWNEIDALPNLTLSQWLAFINKLDD | 82 |
| CBM06070 | EVLDAWNEIDKLPNLTTAQWLAFINKLDD | 83 |
| CBM06071 | EVTEAWTEIDYLPNLTIQQWLAFINKLDD | 84 |
| CBM06072 | ETTEAWNEIDHLPNLTIAQWLAFINKLDD | 85 |
| CBM06073 | EVIQAWNEIDKLPNLTIEQWLAFINKLDD | 86 |
| CBM06074 | EVTEAWDEIDHLPNLTIEQWLAFINKLDD | 87 |
| CBM06075 | ETIDAWNEIDLLPNLTIEQWLAFINKLDD | 88 |
| CBM06076 | EHIDAWNEIDKLPNLTLDQWLAFINKLDD | 89 |
| CBM06077 | EVVAAWNEIDALPNLTIEQWLAFINKLND | 90 |
| CBM06080 | EVTEAWNEIDALPNLTLAQWLAFINKLDD | 91 |
| CBM06081 | EVLQAWDEIDRLPNLTLDQWLAFINKLDD | 92 |
| CBM06082 | EVIDAWDEIDHLPNLTIEQWLAFINKLSD | 93 |
| CBM06083 | EVVEAWNEIDQLPNLTIEQWLAFINKLDD | 94 |
| CBM06084 | EVIQAWNEIDALPNLTIEQWLAFINKLDD | 95 |
| CBM06085 | EVIQAWDEIDKLPNLTIDQWLAFINKLAD | 96 |
| CBM06086 | EVVAAWDEIDALPNLTLTQWLAFINKLDD | 97 |
| CBM06087 | EVIQAWNEIDGLPNLTLSQWLAFINKLDD | 98 |
| CBM06088 | ETTEAWDEIDALPNLTITQWLAFINKLDD | 99 |
| CBM06089 | EVTDAWNEIDHLPNLTIQQWLAFINKLAD | 100 |
| CBM06090 | ETTEAWNEIDALPNLTLDQWLAFINKLED | 101 |
| CBM06091 | EHIHAWNEIDELPNLTIEQWLAFINKLAD | 102 |

Figure 7D

| | | |
|---|---|---|
| CBM06092 | EVIDAWDEIDHLPNLTIDQWLAFINKLSD | 103 |
| CBM06093 | EVIDANDEIDALPNLTIAQWLAFINKLHD | 104 |
| CBM06095 | ETIEAWDEIDKLPNLTIEQWLAFINKLDD | 105 |
| CBM06097 | EVLLAWDEIDHLPNLTLEQWLAFINKLDD | 106 |
| CBM06098 | EHIDAWNEIDGLPNLTLEQWLAFINKLDD | 107 |
| CBM06099 | EVIEAWSEIDALPNLTIDQWLAFINKLAD | 108 |
| CBM06100 | EQLNAWAEIDALPNLTIEQWLAFINKLDD | 109 |
| CBM06101 | EVIDAWNEIDALPNLTIAQWLAFINKLDD | 110 |
| CBM06103 | ETIDAWNEIDQLPNLTIEQWLAFINKLDD | 111 |
| CBM06104 | EVIEAWDEIDKLPNLTLAQWLAFINKLDD | 112 |
| CBM06105 | EVLYAWAEIDHLPNLTIEQWLAFINKLDD | 113 |
| CBM06107 | EQIDAWNEIDRLPNLTIQQWLAFINKLDD | 114 |
| CBM06108 | EVLAAWDEIDRLPNLTIEQWLAFINKLDD | 115 |
| CBM06109 | EVIEAWDEIDHLPNLTLHQWLAFINKLDD | 116 |
| CBM06110 | EVIEAWNEIDKLPNLTIEQWLAFINKLDD | 117 |
| CBM06111 | EVIDANDEIDALPNLTIEQWLAFINKLHD | 118 |
| CBM06112 | EVIAAWDEIDALPNLTIEQWLAFINKLDD | 119 |
| CBM06113 | EVIEAWTEIDQLPNLTLDQWLAFINKLDD | 120 |
| CBM06114 | EVINAWNEIDALPNLTLQQWLAFINKLDD | 121 |
| CBM06115 | EHIEAWDEIDHLPNLTIDQWLAFINKLAD | 122 |
| CBM06116 | EHLEAWREIDALPNLTIEQWLAFINKLDD | 123 |
| CBM06117 | EVLDAWNEIDKLPNLTLQQWLAFINKLDD | 124 |
| CBM06118 | EVIAAWDEIDHLPNLTIQQWLAFINKLDD | 125 |
| CBM06119 | EVIQAWNEIDALPNLTIEQWLAFINKLDD | 126 |
| CBM06121 | EVIDAWNEIDHLPNLTIAQWLAFINKLDD | 127 |
| CBM06122 | EQLDAWDEIDHLPNLTIDQWLAFINKLSD | 128 |

Figure 7E

| | | |
|---|---|---|
| CBM06123 | EVLNAWDEIDKLPNLTIEQWLAFINKLDD | 129 |
| CBM06124 | EVLEAWNEIDHLPNLTIDQWLAFINKLDD | 130 |
| CBM06125 | EVLLAWDEIDRLPNLTIDQWLAFINKLAD | 131 |
| CBM06127 | EVIAAWNEIDQLPNLTLDQWLAFINKLDD | 132 |
| CBM06128 | ETLLAWDEIDALPNLTIEQWLAFINKLDD | 133 |
| CBM06129 | EVIDAWNEIDTLPNLTLEQWLAFINKLDD | 134 |
| CBM06131 | EVLHAWNEIDHLPNLTLNQWLAFINKLQD | 135 |
| CBM06132 | EVIQAWNEIDALPNLTIAQWLAFINKLDD | 136 |
| CBM06133 | ETVDAWNEIDALPNLTIEQWLAFINKLDD | 137 |
| CBM06134 | EVIQAWDEIDHLPNLTIDQWLAFINKLDD | 138 |
| CBM06135 | EVLDAWNEIDQLPNLTIQQWLAFINKLDD | 139 |
| CBM06136 | ETIEAWNEIDALPNLTLDQWLAFINKLDD | 140 |
| CBM06137 | EVIEAWDEIDALPNLTIDQWLAFINKLDD | 141 |
| CBM06138 | EVIEAWNEIDQLPNLTIQQWLAFINKLDD | 142 |
| CBM06139 | EVIEAWTEIDHLPNLTIEQWLAFINKLDD | 143 |
| CBM06141 | EVIQAWNEIDHLPNLTLQQWLAFINKLED | 144 |
| CBM06142 | EVIQANNEIDQLPNLTIEQWLAFINKLHD | 145 |
| CBM06143 | EVLHAWSEIDKLPNLTIEQWLAFINKLDD | 146 |
| CBM06144 | ETIQAWDEIDKLPNLTLDQWLAFINKLSD | 147 |
| CBM06145 | ETLRAWDEIDKLPNLTIQQWLAFINKLAD | 148 |
| CBM06146 | EVIDAWNEIDHLPNLTIEQWLAFINKLED | 149 |
| CBM06147 | EVIDAWNEIDHLPNLTLQQWLAFINKLAD | 150 |
| CBM06148 | ETIDAWNEIDALPNLTLDQWLAFINKLDD | 151 |
| CBM06149 | EVIEAWNEIDQLPNLTIEQWLAFINKLDD | 152 |
| CBM06150 | EVIRAWDEIDQLPNLTLSQWLAFINKLDD | 153 |
| CBM06151 | EVIEAWNEIDRLPNLTIHQWLAFINKLDD | 154 |

Figure 7F

| | | |
|---|---|---|
| CBM06152 | ETIEAWNEIDQLPNLTIEQWLAFINKLDD | 155 |
| CBM06153 | EVLTAWAEIDALPNLTLSQWLAFINKLDD | 156 |
| CBM06154 | EVIEAWDEIDKLPNLTVDQWLAFINKLDD | 157 |
| CBM06155 | EVIDAWNEIDHLPNLTLTQWLAFINKLDD | 158 |
| CBM06156 | EVIEAWNEIDQLPNLTLDQWLAFINKLDD | 159 |
| CBM06157 | ETLQAWDEIDHLPNLTLNQWLAFINKLDD | 160 |
| CBM06158 | EVIDAWNEIDHLPNLTIEQWLAFINKLDD | 161 |
| CBM06159 | EVIEAWNEIDLLPNLTLSQWLAFINKLDD | 162 |
| CBM06160 | EVIDAWDEIDRLPNLTLKQWLAFINKLDD | 163 |
| CBM06161 | ETLHAWDEIDKLPNLTIEQWLAFINKLDD | 164 |
| CBM06162 | EVIKAWDEIDHLPNLTLNQWLAFINKLDD | 165 |
| CBM06163 | EVIEAWNEIDHLPNLTLAQWLAFINKLDD | 166 |
| CBM06164 | EVIQAWNEIDHLPNLTIDQWLAFITKLED | 167 |
| CBM06165 | EVIEAWNEIDRLPNLTIKQWLAFINKLDD | 168 |
| CBM06167 | EVIEAWNEIDSLPNLTLQQWLAFINKLDD | 169 |
| CBM06168 | ETIDAWNEIDKLPNLTIEQWLAFINKLDD | 170 |
| CBM06169 | EVLEAWAEIDALPNLTIAQWLAFINKLDD | 171 |
| CBM06170 | ETIDAWNEIDRLPNLTIEQWLAFINKLDD | 172 |
| CBM06171 | ETLKAWDEIDRLPNLTLQQWLAFINKLDD | 173 |
| CBM06172 | ETIAAWNEIDALPNLTLQQWLAFINKLDD | 174 |
| CBM06173 | EVLQAWNEIDHLPNLTIQQWLAFINKLDD | 175 |
| CBM06174 | EVIEAWSEIDHLPNLTLQQWLAFINKLDD | 176 |
| CBM06176 | EVIDAWNEIDGLPNLTIEQWLAFINKLDD | 177 |
| CBM06178 | EVIHAWNEIDHLPNLTLNQWLAFINKLED | 178 |
| CBM06179 | EVLDAWNEIDSLPNLTLDQWLAFINKLDD | 179 |
| CBM06180 | EQIEAWNEIDRLPNLTLEQWLAFINKLDD | 180 |

Figure 7G

| | | |
|---|---|---|
| CBM06181 | EVVDAWNEIDALPNLTLQQWLAFINKLDD | 181 |
| CBM06182 | EVIEAWNEIDKLPNLTIEQWLAFINKLDD | 182 |
| CBM06183 | EVIEANDEIDRLPNLTIEQWLAFINKLHD | 183 |
| CBM06184 | ETLQAWDEIDKLPNLTIEQWLAFINKLDD | 184 |
| CBM06185 | EVIEAWDEIDHLPNLTIDQWLAFINKLAD | 185 |
| CBM06186 | ETIDAWNEIDHLPNLTLQQWLAFINKLAD | 186 |
| CBM06187 | EVIDAWDEIDKLPNLTIEQWLAFINKLDD | 187 |
| CBM06188 | EVIEAWNEIDKLPNLTLAQWLAFINKLDD | 188 |
| CBM06190 | EVLQAWDEIDKLPNLTIQQWLAFINKLDD | 189 |
| CBM06191 | EVIAAWNEIDGLPNLTLQQWLAFINKLDD | 190 |
| CBM06192 | ETLNAWNEIDALPNLTLQQWLAFINKLDD | 191 |
| CBM06193 | EVLSAWNEIDQLPNLTLEQWLAFINKLDD | 192 |
| CBM06194 | ETLEAWDEIDHLPNLTLHQWLAFINKLDD | 193 |
| CBM06195 | EQIEAWNEIDHLPNLTLQQWLAFINKLAD | 194 |
| CBM06196 | EVVEAWDEIDKLPNLTIEQWLAFINKLDD | 195 |
| CBM06197 | EVLEAWNEIDELPNLTIEQWLAFINKLDD | 196 |
| CBM06198 | EVIDAWNEIDQLPNLTLQQWLAFINKLDD | 197 |
| CBM06199 | ETIDAWDEIDKLPNLTLSQWLAFINKLDD | 198 |
| CBM06200 | ETIDAWNEIDQLPNLTLQQWLAFINKLDD | 199 |
| CBM06201 | EVIQAWDEIDALPNLTLNQWLAFINKLDD | 200 |
| CBM06202 | EVLDAWAEIDQLPNLTIEQWLAFINKLDD | 201 |
| CBM06203 | EHIAAWDEIDALPNLTIEQWLAFINKLDD | 202 |
| CBM06206 | EVIRAWDEIDALPNLTIEQWLAFINKLDD | 203 |
| CBM06207 | EVIDAWDEIDALPNLTIDQWLAFINKLAD | 204 |
| CBM06208 | EVIDAWNEIDRLPNLTIQQWLAFINKLDD | 205 |
| CBM06209 | EVITAWNEIDHLPNLTLSQWLAFINKLDD | 206 |

Figure 7H

| | | |
|---|---|---|
| CBM06210 | EVIDAWNEIDALPNLTIHQWLAFINKLDD | 207 |
| CBM06211 | EQLKAWDEIDKLPNLTIEQWLAFIEKLQD | 208 |
| CBM06212 | EHIDAWTEIDHLPNLTIEQWLAFINKLDD | 209 |
| CBM06213 | EQLRAWDEIDKLPNLTIEQWLAFINKLQD | 210 |
| CBM06216 | EVLEAWREIDSLPNLTIAQWLAFINKLDD | 211 |
| CBM06217 | EVIQAWNEIDKLPNLTIEQWLAFINKLDD | 212 |
| CBM06218 | EHVEAWNEIDQLPNLTIEQWLAFINKIAD | 213 |
| CBM06219 | EVIDAWDEIDALPNLTIDQWLAFINKLSD | 214 |
| CBM06220 | EVLEAWNEIDHLPNLTIEQWLAFINKLDD | 215 |
| CBM06221 | EVLQAWDEIDKLPNLTIEQWLAFINKLSD | 216 |
| CBM06222 | EVIKAWNEIDSLPNLTIEQWLAFINKLDD | 217 |
| CBM06223 | EVLEAWHEIDLLPNLTIQQWLAFINKLDD | 218 |
| CBM06224 | EVLEAWTEIDRLPNLTLDQWLAFINKLDD | 219 |
| CBM06225 | EQLYAWNEIDHLPNLTIEQWLAFIEKLQD | 220 |
| CBM06227 | EVLNAWDEIDKLPNLTIKQWLAFINKLDD | 221 |
| CBM06228 | EVIRAWDEIDKLPNLTVEQWLAFINKLDD | 222 |
| CBM06230 | EVVQAWDEIDQLPNLTIEQWLAFINKLDD | 223 |
| CBM06231 | EVIRAWDEIDQLPNLTIEQWLAFINKLDD | 224 |
| CBM06232 | ETIDAWNEIDHLPNLTLDQWLAFINKLDD | 225 |
| CBM06233 | EVVAAWTEIDLLPNLTLDQWLAFINKLED | 226 |
| CBM06234 | EVVAAWDEIDALPNLTIEQWLAFINKLSD | 227 |
| CBM06235 | ETLEAWREIDSLPNLTLEQWLAFINKLDD | 228 |
| CBM06236 | EVIKAWNEIDHLPNLTLDQWLAFINKLDD | 229 |
| CBM06237 | EVLEAWTEIDKLPNLTIDQWLAFINKLDD | 230 |
| CBM06238 | ETLEAWDEIDKLPNLTIDQWLAFINKLDD | 231 |
| CBM06239 | EVIEAWNEIDKLPNLTIDQWLAFINKLDD | 232 |

Figure 7I

| | | |
|---|---|---|
| CBM06240 | ETIDAWNEIDKLPNLTLEQWLAFINKLDD | 233 |
| CBM06241 | ETLDAWDEIDALPNLTIDQWLAFINKLED | 234 |
| CBM06242 | EVLSAWNEIDHLPNLTIQQWLAFINKLDD | 235 |
| CBM06244 | EVIQANDEIDKLPNLTIEQWLAFIHKLHD | 236 |
| CBM06245 | EHLDAWDEIDHLPNLTIQQWLAFINKLAD | 237 |
| CBM06246 | EVIQAWNEIDQLPNLTIEQWLAFINKLDD | 238 |
| CBM06247 | EVIEAWNEIDYLPNLTIAQWIAFINKLDD | 239 |
| CBM06248 | ETIQAWDEIDRLPNLTLQQWLAFINKLDD | 240 |
| CBM06249 | ETIQAWDEIDKLPNLTIEQWLAFINKLDD | 241 |
| CBM06250 | ETLDAWAEIDHLPNLTIEQWLAFINKLDD | 242 |
| CBM06251 | EVIEAWDEIDKLPNLTLNQWLAFINKLDD | 243 |
| CBM06252 | EVLDAWNEIDQLPNLTIEQWLAFINKLDD | 244 |
| CBM06253 | EVLHAWNEIDHLPNLTIEQWLAFIEKLED | 245 |
| CBM06254 | EVIEAWQEIDKLPNLTIDQWLAFINKLDD | 246 |
| CBM06257 | EVVDAWNEIDQLPNLTIEQWLAFINKLDD | 247 |
| CBM06258 | EQIEAWNEIDALPNLTIEQWLAFINKLAD | 248 |
| PSI0242 | AEAKYAKEVLEAWDEIDRLPNLTIEQWLAFINKLDDDPSQSSELLSEAKKLNDSQAPKVDGSLAEAKEAANAELDSYGVSDFYKRLIDKAKTV EGVEALKDAILAALP | 249 |
| ABD | LAEAKEAANAELDSYGVSDFYKRLIDKAKTVEGVEALKDAILAALP | 250 |
| Human C5 | MGLLGILCFLIFLGKTWGQEQTYVISAPKIFRVGASENIVIQVYGYTEAFDATISIKSYPDKKFSYSSGHVHLSSENKFQ NSAILTIQPKQLPGGQNPVSYVYLEVVSKHFSKSKRMPITYDNGFLFIHTDKPVTPDQSVKVRVYSLNDDIKPAKRETV LTFIDPEGSEVDMVEEIDHIGIISFPDFKIPSNPRYGMWTIKAKYKEDFSTTGTAYFEVKEYVLPHFSVSIEPEYNFIGY KNFKNFEITIKARYFYNKVVTEADVYITFGIREDLKDDQKEMMQTAMQNTMLINGIAQVTFDSETAVKELSYYSLEDLNN KYLYIAVTVIESTGGFSEEAEIPGIKYVLSPYKLNLVATPLFLKPGIPYPIKVQVKDSLDQLVGGVPVTLNAQTIDVNQE TSDLDPSKSVTRVDDGVASFVLNLPSGVTVLEFNVKTDAPDLPEENQAREGVRAIAYSSLSQSYLYIDWTDNHKALLVGE HLNLIVTPKSPYIDKITHYNYLILSKGKIIHFGTREKFSDASYQSINIPVTQNMVPSSRLLVYYIVTGEQTAELVSDSVW LNIEEKCGNQLQVHLSPDADAYSPGQTVSLNMATGMDSWVALAAVDSAVYGVQRGAKKPLERVFQFLEKSDLGCGAGGGL NNANVFHLAGLTFLTNANADDSQENDEPCKEILRPRRTLQKKIEEIAAKYKHSVVKKCCYDGACVNNDETCEQRAARISL | 251 |

Figure 7J

| | | |
|---|---|---|
| | GPRCIKAFTECCVVASQLRANISHKDMQLGRLHMKTLLPVSKPEIRSYFPESWLMEVHLIVPRRKQLQFALPDSLTTWEIQ GVGISNTGICVADITVKAKVFKDVFLEMNIPYSVVRGEQIQLKGTVYNYRTSGMQFCVKMSAVEGICTSESPVIDHQGTKS SKCVRQKVEGSSHLVTFTVLPLEIGLHNINFSLETWFGKEILVKTLRVVPEGVKRESYSGVTLDPRGIYGTISRRKEFP YRIPLDLVPKTEIKRILSVKGLLVGEILSAVLSQEGINILTHLPKGSAEAELMSVVPFYVFHYLETGNHWNIFHSDPLI EKQKLKKLKEGMLSIMSYRNADYSYSVWKGGSASTWLTAFALRVLGQVNKYVEQNQNSICNSLLWLVENYQLDNGSFKE NSQYQPIKLQGTLPVEARENSLYLTAFTVIGIRKAFDICPLVKIDTALIKADNFLLENTLPAQSFFTLAISAYALSLGDK THPQFRSIVSALKREALVKGNPPIYRFWKDNLQHKDSSVPNTGTARMVETTAYALLTSLNLKDINYVNPVIKWLSEEQRY GGGFYSTQDTINAIEGLTEYSLLVKQLRLSMDIDVSYKHKGALHNYKMTDKNFLGRPVEVLINDDLIVSTGFGSGLATVH VTTVVHKTSTSEEVCSFYLKIDTQDIEASHYRGYGNSDYKRIVACASYKPSREESSSGSSHAVMDISLPTGISANEEDLK ALVEGVDQLFTDYQIKDGHVILQLNSIPSSDFLCVRFRIFELFEVGFLSPATFTVEYHRPDKQCTMFYSTSNIKIQKVC EGAACKCVEADCGQMQEELDLTISAETRKQTACKPEIAYAYKVSITSIITVENVFVKYKATLLDIYKTGEAVAEKDSEITF IKKVTCTNAELVKGRQYLIMGKEALQIKYNFSFRYIYPLDSLTMIEYWPRDTTCSSCQAFLANLDEFAEDIFLNGC | |
| PSI0332 | AEAKYAKEVLEAWDEIDRLPNLTIEQWLAFINKLDRQPEQSSELLSEAKKLNDSQAPKVDGSLAEAKEAANAELDSYGVSDFYKRLIDKAKTV EGVEALKDAILAALP | 252 |
| PSI0334 | AEAKYAKEVLEAWDEIDRLPNLTIEQWLAFINKLDDDPSQSSELLSEAKKLNDSQAPKVDGSLAEAKEAANAELDSYGVSDFYKRLIDKAKTV EGVEALKDAILAALP | 253 |
| PSI0335 | AEAKYAKEVLEAWDEIDRLPNLTIEQWLAFINKLDDDPSQSSELLSEAKKLNDSQAPKVDGSLAEAKVLANRELDKYGVSDFYKRLINKAKTV EGVEALKLHILAALP | 254 |
| PSI0336 | AEAKYAKEVLEAWSEIDRLPNLTIEQWLAFINKLDDDPSQSSELLSEAKKLNDSQAPKVDGSLAEAKEAANAELDSYGVSDFYKRLIDKAKTV EGVEALKDAILAALP | 255 |
| PSI0337 | AEAKYAKEVLEAWDEIERLPNLTIEQWLAFINKLDDDPSQSSELLSEAKKLNDSQAPKVDGSLAEAKEAANAELDSYGVSDFYKRLIDKAKTV EGVEALKDAILAALP | 256 |
| PSI0339 | AEAKYAKEVLEAWDEIDRLPNLTIEQWLAFIAKLDDDPSQSSELLSEAKKLNDSQAPKVDGSLAEAKEAANAELDSYGVSDFYKRLIDKAKTV EGVEALKDAILAALP | 257 |
| PSI0340 | AEAKYAKEVLEAWDEIDRLPNLTIEQWLAFINKLEDDPSQSSELLSEAKKLNDSQAPKVDGSLAEAKEAANAELDSYGVSDFYKRLIDKAKTV EGVEALKDAILAALP | 258 |
| PSI0369 | AEAKYAKEVLEAWDEIDRLPNLTIEQWLAFINKLDDDPSQSSELLSEAKKLNDSQAPLAEAKEAANAELDSYGVSDFYKRLIDKAKTVEGVEA LKDAILAALP | 259 |
| PSI0377 | AEAKYAKEVLEAWDEIDRLPNLTIEQWLAFINKLDDDPSQSSELLSEAKKLSESQAP | 260 |
| PSI0378 | AEAKYAKEVLEAWDEIDRLPNLTIEQWLAFINKLDDDPSQSSELLSEAKKLSESQAPKVEGSLAEAKEAANAELDSYGVSDFYKRLIDKAKTV EGVEALKDAILAALP | 261 |
| PSI0379 | AEAKYAKEVLEAWDEIDRLPNLTIEQWLAFINKLDDDPSQSSELLSEAKKLSESQAPKVAGSLAEAKEAANAELDSYGVSDFYKRLIDKAKTV EGVEALKDAILAALP | 262 |

Figure 7K

| | | |
|---|---|---|
| PSI0381 | AEAKYAKEVLEAWDEIDRLPNLTIEQWLAFINKLDDDPSQSSELLSEAKKLESSQAPKVEGSLAEAKEANAELDSYGVSDFYKRLIDKAKTV EGVEALKDAILAALP | 263 |
| PSI0383 | AEAKYAKEVLEAWDEIDRLPNLTIEQWLAFINKLDRQPEQSSELLSEAKKLSESQAPKVEGSLAEAKEANAELDSYGVSDFYKRLIDKAKTV EGVEALKDAILAALP | 264 |
| PSI0389 | AEAKYAKEVLEAWDEIDRLPNLTIEQWLAFINKLDDDPSQSSELLSEAKKLESSQAP | 265 |
| PSI0390 | AEAKYAKEVLEAWDEIDRLPNLTIEQWLAFINKLDRQPEQSSELLSEAKKLSESQAP | 266 |
| PSI0400 | AEAKYAKEVLEAWDEIDRLPNLTIEQWLAFINKLDDDPSQSSELLSEAKKLSESQAPK | 267 |
| PSI0410 | AEAKYAKEVLEAWDEIDRLPNLTIEQWLAFINKLDDDPSQSSELLSEAKKLNDSQAPKVEGSLAEAKEANAELDSYGVSDFYKRLIDKAKTV EGVEALKDAILAALP | 268 |
| PSI0403 | AEAKYAKEVLEAWDEIDRLPNLTIEQWLAFINKLDDDPSQSSELLSEAKKLNESQAPKVEGSLAEAKEANAELDSYGVSDFYKRLIDKAKTV EGVEALKDAILAALP | 269 |
| PSI0404 | AEAKYAKEVLEAWDEIDRLPNLTIEQWLAFINKLDDDPSQSSELLSEAKKLSDSQAPKVEGSLAEAKEANAELDSYGVSDFYKRLIDKAKTV EGVEALKDAILAALP | 270 |
| PSI0257 | AEAKYAKEVLEAWDEIDRLPNLTIEQWLAFINKLDDDPSQSSELLSEAKKLNDSQAPKVDGS | 271 |
| Z02891 | AEAKYAKEMRNAYWEIALLPNLTNQQKRAFIRKLYDDPSQPEQSSELLSEAKKLSESQAPK | 272 |
| Z17341 | AEAKYAKEMRNAYWEIALLPNLTNQQKRAFIRKLYDDPSQSSELLSEAKKLSESQAPK | 273 |
| Z17342 | AEAKYAKEMRNAYWEIALLPNLTNQQKRAFIRKLYRQPEQSSELLSEAKKLSESQAPK | 274 |
| Z15805 | AEAKYAKELIEAAAEIDALPNLTRRQWNAFIKKLVDDPSQSSELLSEAKKLNDSQAPK | 275 |
| Z17343 | AEAKYAKELIEAAAEIDALPNLTRRQWNAFIKKLVDDPSQSSELLSEAKKLSESQAPK | 276 |
| Z17344 | AEAKYAKELIEAAAEIDALPNLTRRQWNAFIKKLVRQPEQSSELLSEAKKLSESQAPK | 277 |
| Z10103 | AEAKYAKEQDAAAHEIRWLPNLTFDQRVAFIHKLADDPSQSSELLSEAKKLNDSQAPK | 278 |
| Z17347 | AEAKYAKEQDAAAHEIRWLPNLTFDQRVAFIHKLADDPSQSSELLSEAKKLSESQAPK | 279 |
| Z17348 | AEAKYAKEQDAAAHEIRWLPNLTFDQRVAFIHKLARQPEQSSELLSEAKKLSESQAPK | 280 |
| Z09782 | AEAKYAKENLFAGWEISDLPNLTDYQRNAFIYKLWDDPSQSSELLSEAKKLNDSQAPK | 281 |
| Z17351 | AEAKYAKENLFAGWEISDLPNLTDYQRNAFIYKLWDDPSQSSELLSEAKKLSESQAPK | 282 |
| Z17352 | AEAKYAKENLFAGWEISDLPNLTDYQRNAFIYKLWRQPEQSSELLSEAKKLSESQAPK | 283 |
| Z17355 | AEAKYAKENLFAGWEISDLPNLTDYQRNAFIYKLWDDPSQSSELLSEAKKLNESQAPK | 284 |

Figure 7L

| Z17357 | AEAKYAKENLFAGWEISDLPNLTDYQRNAFIYKLWRQPEQSSELLSEAKKLNESQAPK | 285 |
| Z17359 | AEAKYAKENLFAGWEISDLPNLTDYQRNAFIYKLWDDPSQSSELLSEAKKLSDSQAPK | 286 |
| Z17360 | AEAKYAKENLFAGWEISDLPNLTDYQRNAFIYKLWRQPEQSSELLSEAKKLSDSQAPK | 287 |

Figure 7M

```
                        SEQUENCE LISTING

<160> NUMBER OF SEQ ID NOS: 299

<210> SEQ ID NO 1
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 1

Glu Val Leu Glu Ala Trp Asp Glu Ile Asp Arg Leu Pro Asn Leu Thr
1               5                   10                  15
```

Ile Glu Gln Trp Leu Ala Phe Ile Asn Lys Leu Asp Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 2

Glu Val Leu Glu Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 3
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 3

Glu Val Ile Glu Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 4
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 4

Glu Val Leu Glu Ala Trp Asp Glu Ile Asp Arg Leu Pro Asn Leu Thr
1               5                   10                  15

Leu Asp Gln Trp Leu Ala Phe Ile Asn Lys Leu Asp Asp
            20                  25

<210> SEQ ID NO 5
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 5

Glu Val Leu Asp Ala Trp Asp Glu Ile Asp Ala Leu Pro Asn Leu Thr
1               5                   10                  15

Leu Glu Gln Trp Leu Ala Phe Ile Asn Lys Leu Asp Asp
            20                  25

<210> SEQ ID NO 6
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 6

Glu Val Ile Asp Ala Trp Asp Glu Ile Asp Arg Leu Pro Asn Leu Thr
1               5                   10                  15

Leu Asp Gln Trp Leu Ala Phe Ile Asn Lys Leu Asp Asp
            20                  25

<210> SEQ ID NO 7
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 7

Glu Thr Leu Glu Ala Trp Asp Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 8
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 8

Glu Val Ile Asp Ala Trp Asn Glu Ile Asp Ala Leu Pro Asn Leu Thr
1               5                   10                  15

Leu Asp Gln Trp Leu Ala Phe Ile Asn Lys Leu Asp Asp
            20                  25

<210> SEQ ID NO 9
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 9

Glu Val Leu Asp Ala Trp Asp Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 10

Glu Val Leu Glu Ala Trp Asp Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 11
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 11

Glu Val Leu Glu Ala Trp Asp Glu Ile Asp Ala Leu Pro Asn Leu Thr

```
1               5                   10                  15

Ile Glu Gln Trp Leu Ala Phe Ile Asn Lys Leu Asp Asp
            20                  25

<210> SEQ ID NO 12
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 12

Glu Val Leu Asp Ala Trp Asp Glu Ile Asp Lys Leu Pro Asn Leu Thr
1               5                   10                  15

Leu Glu Gln Trp Leu Ala Phe Ile Asn Lys Leu Asp Asp
            20                  25

<210> SEQ ID NO 13
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 13

Glu Thr Ile Thr Ala Trp Asp Glu Ile Asp Lys Leu Pro Asn Leu Thr
1               5                   10                  15

Ile Glu Gln Trp Leu Ala Phe Ile Gly Lys Leu Glu Asp
            20                  25

<210> SEQ ID NO 14
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 14

Glu Ser Met Lys Ala Trp Asp Glu Ile Asp Arg Leu Pro Asn Leu Asn
1               5                   10                  15

Ile Asn Gln Trp Val Ala Phe Ile Asp Ser Leu Tyr Asp
            20                  25

<210> SEQ ID NO 15
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 15

Glu Ser Ile Glu Ala Trp Thr Glu Ile Asp His Leu Pro Asn Leu Thr
1               5                   10                  15

Ile Glu Gln Trp Leu Ala Phe Ile Asn Lys Leu Thr Asp
            20                  25

<210> SEQ ID NO 16
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 16
```

```
Glu Val Leu Asp Ala Trp His Glu Ile Asp Thr Leu Pro Asn Leu Thr
1               5                   10                  15

Val Arg Gln Trp Leu Ala Phe Ile Ser Lys Leu Glu Asp
            20                  25
```

<210> SEQ ID NO 17
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 17

```
Glu His Ile Gln Ala Asn Glu Glu Ile Asp Arg Leu Pro Asn Leu Thr
1               5                   10                  15

Ile Lys Gln Trp Leu Ala Phe Ile Asn Lys Leu His Asp
            20                  25
```

<210> SEQ ID NO 18
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 18

```
Glu Val Leu His Ala Trp Ala Glu Ile Asp Ala Leu Pro Asn Leu Thr
1               5                   10                  15

Ile Glu Gln Trp Leu Ala Phe Ile Asn Lys Leu Asp Asp
            20                  25
```

<210> SEQ ID NO 19
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 19

```
Glu Val Leu Ala Ala Trp Asp Glu Ile Asp Ser Leu Pro Asn Leu Thr
1               5                   10                  15

Leu Gln Gln Trp Leu Ala Phe Ile Asn Lys Leu Asp Asp
            20                  25
```

<210> SEQ ID NO 20
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 20

```
Glu Val Ile Asp Ala Trp Asn Glu Ile Asp Ala Leu Pro Asn Leu Thr
1               5                   10                  15

Leu Glu Gln Trp Leu Ala Phe Ile Asn Lys Leu Asp Asp
            20                  25
```

<210> SEQ ID NO 21
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 21

-continued

Glu Val Leu Asp Ala Trp Asn Glu Ile Asp Ala Leu Pro Asn Leu Thr
1               5                   10                  15

Ile Asp Gln Trp Leu Ala Phe Ile Asn Lys Leu Ser Asp
            20                  25

<210> SEQ ID NO 22
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 22

Glu Val Ile Glu Ala Trp Asp Glu Ile Asp Gly Leu Pro Asn Leu Thr
1               5                   10                  15

Ile Glu Gln Trp Leu Ala Phe Ile Asn Lys Leu Asp Asp
            20                  25

<210> SEQ ID NO 23
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 23

Glu Val Leu Glu Ala Trp Asp Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 24
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 24

Glu Val Ile Glu Ala Trp Asn Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 25
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 25

Glu Val Ile Ala Ala Trp Asn Glu Ile Asp Arg Leu Pro Asn Leu Thr
1               5                   10                  15

Leu Thr Gln Trp Leu Ala Phe Ile Asn Lys Leu Asp Asp
            20                  25

<210> SEQ ID NO 26
<211> LENGTH: 29
<212> TYPE: PRT
<213> ORGANISM: Artificial Sequence
<220> FEATURE:
<223> OTHER INFORMATION: Modified bacterial sequence

```
<400> SEQUENCE: 26

Glu Val Ile Glu Ala Trp Asp Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 27
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 27

Glu Val Ile Ala Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 28
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 28

Glu Val Ile Ala Ala Trp Asp Glu Ile Asp Lys Leu Pro Asn Leu Thr
1               5                   10                  15

Leu Gln Gln Trp Leu Ala Phe Ile Asn Lys Leu Asp Asp
            20                  25

<210> SEQ ID NO 29
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 29

Glu Thr Ile Ala Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 30
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 30

Glu Thr Ile Glu Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 31
<211> LENGTH: 29
<212> TYPE: PRT
<213> ORGANISM: Artificial Sequence
<220> FEATURE:
<223> OTHER INFORMATION: Modified bacterial sequence
```

<400> SEQUENCE: 31

Glu Val Leu Glu Ala Trp Arg Glu Ile Asp Ala Leu Pro Asn Leu Thr
1               5                   10                  15

Ile Gln Gln Trp Leu Ala Phe Ile Asn Lys Leu Asp Asp
                20                  25

<210> SEQ ID NO 32
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 32

Glu Val Ile Glu Ala Trp Asp Glu Ile Asp Gln Leu Pro Asn Leu Thr
1               5                   10                  15

Ile Glu Gln Trp Leu Ala Phe Ile Asn Lys Leu Asp Asp
                20                  25

<210> SEQ ID NO 33
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 33

Glu Val Leu Arg Ala Trp Asp Glu Ile Asp His Leu Pro Asn Leu Thr
1               5                   10                  15

Leu Glu Gln Trp Leu Ala Phe Ile Asn Lys Leu Asp Asp
                20                  25

<210> SEQ ID NO 34
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 34

Glu Val Leu Glu Ala Trp Asp Glu Ile Asp Arg Leu Pro Asn Leu Thr
1               5                   10                  15

Leu Asn Gln Trp Leu Ala Phe Ile Asn Lys Leu Asp Asp
                20                  25

<210> SEQ ID NO 35
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 35

Glu Val Leu Asp Ala Trp Asn Glu Ile Asp His Leu Pro Asn Leu Thr
1               5                   10                  15

Ile Glu Gln Trp Leu Ala Phe Ile Asn Lys Leu Asp Asp
                20                  25

<210> SEQ ID NO 36
<211> LENGTH: 29
<212> TYPE: PRT
<213> ORGANISM: Artificial Sequence
<220> FEATURE:

<223> OTHER INFORMATION: Modified bacterial sequence

<400> SEQUENCE: 36

Glu Val Ile Asp Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 37
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 37

Glu Thr Leu Glu Ala Trp Asp Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 38
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 38

Glu Val Ile Glu Ala Trp Asn Glu Ile Asp Ala Leu Pro Asn Leu Thr
1               5                   10                  15

Leu Asp Gln Trp Leu Ala Phe Ile Asn Lys Leu Asp Asp
            20                  25

<210> SEQ ID NO 39
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 39

Glu Val Ile Asp Ala Trp Asn Glu Ile Asp Arg Leu Pro Asn Leu Thr
1               5                   10                  15

Leu Gln Gln Trp Leu Ala Phe Ile Asn Lys Leu Asp Asp
            20                  25

<210> SEQ ID NO 40
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 40

Glu Val Ile Asp Ala Trp Asn Glu Ile Asp Gln Leu Pro Asn Leu Thr
1               5                   10                  15

Leu Glu Gln Trp Leu Ala Phe Ile Asn Lys Leu Asp Asp
            20                  25

<210> SEQ ID NO 41
<211> LENGTH: 29
<212> TYPE: PRT
<213> ORGANISM: Artificial Sequence

```
<220> FEATURE:
<223> OTHER INFORMATION: Modified bacterial sequence

<400> SEQUENCE: 41

Glu Thr Ile Ala Ala Trp Asp Glu Ile Asp His Leu Pro Asn Leu Thr
1               5                   10                  15

Leu Glu Gln Trp Leu Ala Phe Ile Asn Lys Leu Asp Asp
            20                  25

<210> SEQ ID NO 42
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 42

Glu Val Leu Gln Ala Trp Asp Glu Ile Asp His Leu Pro Asn Leu Thr
1               5                   10                  15

Ile Gln Gln Trp Leu Ala Phe Ile Asn Lys Leu Ser Asp
            20                  25

<210> SEQ ID NO 43
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 43

Glu Thr Leu His Ala Trp Ala Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 44
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 44

Glu Val Leu Gln Ala Trp Asn Glu Ile Asp His Leu Pro Asn Leu Thr
1               5                   10                  15

Leu Ala Gln Trp Leu Ala Phe Ile Asn Lys Leu Asp Asp
            20                  25

<210> SEQ ID NO 45
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 45

Glu Val Ile Glu Ala Trp Asp Glu Ile Asp Lys Leu Pro Asn Leu Thr
1               5                   10                  15

Ile Ala Gln Trp Leu Ala Phe Ile Asn Lys Leu Asp Asp
            20                  25

<210> SEQ ID NO 46
<211> LENGTH: 29
<212> TYPE: PRT
```

```
<213> ORGANISM: Artificial Sequence
<220> FEATURE:
<223> OTHER INFORMATION: Modified bacterial sequence

<400> SEQUENCE: 46

Glu Val Leu Asp Ala Trp Asp Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 47
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 47

Glu Thr Ile Glu Ala Trp Asn Glu Ile Asp Lys Leu Pro Asn Leu Thr
1               5                   10                  15

Leu Thr Gln Trp Leu Ala Phe Ile Asn Lys Leu Asp Asp
            20                  25

<210> SEQ ID NO 48
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 48

Glu Val Leu Glu Ala Trp Asn Glu Ile Asp Leu Leu Pro Asn Leu Thr
1               5                   10                  15

Ile Glu Gln Trp Leu Ala Phe Ile Asn Lys Leu Asp Asp
            20                  25

<210> SEQ ID NO 49
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 49

Glu Val Ile Glu Ala Trp Asp Glu Ile Asp His Leu Pro Asn Leu Thr
1               5                   10                  15

Ile Asp Gln Trp Leu Ala Phe Ile Asn Lys Leu Asp Asp
            20                  25

<210> SEQ ID NO 50
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 50

Glu Val Ile Ser Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 51
<211> LENGTH: 29
```

```
<212> TYPE: PRT
<213> ORGANISM: Artificial Sequence
<220> FEATURE:
<223> OTHER INFORMATION: Modified bacterial sequence

<400> SEQUENCE: 51

Glu Val Ile Ala Ala Trp Asn Glu Ile Asp Lys Leu Pro Asn Leu Thr
1               5                   10                  15

Leu Glu Gln Trp Leu Ala Phe Ile Asn Lys Leu Asp Asp
            20                  25

<210> SEQ ID NO 52
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 52

Glu Thr Ile Glu Ala Trp Asn Glu Ile Asp Ser Leu Pro Asn Leu Thr
1               5                   10                  15

Leu Asp Gln Trp Leu Ala Phe Ile Asn Lys Leu Asp Asp
            20                  25

<210> SEQ ID NO 53
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 53

Glu Val Leu Asp Ala Trp Asn Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 54
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 54

Glu Val Leu Ala Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 55
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 55

Glu Val Leu Glu Ala Trp Asp Glu Ile Asp His Leu Pro Asn Leu Thr
1               5                   10                  15

Ile Thr Gln Trp Leu Ala Phe Ile Asn Lys Leu Asp Asp
            20                  25

<210> SEQ ID NO 56
```

<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 56

Glu Thr Ile Asp Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 57
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 57

Glu Val Ile Glu Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 58
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 58

Glu Val Ile Gln Ala Trp Asn Glu Ile Asp Ala Leu Pro Asn Leu Thr
1               5                   10                  15

Ile Ser Gln Trp Leu Ala Phe Ile Asn Lys Leu Asp Asp
            20                  25

<210> SEQ ID NO 59
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 59

Glu Val Ile Ala Ala Trp Asp Glu Ile Asp Ser Leu Pro Asn Leu Thr
1               5                   10                  15

Ile Glu Gln Trp Leu Ala Phe Ile Asn Lys Leu Asp Asp
            20                  25

<210> SEQ ID NO 60
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 60

Glu His Ile Glu Ala Trp Asn Glu Ile Asp Ala Leu Pro Asn Leu Thr
1               5                   10                  15

Ile Glu Gln Trp Leu Ala Phe Ile Asn Lys Leu Gln Asp
            20                  25

```
<210> SEQ ID NO 61
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 61

Glu Val Leu Glu Ala Trp Asn Glu Ile Asp Lys Leu Pro Asn Leu Thr
1               5                   10                  15

Leu Asp Gln Trp Leu Ala Phe Ile Asn Lys Leu Asp Asp
            20                  25

<210> SEQ ID NO 62
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 62

Glu Val Ile Asp Ala Trp Asn Glu Ile Asp His Leu Pro Asn Leu Thr
1               5                   10                  15

Ile Glu Gln Trp Leu Ala Phe Ile Asn Lys Leu Ala Asp
            20                  25

<210> SEQ ID NO 63
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 63

Glu Thr Ile Asp Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 64
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 64

Glu Val Ile Ala Ala Trp Asp Glu Ile Asp Leu Leu Pro Asn Leu Thr
1               5                   10                  15

Leu Gln Gln Trp Leu Ala Phe Ile Asn Lys Leu Ala Asp
            20                  25

<210> SEQ ID NO 65
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 65

Glu Val Ile His Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25
```

<210> SEQ ID NO 66
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 66

Glu Val Ile Ala Ala Trp Asn Glu Ile Asp His Leu Pro Asn Leu Thr
1               5                   10                  15

Leu Glu Gln Trp Leu Ala Phe Ile Asn Lys Leu Asp Asp
            20                  25

<210> SEQ ID NO 67
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 67

Glu Thr Leu Asp Ala Trp Asn Glu Ile Asp Lys Leu Pro Asn Leu Thr
1               5                   10                  15

Leu Ser Gln Trp Leu Ala Phe Ile Asn Lys Leu Asp Asp
            20                  25

<210> SEQ ID NO 68
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 68

Glu Val Leu Glu Ala Trp Asn Glu Ile Asp Ala Leu Pro Asn Leu Thr
1               5                   10                  15

Leu Glu Gln Trp Leu Ala Phe Ile Asn Lys Leu Asp Asp
            20                  25

<210> SEQ ID NO 69
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 69

Glu Val Ile Gln Ala Trp Asp Glu Ile Asp His Leu Pro Asn Leu Thr
1               5                   10                  15

Ile Ser Gln Trp Leu Ala Phe Ile Asn Lys Leu Asp Asp
            20                  25

<210> SEQ ID NO 70
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 70

Glu Val Leu Gln Ala Trp Asp Glu Ile Asp Ser Leu Pro Asn Leu Thr
1               5                   10                  15

Ile Glu Gln Trp Leu Ala Phe Ile Asn Lys Leu Asp Asp
            20                  25

<210> SEQ ID NO 71
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 71

Glu Thr Leu Glu Ala Trp Asp Glu Ile Asp His Leu Pro Asn Leu Thr
1               5                   10                  15

Ile Ala Gln Trp Leu Ala Phe Ile Asn Lys Leu Asp Asp
            20                  25

<210> SEQ ID NO 72
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 72

Glu Thr Ile Asp Ala Trp Asn Glu Ile Asp Arg Leu Pro Asn Leu Thr
1               5                   10                  15

Ile Ser Gln Trp Leu Ala Phe Ile Asn Lys Leu Asp Asp
            20                  25

<210> SEQ ID NO 73
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 73

Glu Val Leu Asp Ala Trp His Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 74
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 74

Glu Gln Ile Arg Ala Trp Asp Glu Ile Asp Lys Leu Pro Asn Leu Thr
1               5                   10                  15

Ile Glu Gln Trp Leu Ala Phe Ile Asn Lys Leu Ala Asp
            20                  25

<210> SEQ ID NO 75
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 75

Glu Thr Leu Tyr Ala Trp Asn Glu Ile Asp Lys Leu Pro Asn Leu Thr
1               5                   10                  15

Ile Glu Gln Trp Leu Ala Phe Ile Glu Lys Leu Gln Asp

```
                20                  25

<210> SEQ ID NO 76
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 76

Glu Val Ile Glu Ala Trp Asn Glu Ile Asp Ala Leu Pro Asn Leu Thr
1               5                   10                  15

Ile Asp Gln Trp Leu Ala Phe Ile Asn Lys Leu Asp Asp
            20                  25

<210> SEQ ID NO 77
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 77

Glu Val Leu Glu Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 78
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 78

Glu Thr Ile Glu Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 79
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 79

Glu Val Ile Glu Ala Trp Asn Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 80
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 80

Glu Val Ile Glu Ala Trp Asn Glu Ile Asp Lys Leu Pro Asn Leu Thr
1               5                   10                  15
```

Ile Gln Gln Trp Leu Ala Phe Ile Asn Lys Leu Asp Asp
            20                  25

<210> SEQ ID NO 81
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 81

Glu Thr Leu Asp Ala Trp Ala Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 82
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 82

Glu His Ile Asp Ala Trp Asn Glu Ile Asp Ala Leu Pro Asn Leu Thr
1               5                   10                  15

Leu Ser Gln Trp Leu Ala Phe Ile Asn Lys Leu Asp Asp
            20                  25

<210> SEQ ID NO 83
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 83

Glu Val Leu Asp Ala Trp Asn Glu Ile Asp Lys Leu Pro Asn Leu Thr
1               5                   10                  15

Ile Ala Gln Trp Leu Ala Phe Ile Asn Lys Leu Asp Asp
            20                  25

<210> SEQ ID NO 84
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 84

Glu Val Ile Glu Ala Trp Thr Glu Ile Asp Tyr Leu Pro Asn Leu Thr
1               5                   10                  15

Leu Gln Gln Trp Leu Ala Phe Ile Asn Lys Leu Asp Asp
            20                  25

<210> SEQ ID NO 85
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 85

Glu Thr Ile Glu Ala Trp Asn Glu Ile Asp His Leu Pro Asn Leu Thr
1               5                   10                  15

```
Ile Ala Gln Trp Leu Ala Phe Ile Asn Lys Leu Asp Asp
            20                  25
```

<210> SEQ ID NO 86
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 86

```
Glu Val Ile Gln Ala Trp Asn Glu Ile Asp Lys Leu Pro Asn Leu Thr
1               5                   10                  15

Leu Glu Gln Trp Leu Ala Phe Ile Asn Lys Leu Asp Asp
            20                  25
```

<210> SEQ ID NO 87
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 87

```
Glu Val Ile Glu Ala Trp Asp Glu Ile Asp His Leu Pro Asn Leu Thr
1               5                   10                  15

Ile Glu Gln Trp Leu Ala Phe Ile Asn Lys Leu Asp Asp
            20                  25
```

<210> SEQ ID NO 88
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 88

```
Glu Thr Ile Asp Ala Trp Asn Glu Ile Asp Leu Leu Pro Asn Leu Thr
1               5                   10                  15

Ile Glu Gln Trp Leu Ala Phe Ile Asn Lys Leu Asp Asp
            20                  25
```

<210> SEQ ID NO 89
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 89

```
Glu His Ile Asp Ala Trp Asn Glu Ile Asp Lys Leu Pro Asn Leu Thr
1               5                   10                  15

Leu Asp Gln Trp Leu Ala Phe Ile Asn Lys Leu Asp Asp
            20                  25
```

<210> SEQ ID NO 90
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 90

```
Glu Val Val Ala Ala Trp Asn Glu Ile Asp Ala Leu Pro Asn Leu Thr
```

```
1               5                   10                  15
Ile Glu Gln Trp Leu Ala Phe Ile Asn Lys Leu Asn Asp
                20                  25
```

<210> SEQ ID NO 91
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 91

```
Glu Val Ile Glu Ala Trp Asn Glu Ile Asp Ala Leu Pro Asn Leu Thr
1               5                   10                  15
Leu Ala Gln Trp Leu Ala Phe Ile Asn Lys Leu Asp Asp
                20                  25
```

<210> SEQ ID NO 92
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 92

```
Glu Val Leu Gln Ala Trp Asp Glu Ile Asp Arg Leu Pro Asn Leu Thr
1               5                   10                  15
Leu Asp Gln Trp Leu Ala Phe Ile Asn Lys Leu Asp Asp
                20                  25
```

<210> SEQ ID NO 93
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 93

```
Glu Val Ile Asp Ala Trp Asp Glu Ile Asp His Leu Pro Asn Leu Thr
1               5                   10                  15
Ile Glu Gln Trp Leu Ala Phe Ile Asn Lys Leu Ser Asp
                20                  25
```

<210> SEQ ID NO 94
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 94

```
Glu Val Val Glu Ala Trp Asn Glu Ile Asp Gln Leu Pro Asn Leu Thr
1               5                   10                  15
Ile Glu Gln Trp Leu Ala Phe Ile Asn Lys Leu Asp Asp
                20                  25
```

<210> SEQ ID NO 95
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 95

-continued

Glu Val Ile Gln Ala Trp Asn Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 96
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 96

Glu Val Ile Gln Ala Trp Asp Glu Ile Asp Lys Leu Pro Asn Leu Thr
1               5                   10                  15

Ile Asp Gln Trp Leu Ala Phe Ile Asn Lys Leu Ala Asp
            20                  25

<210> SEQ ID NO 97
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 97

Glu Val Val Ala Ala Trp Asp Glu Ile Asp Ala Leu Pro Asn Leu Thr
1               5                   10                  15

Leu Thr Gln Trp Leu Ala Phe Ile Asn Lys Leu Asp Asp
            20                  25

<210> SEQ ID NO 98
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 98

Glu Val Ile Gln Ala Trp Asn Glu Ile Asp Gly Leu Pro Asn Leu Thr
1               5                   10                  15

Leu Ser Gln Trp Leu Ala Phe Ile Asn Lys Leu Asp Asp
            20                  25

<210> SEQ ID NO 99
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 99

Glu Thr Ile Glu Ala Trp Asp Glu Ile Asp Ala Leu Pro Asn Leu Thr
1               5                   10                  15

Ile Thr Gln Trp Leu Ala Phe Ile Asn Lys Leu Asp Asp
            20                  25

<210> SEQ ID NO 100
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 100

```
Glu Val Ile Asp Ala Trp Asn Glu Ile Asp His Leu Pro Asn Leu Thr
1               5                   10                  15

Ile Gln Gln Trp Leu Ala Phe Ile Asn Lys Leu Ala Asp
            20                  25

<210> SEQ ID NO 101
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 101

Glu Thr Ile Glu Ala Trp Asn Glu Ile Asp Ala Leu Pro Asn Leu Thr
1               5                   10                  15

Leu Asp Gln Trp Leu Ala Phe Ile Asn Lys Leu Glu Asp
            20                  25

<210> SEQ ID NO 102
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 102

Glu His Ile His Ala Trp Asn Glu Ile Asp Glu Leu Pro Asn Leu Thr
1               5                   10                  15

Ile Glu Gln Trp Leu Ala Phe Ile Asn Lys Leu Ala Asp
            20                  25

<210> SEQ ID NO 103
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 103

Glu Val Ile Asp Ala Trp Asp Glu Ile Asp His Leu Pro Asn Leu Thr
1               5                   10                  15

Ile Asp Gln Trp Leu Ala Phe Ile Asn Lys Leu Ser Asp
            20                  25

<210> SEQ ID NO 104
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 104

Glu Val Ile Asp Ala Asn Asp Glu Ile Asp Ala Leu Pro Asn Leu Thr
1               5                   10                  15

Ile Ala Gln Trp Leu Ala Phe Ile Asn Lys Leu His Asp
            20                  25

<210> SEQ ID NO 105
<211> LENGTH: 29
<212> TYPE: PRT
<213> ORGANISM: Artificial Sequence
<220> FEATURE:
<223> OTHER INFORMATION: Modified bacterial sequence
```

```
<400> SEQUENCE: 105

Glu Thr Ile Glu Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 106
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 106

Glu Val Leu Leu Ala Trp Asp Glu Ile Asp His Leu Pro Asn Leu Thr
1               5                   10                  15

Leu Glu Gln Trp Leu Ala Phe Ile Asn Lys Leu Asp Asp
            20                  25

<210> SEQ ID NO 107
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 107

Glu His Ile Asp Ala Trp Asn Glu Ile Asp Gly Leu Pro Asn Leu Thr
1               5                   10                  15

Leu Glu Gln Trp Leu Ala Phe Ile Asn Lys Leu Asp Asp
            20                  25

<210> SEQ ID NO 108
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 108

Glu Val Ile Glu Ala Trp Ser Glu Ile Asp Ala Leu Pro Asn Leu Thr
1               5                   10                  15

Ile Asp Gln Trp Leu Ala Phe Ile Asn Lys Leu Ala Asp
            20                  25

<210> SEQ ID NO 109
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 109

Glu Gln Leu Asn Ala Trp Ala Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 110
<211> LENGTH: 29
<212> TYPE: PRT
<213> ORGANISM: Artificial Sequence
<220> FEATURE:
<223> OTHER INFORMATION: Modified bacterial sequence
```

<400> SEQUENCE: 110

Glu Val Ile Asp Ala Trp Asn Glu Ile Asp Ala Leu Pro Asn Leu Thr
1               5                   10                  15

Ile Ala Gln Trp Leu Ala Phe Ile Asn Lys Leu Asp Asp
            20                  25

<210> SEQ ID NO 111
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 111

Glu Thr Ile Asp Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 112
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 112

Glu Val Ile Glu Ala Trp Asp Glu Ile Asp Lys Leu Pro Asn Leu Thr
1               5                   10                  15

Leu Ala Gln Trp Leu Ala Phe Ile Asn Lys Leu Asp Asp
            20                  25

<210> SEQ ID NO 113
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 113

Glu Val Leu Tyr Ala Trp Ala Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 114
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 114

Glu Gln Ile Asp Ala Trp Asn Glu Ile Asp Arg Leu Pro Asn Leu Thr
1               5                   10                  15

Ile Gln Gln Trp Leu Ala Phe Ile Asn Lys Leu Asp Asp
            20                  25

<210> SEQ ID NO 115
<211> LENGTH: 29
<212> TYPE: PRT
<213> ORGANISM: Artificial Sequence
<220> FEATURE:

<223> OTHER INFORMATION: Modified bacterial sequence

<400> SEQUENCE: 115

Glu Val Leu Ala Ala Trp Asp Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 116
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 116

Glu Val Ile Glu Ala Trp Asp Glu Ile Asp His Leu Pro Asn Leu Thr
1               5                   10                  15

Leu His Gln Trp Leu Ala Phe Ile Asn Lys Leu Asp Asp
            20                  25

<210> SEQ ID NO 117
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 117

Glu Val Ile Glu Ala Trp Asn Glu Ile Asp Lys Leu Pro Asn Leu Thr
1               5                   10                  15

Leu Gln Gln Trp Leu Ala Phe Ile Asn Lys Leu Asp Asp
            20                  25

<210> SEQ ID NO 118
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 118

Glu Val Ile Asp Ala Asn Asp Glu Ile Asp Ala Leu Pro Asn Leu Thr
1               5                   10                  15

Ile Glu Gln Trp Leu Ala Phe Ile Asn Lys Leu His Asp
            20                  25

<210> SEQ ID NO 119
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 119

Glu Val Ile Ala Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 120
<211> LENGTH: 29
<212> TYPE: PRT
<213> ORGANISM: Artificial Sequence -continued

```
<220> FEATURE:
<223> OTHER INFORMATION: Modified bacterial sequence

<400> SEQUENCE: 120

Glu Val Ile Glu Ala Trp Thr Glu Ile Asp Gln Leu Pro Asn Leu Thr
1               5                   10                  15

Leu Asp Gln Trp Leu Ala Phe Ile Asn Lys Leu Asp Asp
            20                  25

<210> SEQ ID NO 121
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 121

Glu Val Ile Asn Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 122
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 122

Glu His Ile Glu Ala Trp Asp Glu Ile Asp His Leu Pro Asn Leu Thr
1               5                   10                  15

Ile Asp Gln Trp Leu Ala Phe Ile Asn Lys Leu Ala Asp
            20                  25

<210> SEQ ID NO 123
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 123

Glu His Leu Glu Ala Trp Arg Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 124
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 124

Glu Val Leu Asp Ala Trp Asn Glu Ile Asp Lys Leu Pro Asn Leu Thr
1               5                   10                  15

Leu Gln Gln Trp Leu Ala Phe Ile Asn Lys Leu Asp Asp
            20                  25

<210> SEQ ID NO 125
<211> LENGTH: 29
<212> TYPE: PRT
```

<213> ORGANISM: Artificial Sequence
<220> FEATURE:
<223> OTHER INFORMATION: Modified bacterial sequence

<400> SEQUENCE: 125

Glu Val Ile Ala Ala Trp Asp Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 126
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 126

Glu Val Ile Gln Ala Trp Asn Glu Ile Asp Ala Leu Pro Asn Leu Thr
1               5                   10                  15

Leu Glu Gln Trp Leu Ala Phe Ile Asn Lys Leu Asp Asp
            20                  25

<210> SEQ ID NO 127
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 127

Glu Val Ile Asp Ala Trp Asn Glu Ile Asp His Leu Pro Asn Leu Thr
1               5                   10                  15

Ile Ala Gln Trp Leu Ala Phe Ile Asn Lys Leu Asp Asp
            20                  25

<210> SEQ ID NO 128
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 128

Glu Gln Leu Asp Ala Trp Asp Glu Ile Asp His Leu Pro Asn Leu Thr
1               5                   10                  15

Ile Asp Gln Trp Leu Ala Phe Ile Asn Lys Leu Ser Asp
            20                  25

<210> SEQ ID NO 129
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 129

Glu Val Leu Asn Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 130
<211> LENGTH: 29

```
<212> TYPE: PRT
<213> ORGANISM: Artificial Sequence
<220> FEATURE:
<223> OTHER INFORMATION: Modified bacterial sequence

<400> SEQUENCE: 130

Glu Val Leu Glu Ala Trp Asn Glu Ile Asp His Leu Pro Asn Leu Thr
1               5                   10                  15

Ile Asp Gln Trp Leu Ala Phe Ile Asn Lys Leu Asp Asp
            20                  25

<210> SEQ ID NO 131
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 131

Glu Val Leu Leu Ala Trp Asp Glu Ile Asp Arg Leu Pro Asn Leu Thr
1               5                   10                  15

Ile Asp Gln Trp Leu Ala Phe Ile Asn Lys Leu Ala Asp
            20                  25

<210> SEQ ID NO 132
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 132

Glu Val Ile Ala Ala Trp Asn Glu Ile Asp Gln Leu Pro Asn Leu Thr
1               5                   10                  15

Leu Asp Gln Trp Leu Ala Phe Ile Asn Lys Leu Asp Asp
            20                  25

<210> SEQ ID NO 133
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 133

Glu Thr Leu Leu Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 134
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 134

Glu Val Ile Asp Ala Trp Asn Glu Ile Asp Thr Leu Pro Asn Leu Thr
1               5                   10                  15

Leu Glu Gln Trp Leu Ala Phe Ile Asn Lys Leu Asp Asp
            20                  25

<210> SEQ ID NO 135
```

```
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 135

Glu Val Leu His Ala Trp Asn Glu Ile Asp His Leu Pro Asn Leu Thr
1               5                   10                  15

Leu Asn Gln Trp Leu Ala Phe Ile Asn Lys Leu Gln Asp
                20                  25

<210> SEQ ID NO 136
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 136

Glu Val Ile Gln Ala Trp Asn Glu Ile Asp Ala Leu Pro Asn Leu Thr
1               5                   10                  15

Ile Ala Gln Trp Leu Ala Phe Ile Asn Lys Leu Asp Asp
                20                  25

<210> SEQ ID NO 137
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 137

Glu Thr Val Asp Ala Trp Asn Glu Ile Asp Ala Leu Pro Asn Leu Thr
1               5                   10                  15

Ile Glu Gln Trp Leu Ala Phe Ile Asn Lys Leu Asp Asp
                20                  25

<210> SEQ ID NO 138
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 138

Glu Val Ile Gln Ala Trp Asp Glu Ile Asp His Leu Pro Asn Leu Thr
1               5                   10                  15

Ile Asp Gln Trp Leu Ala Phe Ile Asn Lys Leu Asp Asp
                20                  25

<210> SEQ ID NO 139
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 139

Glu Val Leu Asp Ala Trp Asn Glu Ile Asp Gln Leu Pro Asn Leu Thr
1               5                   10                  15

Ile Gln Gln Trp Leu Ala Phe Ile Asn Lys Leu Asp Asp
                20                  25
```

-continued

```
<210> SEQ ID NO 140
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 140

Glu Thr Ile Glu Ala Trp Asn Glu Ile Asp Ala Leu Pro Asn Leu Thr
1               5                   10                  15

Leu Asp Gln Trp Leu Ala Phe Ile Asn Lys Leu Asp Asp
            20                  25

<210> SEQ ID NO 141
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 141

Glu Val Ile Glu Ala Trp Asp Glu Ile Asp Ala Leu Pro Asn Leu Thr
1               5                   10                  15

Ile Asp Gln Trp Leu Ala Phe Ile Asn Lys Leu Asp Asp
            20                  25

<210> SEQ ID NO 142
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 142

Glu Val Ile Glu Ala Trp Asn Glu Ile Asp Gln Leu Pro Asn Leu Thr
1               5                   10                  15

Ile Gln Gln Trp Leu Ala Phe Ile Asn Lys Leu Asp Asp
            20                  25

<210> SEQ ID NO 143
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 143

Glu Val Ile Glu Ala Trp Thr Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 144
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 144

Glu Val Ile Gln Ala Trp Asn Glu Ile Asp His Leu Pro Asn Leu Thr
1               5                   10                  15

Leu Gln Gln Trp Leu Ala Phe Ile Asn Lys Leu Glu Asp
            20                  25
```

<210> SEQ ID NO 145
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 145

Glu Val Ile Gln Ala Asn Asn Glu Ile Asp Gln Leu Pro Asn Leu Thr
1               5                   10                  15

Ile Glu Gln Trp Leu Ala Phe Ile Asn Lys Leu His Asp
            20                  25

<210> SEQ ID NO 146
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 146

Glu Val Leu His Ala Trp Ser Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 147
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 147

Glu Thr Ile Gln Ala Trp Asp Glu Ile Asp Lys Leu Pro Asn Leu Thr
1               5                   10                  15

Leu Asp Gln Trp Leu Ala Phe Ile Asn Lys Leu Ser Asp
            20                  25

<210> SEQ ID NO 148
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 148

Glu Thr Leu Arg Ala Trp Asp Glu Ile Asp Lys Leu Pro Asn Leu Thr
1               5                   10                  15

Ile Gln Gln Trp Leu Ala Phe Ile Asn Lys Leu Ala Asp
            20                  25

<210> SEQ ID NO 149
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 149

Glu Val Ile Asp Ala Trp Asn Glu Ile Asp His Leu Pro Asn Leu Thr
1               5                   10                  15

Ile Glu Gln Trp Leu Ala Phe Ile Asn Lys Leu Glu Asp
            20                  25

<210> SEQ ID NO 150
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 150

Glu Val Ile Asp Ala Trp Asn Glu Ile Asp His Leu Pro Asn Leu Thr
1               5                   10                  15

Leu Gln Gln Trp Leu Ala Phe Ile Asn Lys Leu Ala Asp
            20                  25

<210> SEQ ID NO 151
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 151

Glu Thr Ile Asp Ala Trp Asn Glu Ile Asp Ala Leu Pro Asn Leu Thr
1               5                   10                  15

Leu Asp Gln Trp Leu Ala Phe Ile Asn Lys Leu Asp Asp
            20                  25

<210> SEQ ID NO 152
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 152

Glu Val Ile Glu Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 153
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 153

Glu Val Ile Arg Ala Trp Asp Glu Ile Asp Gln Leu Pro Asn Leu Thr
1               5                   10                  15

Leu Ser Gln Trp Leu Ala Phe Ile Asn Lys Leu Asp Asp
            20                  25

<210> SEQ ID NO 154
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 154

Glu Val Ile Glu Ala Trp Asn Glu Ile Asp Arg Leu Pro Asn Leu Thr
1               5                   10                  15

Ile His Gln Trp Leu Ala Phe Ile Asn Lys Leu Asp Asp

-continued 20              25

<210> SEQ ID NO 155
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 155

Glu Thr Ile Glu Ala Trp Asn Glu Ile Asp Gln Leu Pro Asn Leu Thr
1               5                   10                  15

Ile Glu Gln Trp Leu Ala Phe Ile Asn Lys Leu Asp Asp
            20              25

<210> SEQ ID NO 156
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 156

Glu Val Leu Thr Ala Trp Ala Glu Ile Asp Ala Leu Pro Asn Leu Thr
1               5                   10                  15

Leu Ser Gln Trp Leu Ala Phe Ile Asn Lys Leu Asp Asp
            20              25

<210> SEQ ID NO 157
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 157

Glu Val Ile Glu Ala Trp Asp Glu Ile Asp Lys Leu Pro Asn Leu Thr
1               5                   10                  15

Val Asp Gln Trp Leu Ala Phe Ile Asn Lys Leu Asp Asp
            20              25

<210> SEQ ID NO 158
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 158

Glu Val Ile Asp Ala Trp Asn Glu Ile Asp His Leu Pro Asn Leu Thr
1               5                   10                  15

Leu Thr Gln Trp Leu Ala Phe Ile Asn Lys Leu Asp Asp
            20              25

<210> SEQ ID NO 159
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 159

Glu Val Ile Glu Ala Trp Asn Glu Ile Asp Gln Leu Pro Asn Leu Thr
1               5                   10                  15

Leu Asp Gln Trp Leu Ala Phe Ile Asn Lys Leu Asp Asp
            20                  25

<210> SEQ ID NO 160
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 160

Glu Thr Leu Gln Ala Trp Asp Glu Ile Asp His Leu Pro Asn Leu Thr
1               5                   10                  15

Leu Asn Gln Trp Leu Ala Phe Ile Asn Lys Leu Asp Asp
            20                  25

<210> SEQ ID NO 161
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 161

Glu Val Ile Asp Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 162
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 162

Glu Val Ile Glu Ala Trp Asn Glu Ile Asp Leu Leu Pro Asn Leu Thr
1               5                   10                  15

Leu Ser Gln Trp Leu Ala Phe Ile Asn Lys Leu Asp Asp
            20                  25

<210> SEQ ID NO 163
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 163

Glu Val Ile Asp Ala Trp Asp Glu Ile Asp Arg Leu Pro Asn Leu Thr
1               5                   10                  15

Leu Lys Gln Trp Leu Ala Phe Ile Asn Lys Leu Asp Asp
            20                  25

<210> SEQ ID NO 164
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 164

Glu Thr Leu His Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 165
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 165

Glu Val Ile Lys Ala Trp Asp Glu Ile Asp His Leu Pro Asn Leu Thr
1               5                   10                  15

Leu Asn Gln Trp Leu Ala Phe Ile Asn Lys Leu Asp Asp
            20                  25

<210> SEQ ID NO 166
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 166

Glu Val Ile Glu Ala Trp Asn Glu Ile Asp His Leu Pro Asn Leu Thr
1               5                   10                  15

Leu Ala Gln Trp Leu Ala Phe Ile Asn Lys Leu Asp Asp
            20                  25

<210> SEQ ID NO 167
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 167

Glu Val Ile Gln Ala Trp Asn Glu Ile Asp His Leu Pro Asn Leu Thr
1               5                   10                  15

Ile Asp Gln Trp Leu Ala Phe Ile Thr Lys Leu Glu Asp
            20                  25

<210> SEQ ID NO 168
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 168

Glu Val Ile Glu Ala Trp Asn Glu Ile Asp Arg Leu Pro Asn Leu Thr
1               5                   10                  15

Ile Lys Gln Trp Leu Ala Phe Ile Asn Lys Leu Asp Asp
            20                  25

<210> SEQ ID NO 169
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 169

Glu Val Ile Glu Ala Trp Asn Glu Ile Asp Ser Leu Pro Asn Leu Thr

```
1               5                   10                  15
Leu Gln Gln Trp Leu Ala Phe Ile Asn Lys Leu Asp Asp
            20                  25

<210> SEQ ID NO 170
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 170

Glu Thr Ile Asp Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 171
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 171

Glu Val Leu Glu Ala Trp Ala Glu Ile Asp Ala Leu Pro Asn Leu Thr
1               5                   10                  15

Ile Ala Gln Trp Leu Ala Phe Ile Asn Lys Leu Asp Asp
            20                  25

<210> SEQ ID NO 172
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 172

Glu Thr Ile Asp Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 173
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 173

Glu Thr Leu Lys Ala Trp Asp Glu Ile Asp Arg Leu Pro Asn Leu Thr
1               5                   10                  15

Leu Glu Gln Trp Leu Ala Phe Ile Asn Lys Leu Asp Asp
            20                  25

<210> SEQ ID NO 174
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 174
```

Glu Thr Ile Ala Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 175
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 175

Glu Val Leu Gln Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 176
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 176

Glu Val Ile Glu Ala Trp Ser Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 177
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 177

Glu Val Ile Asp Ala Trp Asn Glu Ile Asp Gly Leu Pro Asn Leu Thr
1               5                   10                  15

Ile Glu Gln Trp Leu Ala Phe Ile Asn Lys Leu Asp Asp
            20                  25

<210> SEQ ID NO 178
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 178

Glu Val Ile His Ala Trp Asn Glu Ile Asp His Leu Pro Asn Leu Thr
1               5                   10                  15

Leu Asn Gln Trp Leu Ala Phe Ile Asn Lys Leu Glu Asp
            20                  25

<210> SEQ ID NO 179
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 179

Glu Val Leu Asp Ala Trp Asn Glu Ile Asp Ser Leu Pro Asn Leu Thr
1               5                   10                  15

Leu Asp Gln Trp Leu Ala Phe Ile Asn Lys Leu Asp Asp
            20                  25

<210> SEQ ID NO 180
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 180

Glu Gln Ile Glu Ala Trp Asn Glu Ile Asp Arg Leu Pro Asn Leu Thr
1               5                   10                  15

Leu Glu Gln Trp Leu Ala Phe Ile Asn Lys Leu Asp Asp
            20                  25

<210> SEQ ID NO 181
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 181

Glu Val Val Asp Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 182
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 182

Glu Val Ile Glu Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 183
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 183

Glu Val Ile Glu Ala Asn Asp Glu Ile Asp Arg Leu Pro Asn Leu Thr
1               5                   10                  15

Ile Glu Gln Trp Leu Ala Phe Ile Asn Lys Leu His Asp
            20                  25

<210> SEQ ID NO 184
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 184

Glu Thr Leu Gln Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 185
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 185

Glu Val Ile Glu Ala Trp Asp Glu Ile Asp His Leu Pro Asn Leu Thr
1               5                   10                  15

Ile Asp Gln Trp Leu Ala Phe Ile Asn Lys Leu Ala Asp
            20                  25

<210> SEQ ID NO 186
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 186

Glu Thr Ile Asp Ala Trp Asn Glu Ile Asp His Leu Pro Asn Leu Thr
1               5                   10                  15

Leu Gln Gln Trp Leu Ala Phe Ile Asn Lys Leu Ala Asp
            20                  25

<210> SEQ ID NO 187
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 187

Glu Val Ile Asp Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 188
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 188

Glu Val Ile Glu Ala Trp Asn Glu Ile Asp Lys Leu Pro Asn Leu Thr
1               5                   10                  15

Leu Ala Gln Trp Leu Ala Phe Ile Asn Lys Leu Asp Asp
            20                  25

<210> SEQ ID NO 189
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 189

Glu Val Leu Gln Ala Trp Asp Glu Ile Asp Lys Leu Pro Asn Leu Thr
1               5                   10                  15

Ile Gln Gln Trp Leu Ala Phe Ile Asn Lys Leu Asp Asp
            20                  25

<210> SEQ ID NO 190
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 190

Glu Val Ile Ala Ala Trp Asn Glu Ile Asp Gly Leu Pro Asn Leu Thr
1               5                   10                  15

Leu Gln Gln Trp Leu Ala Phe Ile Asn Lys Leu Asp Asp
            20                  25

<210> SEQ ID NO 191
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 191

Glu Thr Leu Asn Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 192
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 192

Glu Val Leu Ser Ala Trp Asn Glu Ile Asp Gln Leu Pro Asn Leu Thr
1               5                   10                  15

Leu Glu Gln Trp Leu Ala Phe Ile Asn Lys Leu Asp Asp
            20                  25

<210> SEQ ID NO 193
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 193

Glu Thr Leu Glu Ala Trp Asp Glu Ile Asp His Leu Pro Asn Leu Thr
1               5                   10                  15

Leu His Gln Trp Leu Ala Phe Ile Asn Lys Leu Asp Asp
            20                  25

<210> SEQ ID NO 194
<211> LENGTH: 29
<212> TYPE: PRT
<213> ORGANISM: Artificial Sequence
<220> FEATURE:

<223> OTHER INFORMATION: Modified bacterial sequence

<400> SEQUENCE: 194

Glu Gln Ile Glu Ala Trp Asn Glu Ile Asp His Leu Pro Asn Leu Thr
1               5                   10                  15

Leu Gln Gln Trp Leu Ala Phe Ile Asn Lys Leu Ala Asp
            20                  25

<210> SEQ ID NO 195
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 195

Glu Val Val Glu Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 196
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 196

Glu Val Leu Glu Ala Trp Asn Glu Ile Asp Glu Leu Pro Asn Leu Thr
1               5                   10                  15

Ile Glu Gln Trp Leu Ala Phe Ile Asn Lys Leu Asp Asp
            20                  25

<210> SEQ ID NO 197
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 197

Glu Val Ile Asp Ala Trp Asn Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 198
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 198

Glu Thr Ile Asp Ala Trp Asp Glu Ile Asp Lys Leu Pro Asn Leu Thr
1               5                   10                  15

Leu Ser Gln Trp Leu Ala Phe Ile Asn Lys Leu Asp Asp
            20                  25

<210> SEQ ID NO 199
<211> LENGTH: 29
<212> TYPE: PRT
<213> ORGANISM: Artificial Sequence

```
<220> FEATURE:
<223> OTHER INFORMATION: Modified bacterial sequence

<400> SEQUENCE: 199

Glu Thr Ile Asp Ala Trp Asn Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 200
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 200

Glu Val Ile Gln Ala Trp Asp Glu Ile Asp Ala Leu Pro Asn Leu Thr
1               5                   10                  15

Leu Asn Gln Trp Leu Ala Phe Ile Asn Lys Leu Asp Asp
            20                  25

<210> SEQ ID NO 201
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 201

Glu Val Leu Asp Ala Trp Ala Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 202
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 202

Glu His Ile Ala Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 203
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 203

Glu Val Ile Arg Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 204
<211> LENGTH: 29
<212> TYPE: PRT
```

<213> ORGANISM: Artificial Sequence
<220> FEATURE:
<223> OTHER INFORMATION: Modified bacterial sequence

<400> SEQUENCE: 204

Glu Val Ile Asp Ala Trp Asp Glu Ile Asp Ala Leu Pro Asn Leu Thr
1               5                   10                  15

Ile Asp Gln Trp Leu Ala Phe Ile Asn Lys Leu Ala Asp
            20                  25

<210> SEQ ID NO 205
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 205

Glu Val Ile Asp Ala Trp Asn Glu Ile Asp Arg Leu Pro Asn Leu Thr
1               5                   10                  15

Ile Gln Gln Trp Leu Ala Phe Ile Asn Lys Leu Asp Asp
            20                  25

<210> SEQ ID NO 206
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 206

Glu Val Ile Thr Ala Trp Asn Glu Ile Asp His Leu Pro Asn Leu Thr
1               5                   10                  15

Leu Ser Gln Trp Leu Ala Phe Ile Asn Lys Leu Asp Asp
            20                  25

<210> SEQ ID NO 207
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 207

Glu Val Ile Asp Ala Trp Asn Glu Ile Asp Ala Leu Pro Asn Leu Thr
1               5                   10                  15

Ile His Gln Trp Leu Ala Phe Ile Asn Lys Leu Asp Asp
            20                  25

<210> SEQ ID NO 208
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 208

Glu Gln Leu Lys Ala Trp Asp Glu Ile Asp Lys Leu Pro Asn Leu Thr
1               5                   10                  15

Ile Glu Gln Trp Leu Ala Phe Ile Glu Lys Leu Gln Asp
            20                  25

<210> SEQ ID NO 209
<211> LENGTH: 29

<212> TYPE: PRT
<213> ORGANISM: Artificial Sequence
<220> FEATURE:
<223> OTHER INFORMATION: Modified bacterial sequence

<400> SEQUENCE: 209

Glu His Ile Asp Ala Trp Thr Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 210
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 210

Glu Gln Leu Arg Ala Trp Asp Glu Ile Asp Lys Leu Pro Asn Leu Thr
1               5                   10                  15

Ile Glu Gln Trp Leu Ala Phe Ile Asn Lys Leu Gln Asp
            20                  25

<210> SEQ ID NO 211
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 211

Glu Val Leu Glu Ala Trp Arg Glu Ile Asp Ser Leu Pro Asn Leu Thr
1               5                   10                  15

Ile Ala Gln Trp Leu Ala Phe Ile Asn Lys Leu Asp Asp
            20                  25

<210> SEQ ID NO 212
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 212

Glu Val Ile Gln Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 213
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 213

Glu His Val Glu Ala Trp Asn Glu Ile Asp Gln Leu Pro Asn Leu Thr
1               5                   10                  15

Ile Glu Gln Trp Leu Ala Phe Ile Asn Lys Leu Ala Asp
            20                  25

<210> SEQ ID NO 214

```
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 214

Glu Val Ile Asp Ala Trp Asp Glu Ile Asp Ala Leu Pro Asn Leu Thr
1               5                   10                  15

Ile Asp Gln Trp Leu Ala Phe Ile Asn Lys Leu Ser Asp
            20                  25

<210> SEQ ID NO 215
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 215

Glu Val Ile Glu Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 216
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 216

Glu Val Leu Gln Ala Trp Asp Glu Ile Asp Lys Leu Pro Asn Leu Thr
1               5                   10                  15

Ile Glu Gln Trp Leu Ala Phe Ile Asn Lys Leu Ser Asp
            20                  25

<210> SEQ ID NO 217
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 217

Glu Val Ile Lys Ala Trp Asn Glu Ile Asp Ser Leu Pro Asn Leu Thr
1               5                   10                  15

Ile Glu Gln Trp Leu Ala Phe Ile Asn Lys Leu Asp Asp
            20                  25

<210> SEQ ID NO 218
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 218

Glu Val Leu Glu Ala Trp His Glu Ile Asp Leu Leu Pro Asn Leu Thr
1               5                   10                  15

Ile Gln Gln Trp Leu Ala Phe Ile Asn Lys Leu Asp Asp
            20                  25
```

```
<210> SEQ ID NO 219
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 219

Glu Val Leu Glu Ala Trp Thr Glu Ile Asp Arg Leu Pro Asn Leu Thr
1               5                   10                  15

Leu Asp Gln Trp Leu Ala Phe Ile Asn Lys Leu Asp Asp
            20                  25

<210> SEQ ID NO 220
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 220

Glu Gln Leu Tyr Ala Trp Asn Glu Ile Asp His Leu Pro Asn Leu Thr
1               5                   10                  15

Ile Glu Gln Trp Leu Ala Phe Ile Glu Lys Leu Gln Asp
            20                  25

<210> SEQ ID NO 221
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 221

Glu Val Leu Asn Ala Trp Asp Glu Ile Asp Lys Leu Pro Asn Leu Thr
1               5                   10                  15

Ile Lys Gln Trp Leu Ala Phe Ile Asn Lys Leu Asp Asp
            20                  25

<210> SEQ ID NO 222
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 222

Glu Val Ile Arg Ala Trp Asp Glu Ile Asp Lys Leu Pro Asn Leu Thr
1               5                   10                  15

Val Glu Gln Trp Leu Ala Phe Ile Asn Lys Leu Asp Asp
            20                  25

<210> SEQ ID NO 223
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 223

Glu Val Val Gln Ala Trp Asp Glu Ile Asp Gln Leu Pro Asn Leu Thr
1               5                   10                  15

Leu Glu Gln Trp Leu Ala Phe Ile Asn Lys Leu Asp Asp
            20                  25
```

<210> SEQ ID NO 224
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 224

Glu Val Ile Arg Ala Trp Asp Glu Ile Asp Gln Leu Pro Asn Leu Thr
1               5                   10                  15

Leu Glu Gln Trp Leu Ala Phe Ile Asn Lys Leu Asp Asp
            20                  25

<210> SEQ ID NO 225
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 225

Glu Thr Ile Asp Ala Trp Asn Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 226
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 226

Glu Val Val Ala Ala Trp Thr Glu Ile Asp Leu Leu Pro Asn Leu Thr
1               5                   10                  15

Leu Asp Gln Trp Leu Ala Phe Ile Asn Lys Leu Glu Asp
            20                  25

<210> SEQ ID NO 227
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 227

Glu Val Val Ala Ala Trp Asp Glu Ile Asp Ala Leu Pro Asn Leu Thr
1               5                   10                  15

Ile Glu Gln Trp Leu Ala Phe Ile Asn Lys Leu Ser Asp
            20                  25

<210> SEQ ID NO 228
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 228

Glu Thr Leu Glu Ala Trp Arg Glu Ile Asp Ser Leu Pro Asn Leu Thr
1               5                   10                  15

Leu Glu Gln Trp Leu Ala Phe Ile Asn Lys Leu Asp Asp
            20                  25

<210> SEQ ID NO 229
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 229

Glu Val Ile Lys Ala Trp Asn Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 230
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 230

Glu Val Leu Glu Ala Trp Thr Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 231
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 231

Glu Thr Leu Glu Ala Trp Asp Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 232
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 232

Glu Val Ile Glu Ala Trp Asn Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 233
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 233

Glu Thr Ile Asp Ala Trp Asn Glu Ile Asp Lys Leu Pro Asn Leu Thr
1               5                   10                  15

Leu Glu Gln Trp Leu Ala Phe Ile Asn Lys Leu Asp Asp

<210> SEQ ID NO 234
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 234

Glu Thr Leu Asp Ala Trp Asp Glu Ile Asp Ala Leu Pro Asn Leu Thr
1               5                   10                  15

Ile Asp Gln Trp Leu Ala Phe Ile Asn Lys Leu Glu Asp
            20                  25

<210> SEQ ID NO 235
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 235

Glu Val Leu Ser Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 236
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 236

Glu Val Ile Gln Ala Asn Asp Glu Ile Asp Lys Leu Pro Asn Leu Thr
1               5                   10                  15

Ile Glu Gln Trp Leu Ala Phe Ile His Lys Leu His Asp
            20                  25

<210> SEQ ID NO 237
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 237

Glu His Leu Asp Ala Trp Asp Glu Ile Asp His Leu Pro Asn Leu Thr
1               5                   10                  15

Ile Gln Gln Trp Leu Ala Phe Ile Asn Lys Leu Ala Asp
            20                  25

<210> SEQ ID NO 238
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 238

Glu Val Ile Gln Ala Trp Asn Glu Ile Asp Gln Leu Pro Asn Leu Thr
1               5                   10                  15

```
Ile Glu Gln Trp Leu Ala Phe Ile Asn Lys Leu Asp Asp
            20                  25

<210> SEQ ID NO 239
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 239

Glu Val Ile Glu Ala Trp Asn Glu Ile Asp Tyr Leu Pro Asn Leu Thr
1               5                   10                  15

Ile Ala Gln Trp Ile Ala Phe Ile Asn Lys Leu Asp Asp
            20                  25

<210> SEQ ID NO 240
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 240

Glu Thr Ile Gln Ala Trp Asp Glu Ile Asp Arg Leu Pro Asn Leu Thr
1               5                   10                  15

Leu Gln Gln Trp Leu Ala Phe Ile Asn Lys Leu Asp Asp
            20                  25

<210> SEQ ID NO 241
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 241

Glu Thr Ile Gln Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 242
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 242

Glu Thr Leu Asp Ala Trp Ala Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 243
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 243

Glu Val Ile Glu Ala Trp Asp Glu Ile Asp Lys Leu Pro Asn Leu Thr
1               5                   10                  15
```

Leu Asn Gln Trp Leu Ala Phe Ile Asn Lys Leu Asp Asp
            20                  25

<210> SEQ ID NO 244
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 244

Glu Val Leu Asp Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 245
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 245

Glu Val Leu His Ala Trp Asn Glu Ile Asp His Leu Pro Asn Leu Thr
1               5                   10                  15

Ile Glu Gln Trp Leu Ala Phe Ile Glu Lys Leu Glu Asp
            20                  25

<210> SEQ ID NO 246
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 246

Glu Val Ile Glu Ala Trp Gln Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 247
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 247

Glu Val Val Asp Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 248
<211> LENGTH: 29
<212> TYPE: PRT
<213> ORGANISM: Artificial Sequence
<220> FEATURE:
<223> OTHER INFORMATION: Modified bacterial sequence

<400> SEQUENCE: 248

Glu Gln Ile Glu Ala Trp Asn Glu Ile Asp Ala Leu Pro Asn Leu Thr

```
1               5                   10                  15
Ile Glu Gln Trp Leu Ala Phe Ile Asn Lys Leu Ala Asp
                20                  25

<210> SEQ ID NO 249
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 249

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys Val Asp Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 250
<211> LENGTH: 46
<212> TYPE: PRT
<213> ORGANISM: Artificial Sequence
<220> FEATURE:
<223> OTHER INFORMATION: Modified bacterial sequence

<400> SEQUENCE: 250

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 251
<211> LENGTH: 1676
<212> TYPE: PRT
<213> ORGANISM: Homo sapiens

<400> SEQUENCE: 251

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
            35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
```

-continued

```
                85                  90                  95
Asn Pro Val Ser Tyr Val Tyr Leu Glu Val Ser Lys His Phe Ser
            100                 105                 110

Lys Ser Lys Arg Met Pro Ile Thr Tyr Asp Asn Gly Phe Leu Phe Ile
            115                 120                 125

His Thr Asp Lys Pro Val Tyr Thr Pro Asp Gln Ser Val Lys Val Arg
            130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
                180                 185                 190

Asn Pro Arg Tyr Gly Met Trp Thr Ile Lys Ala Lys Tyr Lys Glu Asp
                195                 200                 205

Phe Ser Thr Thr Gly Thr Ala Tyr Phe Glu Val Lys Glu Tyr Val Leu
                210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
                260                 265                 270

Glu Asp Leu Lys Asp Asp Gln Lys Glu Met Met Gln Thr Ala Met Gln
                275                 280                 285

Asn Thr Met Leu Ile Asn Gly Ile Ala Gln Val Thr Phe Asp Ser Glu
                290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
                340                 345                 350

Lys Leu Asn Leu Val Ala Thr Pro Leu Phe Leu Lys Pro Gly Ile Pro
                355                 360                 365

Tyr Pro Ile Lys Val Gln Val Lys Asp Ser Leu Asp Gln Leu Val Gly
                370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
                420                 425                 430

Phe Asn Val Lys Thr Asp Ala Pro Asp Leu Pro Glu Glu Asn Gln Ala
                435                 440                 445

Arg Glu Gly Tyr Arg Ala Ile Ala Tyr Ser Ser Leu Ser Gln Ser Tyr
                450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
                500                 505                 510
```

```
Gly Thr Arg Glu Lys Phe Ser Asp Ala Ser Tyr Gln Ser Ile Asn Ile
            515                 520                 525

Pro Val Thr Gln Asn Met Val Pro Ser Ser Arg Leu Leu Val Tyr Tyr
530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
        595                 600                 605

Val Tyr Gly Val Gln Arg Gly Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
        675                 680                 685

Lys Tyr Lys His Ser Val Val Lys Cys Cys Tyr Asp Gly Ala Cys
    690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
    770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Ser Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
        915                 920                 925
```

```
Val Val Pro Glu Gly Val Lys Arg Glu Ser Tyr Ser Gly Val Thr Leu
    930             935             940

Asp Pro Arg Gly Ile Tyr Gly Thr Ile Ser Arg Arg Lys Glu Phe Pro
945             950             955             960

Tyr Arg Ile Pro Leu Asp Leu Val Pro Lys Thr Glu Ile Lys Arg Ile
            965             970             975

Leu Ser Val Lys Gly Leu Leu Val Gly Glu Ile Leu Ser Ala Val Leu
            980             985             990

Ser Gln Glu Gly Ile Asn Ile Leu Thr His Leu Pro Lys Gly Ser Ala
            995             1000            1005

Glu Ala Glu Leu Met Ser Val Pro Val Phe Tyr Val Phe His
    1010            1015            1020

Tyr Leu Glu Thr Gly Asn His Trp Asn Ile Phe His Ser Asp Pro
    1025            1030            1035

Leu Ile Glu Lys Gln Lys Leu Lys Lys Lys Leu Lys Glu Gly Met
    1040            1045            1050

Leu Ser Ile Met Ser Tyr Arg Asn Ala Asp Tyr Ser Tyr Ser Val
    1055            1060            1065

Trp Lys Gly Gly Ser Ala Ser Thr Trp Leu Thr Ala Phe Ala Leu
    1070            1075            1080

Arg Val Leu Gly Gln Val Asn Lys Tyr Val Glu Gln Asn Gln Asn
    1085            1090            1095

Ser Ile Cys Asn Ser Leu Leu Trp Leu Val Glu Asn Tyr Gln Leu
    1100            1105            1110

Asp Asn Gly Ser Phe Lys Glu Asn Ser Gln Tyr Gln Pro Ile Lys
    1115            1120            1125

Leu Gln Gly Thr Leu Pro Val Glu Ala Arg Glu Asn Ser Leu Tyr
    1130            1135            1140

Leu Thr Ala Phe Thr Val Ile Gly Ile Arg Lys Ala Phe Asp Ile
    1145            1150            1155

Cys Pro Leu Val Lys Ile Asp Thr Ala Leu Ile Lys Ala Asp Asn
    1160            1165            1170

Phe Leu Leu Glu Asn Thr Leu Pro Ala Gln Ser Thr Phe Thr Leu
    1175            1180            1185

Ala Ile Ser Ala Tyr Ala Leu Ser Leu Gly Asp Lys Thr His Pro
    1190            1195            1200

Gln Phe Arg Ser Ile Val Ser Ala Leu Lys Arg Glu Ala Leu Val
    1205            1210            1215

Lys Gly Asn Pro Pro Ile Tyr Arg Phe Trp Lys Asp Asn Leu Gln
    1220            1225            1230

His Lys Asp Ser Ser Val Pro Asn Thr Gly Thr Ala Arg Met Val
    1235            1240            1245

Glu Thr Thr Ala Tyr Ala Leu Leu Thr Ser Leu Asn Leu Lys Asp
    1250            1255            1260

Ile Asn Tyr Val Asn Pro Val Ile Lys Trp Leu Ser Glu Glu Gln
    1265            1270            1275

Arg Tyr Gly Gly Gly Phe Tyr Ser Thr Gln Asp Thr Ile Asn Ala
    1280            1285            1290

Ile Glu Gly Leu Thr Glu Tyr Ser Leu Leu Val Lys Gln Leu Arg
    1295            1300            1305

Leu Ser Met Asp Ile Asp Val Ser Tyr Lys His Lys Gly Ala Leu
    1310            1315            1320

His Asn Tyr Lys Met Thr Asp Lys Asn Phe Leu Gly Arg Pro Val
```

1325                1330                1335
Glu Val Leu Leu Asn Asp Asp Leu Ile Val Ser Thr Gly Phe Gly
    1340                1345                1350

Ser Gly Leu Ala Thr Val His Val Thr Thr Val His Lys Thr
    1355                1360                1365

Ser Thr Ser Glu Glu Val Cys Ser Phe Tyr Leu Lys Ile Asp Thr
    1370                1375                1380

Gln Asp Ile Glu Ala Ser His Tyr Arg Gly Tyr Gly Asn Ser Asp
    1385                1390                1395

Tyr Lys Arg Ile Val Ala Cys Ala Ser Tyr Lys Pro Ser Arg Glu
    1400                1405                1410

Glu Ser Ser Ser Gly Ser Ser His Ala Val Met Asp Ile Ser Leu
    1415                1420                1425

Pro Thr Gly Ile Ser Ala Asn Glu Glu Asp Leu Lys Ala Leu Val
    1430                1435                1440

Glu Gly Val Asp Gln Leu Phe Thr Asp Tyr Gln Ile Lys Asp Gly
    1445                1450                1455

His Val Ile Leu Gln Leu Asn Ser Ile Pro Ser Ser Asp Phe Leu
    1460                1465                1470

Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515

Val Cys Glu Gly Ala Ala Cys Lys Cys Val Glu Ala Asp Cys Gly
    1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 252
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 252

```
Ala Glu Ala Lys Tyr Ala Lys Glu Val Leu Glu Ala Trp Asp Glu Ile
1               5                   10                  15
Asp Arg Leu Pro Asn Leu Thr Ile Glu Gln Trp Leu Ala Phe Ile Asn
            20                  25                  30
Lys Leu Asp Arg Gln Pro Glu Gln Ser Ser Glu Leu Leu Ser Glu Ala
        35                  40                  45
Lys Lys Leu Asn Asp Ser Gln Ala Pro Lys Val Asp Gly Ser Leu Ala
50                  55                  60
Glu Ala Lys Glu Ala Ala Asn Ala Glu Leu Asp Ser Tyr Gly Val Ser
65                  70                  75                  80
Asp Phe Tyr Lys Arg Leu Ile Asp Lys Ala Lys Thr Val Glu Gly Val
                85                  90                  95
Glu Ala Leu Lys Asp Ala Ile Leu Ala Ala Leu Pro
            100                 105
```

<210> SEQ ID NO 253
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 253

```
Ala Glu Ala Lys Tyr Ala Lys Glu Val Leu Glu Ala Trp Asp Glu Ile
1               5                   10                  15
Asp Arg Leu Pro Asn Leu Thr Ile Glu Gln Trp Leu Ala Phe Ile Asn
            20                  25                  30
Lys Leu Asp Asp Pro Ser Gln Ser Ser Glu Leu Leu Ser Glu Ala
        35                  40                  45
Lys Lys Leu Ser Glu Ser Gln Ala Pro Lys Val Asp Gly Ser Leu Ala
50                  55                  60
Glu Ala Lys Glu Ala Ala Asn Ala Glu Leu Asp Ser Tyr Gly Val Ser
65                  70                  75                  80
Asp Phe Tyr Lys Arg Leu Ile Asp Lys Ala Lys Thr Val Glu Gly Val
                85                  90                  95
Glu Ala Leu Lys Asp Ala Ile Leu Ala Ala Leu Pro
            100                 105
```

<210> SEQ ID NO 254
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 254

```
Ala Glu Ala Lys Tyr Ala Lys Glu Val Leu Glu Ala Trp Asp Glu Ile
1               5                   10                  15
Asp Arg Leu Pro Asn Leu Thr Ile Glu Gln Trp Leu Ala Phe Ile Asn
            20                  25                  30
Lys Leu Asp Asp Pro Ser Gln Ser Ser Glu Leu Leu Ser Glu Ala
        35                  40                  45
Lys Lys Leu Asn Asp Ser Gln Ala Pro Lys Val Asp Gly Ser Leu Ala
50                  55                  60
Glu Ala Lys Val Leu Ala Asn Arg Glu Leu Asp Lys Tyr Gly Val Ser
65                  70                  75                  80
```

```
Asp Phe Tyr Lys Arg Leu Ile Asn Lys Ala Lys Thr Val Glu Gly Val
                85                  90                  95

Glu Ala Leu Lys Leu His Ile Leu Ala Ala Leu Pro
            100                 105

<210> SEQ ID NO 255
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 255

Ala Glu Ala Lys Tyr Ala Lys Glu Val Leu Glu Ala Trp Ser Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 256
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 256

Ala Glu Ala Lys Tyr Ala Lys Glu Val Leu Glu Ala Trp Asp Glu Ile
1               5                   10                  15

Glu Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 257
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 257

Ala Glu Ala Lys Tyr Ala Lys Glu Val Leu Glu Ala Trp Asp Glu Ile
```

```
                1               5                  10                  15
Asp Arg Leu Pro Asn Leu Thr Ile Glu Gln Trp Leu Ala Phe Ile Ala
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys Val Asp Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 258
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 258

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Glu Asp Asp Pro Ser Gln Ser Ser Glu Leu Leu Ser Glu Ala
            35                  40                  45

Lys Lys Leu Asn Asp Ser Gln Ala Pro Lys Val Asp Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105

<210> SEQ ID NO 259
<211> LENGTH: 103
<212> TYPE: PRT
<213> ORGANISM: Artificial Sequence
<220> FEATURE:
<223> OTHER INFORMATION: Modified bacterial sequence

<400> SEQUENCE: 259

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Leu Ala Glu Ala Lys Glu Ala
        50                  55                  60

Ala Asn Ala Glu Leu Asp Ser Tyr Gly Val Ser Asp Phe Tyr Lys Arg
65                  70                  75                  80

Leu Ile Asp Lys Ala Lys Thr Val Glu Gly Val Glu Ala Leu Lys Asp
                85                  90                  95
```

```
Ala Ile Leu Ala Ala Leu Pro
            100
```

<210> SEQ ID NO 260
<211> LENGTH: 57
<212> TYPE: PRT
<213> ORGANISM: Artificial Sequence
<220> FEATURE:
<223> OTHER INFORMATION: Modified bacterial sequence

<400> SEQUENCE: 260

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Ser Glu Ser Gln Ala Pro
    50                  55
```

<210> SEQ ID NO 261
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 261

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Ser Glu Ser Gln Ala Pro Lys Val Glu Gly Ser Leu Ala
    50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

<210> SEQ ID NO 262
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 262

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Ser Glu Ser Gln Ala Pro Lys Val Ala Gly Ser Leu Ala
    50                  55                  60

Glu Ala Lys Glu Ala Ala Asn Ala Glu Leu Asp Ser Tyr Gly Val Ser
```

```
                65                  70                  75                  80
Asp Phe Tyr Lys Arg Leu Ile Asp Lys Ala Lys Thr Val Glu Gly Val
                    85                  90                  95

Glu Ala Leu Lys Asp Ala Ile Leu Ala Ala Leu Pro
                100                 105

<210> SEQ ID NO 263
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 263

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Glu Leu Leu Ser Glu Ala
            35                  40                  45

Lys Lys Leu Glu Ser Ser Gln Ala Pro Lys Val Glu Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
                100                 105

<210> SEQ ID NO 264
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 264

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Arg Gln Pro Glu Gln Ser Ser Glu Leu Leu Ser Glu Ala
            35                  40                  45

Lys Lys Leu Ser Glu Ser Gln Ala Pro Lys Val Glu Gly Ser Leu Ala
        50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
                100                 105

<210> SEQ ID NO 265
<211> LENGTH: 57
<212> TYPE: PRT
<213> ORGANISM: Artificial Sequence
<220> FEATURE:
<223> OTHER INFORMATION: Modified bacterial sequence

<400> SEQUENCE: 265
```

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Glu Ser Ser Gln Ala Pro
    50                  55

<210> SEQ ID NO 266
<211> LENGTH: 57
<212> TYPE: PRT
<213> ORGANISM: Artificial Sequence
<220> FEATURE:
<223> OTHER INFORMATION: Modified bacterial sequence

<400> SEQUENCE: 266

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Arg Gln Pro Glu Gln Ser Ser Glu Leu Leu Ser Glu Ala
        35                  40                  45

Lys Lys Leu Ser Glu Ser Gln Ala Pro
    50                  55

<210> SEQ ID NO 267
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 267

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 268
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 268

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Glu Gly Ser Leu Ala
    50                  55                  60

```
Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

<210> SEQ ID NO 269
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 269

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Glu Ser Gln Ala Pro Lys Val Glu Gly Ser Leu Ala
50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

<210> SEQ ID NO 270
<211> LENGTH: 108
<212> TYPE: PRT
<213> ORGANISM: Artificial Sequence
<220> FEATURE:
<223> OTHER INFORMATION: Modified bacterial sequence

<400> SEQUENCE: 270

```
Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Ser Asp Ser Gln Ala Pro Lys Val Glu Gly Ser Leu Ala
50                  55                  60

Glu Ala Lys Glu Ala Ala Asn Ala Glu Leu Asp Ser Tyr Gly Val Ser
65                  70                  75                  80

Asp Phe Tyr Lys Arg Leu Ile Asp Lys Ala Lys Thr Val Glu Gly Val
                85                  90                  95

Glu Ala Leu Lys Asp Ala Ile Leu Ala Ala Leu Pro
            100                 105
```

<210> SEQ ID NO 271
<211> LENGTH: 62
<212> TYPE: PRT
<213> ORGANISM: Artificial Sequence
<220> FEATURE:
<223> OTHER INFORMATION: Modified bacterial sequence

```
<400> SEQUENCE: 271

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp Gly Ser
    50                  55                  60

<210> SEQ ID NO 272
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 272

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 273
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 273

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 274
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 274

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Arg Gln Pro Glu Gln Ser Ser Glu Leu Leu Ser Glu Ala
        35                  40                  45

Lys Lys Leu Ser Glu Ser Gln Ala Pro Lys
    50                  55
```

<210> SEQ ID NO 275
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 275

Ala Glu Ala Lys Tyr Ala Lys Glu Leu Ile Glu Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 276
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 276

Ala Glu Ala Lys Tyr Ala Lys Glu Leu Ile Glu Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 277
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 277

Ala Glu Ala Lys Tyr Ala Lys Glu Leu Ile Glu Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Arg Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 278
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 278

Ala Glu Ala Lys Tyr Ala Lys Glu Gln Asp Ala Ala Ala His Glu Ile
1               5                   10                  15

-continued

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 279
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 279

Ala Glu Ala Lys Tyr Ala Lys Glu Gln Asp Ala Ala His Glu Ile
1               5                   10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 280
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 280

Ala Glu Ala Lys Tyr Ala Lys Glu Gln Asp Ala Ala His Glu Ile
1               5                   10                  15

Arg Trp Leu Pro Asn Leu Thr Phe Asp Gln Arg Val Ala Phe Ile His
            20                  25                  30

Lys Leu Ala Arg Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 281
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 281

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 282
<211> LENGTH: 58

```
<212> TYPE: PRT
<213> ORGANISM: Artificial Sequence
<220> FEATURE:
<223> OTHER INFORMATION: Modified bacterial sequence

<400> SEQUENCE: 282

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Ser Glu Ser Gln Ala Pro Lys
    50                  55

<210> SEQ ID NO 283
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 283

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Arg Gln Pro Glu Gln Ser Ser Glu Leu Leu Ser Glu Ala
        35                  40                  45

Lys Lys Leu Ser Glu Ser Gln Ala Pro Lys
    50                  55

<210> SEQ ID NO 284
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 284

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
        35                  40                  45

Lys Lys Leu Asn Glu Ser Gln Ala Pro Lys
    50                  55

<210> SEQ ID NO 285
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 285

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30
```

Lys Leu Trp Arg Gln Pro Glu Gln Ser Ser Glu Leu Leu Ser Glu Ala
                35                  40                  45

Lys Lys Leu Asn Glu Ser Gln Ala Pro Lys
    50                  55

<210> SEQ ID NO 286
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 286

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Asp Asp Pro Ser Gln Ser Ser Glu Leu Leu Ser Glu Ala
                35                  40                  45

Lys Lys Leu Ser Asp Ser Gln Ala Pro Lys
    50                  55

<210> SEQ ID NO 287
<211> LENGTH: 58
<212> TYPE: PRT
<213> ORGANISM: Artificial Sequence
<220> FEATURE:
<223> OTHER INFORMATION: Modified bacterial sequence

<400> SEQUENCE: 287

Ala Glu Ala Lys Tyr Ala Lys Glu Asn Leu Phe Ala Gly Trp Glu Ile
1               5                   10                  15

Ser Asp Leu Pro Asn Leu Thr Asp Tyr Gln Arg Asn Ala Phe Ile Tyr
            20                  25                  30

Lys Leu Trp Arg Gln Pro Glu Gln Ser Ser Glu Leu Leu Ser Glu Ala
                35                  40                  45

Lys Lys Leu Ser Asp Ser Gln Ala Pro Lys
    50                  55

<210> SEQ ID NO 288
<211> LENGTH: 29
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (2)..(2)
<223> OTHER INFORMATION: Xaa is selected from H, Q, S, T, and V
<220> FEATURE:
<221> NAME/KEY: MISC_FEATURE
<222> LOCATION: (3)..(3)
<223> OTHER INFORMATION: Xaa is selected from I, L, M, and V
<220> FEATURE:
<221> NAME/KEY: MISC_FEATURE
<222> LOCATION: (4)..(4)
<223> OTHER INFORMATION: Xaa is selected from A, D, E, H, K, L, N, Q, R,
     S, T, and Y
<220> FEATURE:
<221> NAME/KEY: MISC_FEATURE
<222> LOCATION: (6)..(6)
<223> OTHER INFORMATION: Xaa is selected from N and W
<220> FEATURE:
<221> NAME/KEY: MISC_FEATURE
<222> LOCATION: (7)..(7)
<223> OTHER INFORMATION: Xaa is selected from A, D, E, H, N, Q, R, S,
     and T

```
<220> FEATURE:
<221> NAME/KEY: MISC_FEATURE
<222> LOCATION: (11)..(11)
<223> OTHER INFORMATION: Xaa is selected from A, E, G, H, K, L, Q, R, S,
      T, and Y
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from I, L, and V
<220> FEATURE:
<221> NAME/KEY: MISC_FEATURE
<222> LOCATION: (18)..(18)
<223> OTHER INFORMATION: Xaa is selected from A, D, E, H, K, N, Q, R, S
      and T
<220> FEATURE:
<221> NAME/KEY: MISC_FEATURE
<222> LOCATION: (21)..(21)
<223> OTHER INFORMATION: Xaa is selected from I, L, and V
<220> FEATURE:
<221> NAME/KEY: MISC_FEATURE
<222> LOCATION: (25)..(25)
<223> OTHER INFORMATION: Xaa is selected from D, E, G, H, N, S, and T
<220> FEATURE:
<221> NAME/KEY: MISC_FEATURE
<222> LOCATION: (26)..(26)
<223> OTHER INFORMATION: Xaa is selected from K and S
<220> FEATURE:
<221> NAME/KEY: MISC_FEATURE
<222> LOCATION: (28)..(28)
<223> OTHER INFORMATION: Xaa is selected from A, D, E, H, N, Q, S, T,
      and Y

<400> SEQUENCE: 288

Glu Xaa Xaa Xaa Ala Xaa Xaa Glu Ile Asp Xaa Leu Pro Asn Leu Xaa
1               5                   10                  15

Xaa Xaa Gln Trp Xaa Ala Phe Ile Xaa Xaa Leu Xaa Asp
            20                  25

<210> SEQ ID NO 289
<211> LENGTH: 16
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (1)..(1)
<223> OTHER INFORMATION: a C5 binding motif
<220> FEATURE:
<221> NAME/KEY: MISC_FEATURE
<222> LOCATION: (1)..(1)
<223> OTHER INFORMATION: an interconnecting loop selected from DDPS and
      RQPE
<220> FEATURE:
<221> NAME/KEY: MISC_FEATURE
<222> LOCATION: (3)..(3)
<223> OTHER INFORMATION: Xaa is selected from A and S
<220> FEATURE:
<221> NAME/KEY: MISC_FEATURE
<222> LOCATION: (4)..(4)
<223> OTHER INFORMATION: Xaa is selected from N and E
<220> FEATURE:
<221> NAME/KEY: MISC_FEATURE
<222> LOCATION: (7)..(7)
<223> OTHER INFORMATION: Xaa is selected from A, S, and C
<220> FEATURE:
<221> NAME/KEY: MISC_FEATURE
<222> LOCATION: (13)..(13)
<223> OTHER INFORMATION: Xaa is selected from E, N, and S
<220> FEATURE:
<221> NAME/KEY: MISC_FEATURE
<222> LOCATION: (14)..(14)
```

```
<223> OTHER INFORMATION: Xaa is selected from D, E, and S
<220> FEATURE:
<221> NAME/KEY: MISC_FEATURE
<222> LOCATION: (15)..(15)
<223> OTHER INFORMATION: Xaa is selected from A and S

<400> SEQUENCE: 289

Gln Ser Xaa Xaa Leu Leu Xaa Glu Ala Lys Lys Leu Xaa Xaa Xaa Gln
1               5                   10                  15

<210> SEQ ID NO 290
<211> LENGTH: 25
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (7)..(8)
<223> OTHER INFORMATION: a C5 binding motif
<220> FEATURE:
<221> NAME/KEY: MISC_FEATURE
<222> LOCATION: (7)..(8)
<223> OTHER INFORMATION: an interconnecting loop selected from DDPS and
      RQPE
<220> FEATURE:
<221> NAME/KEY: MISC_FEATURE
<222> LOCATION: (10)..(10)
<223> OTHER INFORMATION: Xaa is selected from A and S
<220> FEATURE:
<221> NAME/KEY: MISC_FEATURE
<222> LOCATION: (11)..(11)
<223> OTHER INFORMATION: Xaa is selected from N and E
<220> FEATURE:
<221> NAME/KEY: MISC_FEATURE
<222> LOCATION: (14)..(14)
<223> OTHER INFORMATION: Xaa is selected from A, S, and C
<220> FEATURE:
<221> NAME/KEY: MISC_FEATURE
<222> LOCATION: (20)..(20)
<223> OTHER INFORMATION: Xaa is selected from E, N, and S
<220> FEATURE:
<221> NAME/KEY: MISC_FEATURE
<222> LOCATION: (21)..(21)
<223> OTHER INFORMATION: Xaa is selected from D, E, and S
<220> FEATURE:
<221> NAME/KEY: MISC_FEATURE
<222> LOCATION: (22)..(22)
<223> OTHER INFORMATION: Xaa is selected from A and S

<400> SEQUENCE: 290

Ala Glu Ala Lys Tyr Ala Lys Gln Ser Xaa Xaa Leu Leu Xaa Glu Ala
1               5                   10                  15

Lys Lys Leu Xaa Xaa Xaa Gln Ala Pro
            20                  25

<210> SEQ ID NO 291
<211> LENGTH: 29
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (2)..(2)
<223> OTHER INFORMATION: Xaa is selected from H, Q, S, T, and V
<220> FEATURE:
<221> NAME/KEY: MISC_FEATURE
<222> LOCATION: (3)..(3)
<223> OTHER INFORMATION: Xaa is selected from I, L, M, and V
<220> FEATURE:
<221> NAME/KEY: MISC_FEATURE
<222> LOCATION: (4)..(4)
<223> OTHER INFORMATION: Xaa is selected from A, D, E, H, K, L, N, Q, R,
```

```
            S, T, and Y
<220> FEATURE:
<221> NAME/KEY: MISC_FEATURE
<222> LOCATION: (6)..(6)
<223> OTHER INFORMATION: Xaa is selected from N and W
<220> FEATURE:
<221> NAME/KEY: MISC_FEATURE
<222> LOCATION: (7)..(7)
<223> OTHER INFORMATION: Xaa is selected from A, D, E, H, N, Q, R, S,
      and T
<220> FEATURE:
<221> NAME/KEY: MISC_FEATURE
<222> LOCATION: (11)..(11)
<223> OTHER INFORMATION: Xaa is selected from D and E
<220> FEATURE:
<221> NAME/KEY: MISC_FEATURE
<222> LOCATION: (12)..(12)
<223> OTHER INFORMATION: Xaa is selected from A, E, G, H, K, L, Q, R, S,
      T, and Y
<220> FEATURE:
<221> NAME/KEY: MISC_FEATURE
<222> LOCATION: (17)..(17)
<223> OTHER INFORMATION: Xaa is selected from N and T
<220> FEATURE:
<221> NAME/KEY: MISC_FEATURE
<222> LOCATION: (18)..(18)
<223> OTHER INFORMATION: Xaa is selected from I, L, and V
<220> FEATURE:
<221> NAME/KEY: MISC_FEATURE
<222> LOCATION: (19)..(19)
<223> OTHER INFORMATION: Xaa is selected from A, D, E, H, K, N, Q, R, S,
      and T
<220> FEATURE:
<221> NAME/KEY: MISC_FEATURE
<222> LOCATION: (22)..(22)
<223> OTHER INFORMATION: Xaa is selected from I, L, and V
<220> FEATURE:
<221> NAME/KEY: MISC_FEATURE
<222> LOCATION: (26)..(26)
<223> OTHER INFORMATION: Xaa is selected from A, D, E, G, H, N, S, and T
<220> FEATURE:
<221> NAME/KEY: MISC_FEATURE
<222> LOCATION: (27)..(27)
<223> OTHER INFORMATION: Xaa is selected from K and S
<220> FEATURE:
<221> NAME/KEY: MISC_FEATURE
<222> LOCATION: (29)..(29)
<223> OTHER INFORMATION: Xaa is selected from A, D, E, H, N, Q, S, T,
      and Y

<400> SEQUENCE: 291

Glu Xaa Xaa Xaa Ala Xaa Xaa Glu Ile Asp Xaa Xaa Leu Pro Asn Leu
1               5                   10                  15

Xaa Xaa Xaa Gln Trp Xaa Ala Phe Ile Xaa Xaa Leu Xaa
            20                  25

<210> SEQ ID NO 292
<211> LENGTH: 28
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (2)..(2)
<223> OTHER INFORMATION: Xaa is selected from H, Q, S, T, and V
<220> FEATURE:
<221> NAME/KEY: MISC_FEATURE
<222> LOCATION: (3)..(3)
<223> OTHER INFORMATION: Xaa is selected from I, L, M, and V
<220> FEATURE:
<221> NAME/KEY: MISC_FEATURE
<222> LOCATION: (4)..(4)
<223> OTHER INFORMATION: Xaa is selected from A, D, E, H, K, L, N, Q, R,
      S, T, and Y
<220> FEATURE:
```

<221> NAME/KEY: MISC_FEATURE
<222> LOCATION: (6)..(6)
<223> OTHER INFORMATION: Xaa is selected from N and W
<220> FEATURE:
<221

```
<223> OTHER INFORMATION: Xaa is selected from A, D, E, H, N, Q, R, S,
      and T
<220> FEATURE:
<221> NAME/KEY: MISC_FEATURE
<222> LOCATION: (17)..(17)
<223> OTHER INFORMATION: Xaa is selected from D and E
<220> FEATURE:
<221> NAME/KEY: MISC_FEATURE
<222> LOCATION: (18)..(18)
<223> OTHER INFORMATION: Xaa is selected from A, E, G, H, K, L, Q, R, S,
      T, and Y
<220> FEATURE:
<221> NAME/KEY: MISC_FEATURE
<222> LOCATION: (23)..(23)
<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from I, L, and V
<220> FEATURE:
<221> NAME/KEY: MISC_FEATURE
<222> LOCATION: (25)..(25)
<223> OTHER INFORMATION: Xaa is selected from A, D, E, H, K, N, Q, R, S,
      and T
<220> FEATURE:
<221> NAME/KEY: MISC_FEATURE
<222> LOCATION: (28)..(28)
<223> OTHER INFORMATION: Xaa is selected from I, L, and V
<220> FEATURE:
<221> NAME/KEY: MISC_FEATURE
<222> LOCATION: (32)..(32)
<223> OTHER INFORMATION: Xaa is selected from A, D, E, G, H, N, S, and T
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from A, D, E, H, N, Q, S, T,
      and Y
<220> FEATURE:
<221> NAME/KEY: MISC_FEATURE
<222> LOCATION: (35)..(36)
<223> OTHER INFORMATION: an interconnecting loop selected from DDPS and
      RQPE
<220> FEATURE:
<221> NAME/KEY: MISC_FEATURE
<222> LOCATION: (38)..(38)
<223> OTHER INFORMATION: Xaa is selected from A and S
<220> FEATURE:
<221> NAME/KEY: MISC_FEATURE
<222> LOCATION: (39)..(39)
<223> OTHER INFORMATION: Xaa is selected from N and E
<220> FEATURE:
<221> NAME/KEY: MISC_FEATURE
<222> LOCATION: (42)..(42)
<223> OTHER INFORMATION: Xaa is selected from A, S, and C
<220> FEATURE:
<221> NAME/KEY: MISC_FEATURE
<222> LOCATION: (48)..(48)
<223> OTHER INFORMATION: Xaa is selected from E, N, and S
<220> FEATURE:
<221> NAME/KEY: MISC_FEATURE
<222> LOCATION: (49)..(49)
<223> OTHER INFORMATION: Xaa is selected from D, E, and S
<220> FEATURE:
<221> NAME/KEY: MISC_FEATURE
<222> LOCATION: (50)..(50)
<223> OTHER INFORMATION: Xaa is selected from A and S

<400> SEQUENCE: 293

Ala Glu Ala Lys Tyr Ala Lys Glu Xaa Xaa Xaa Ala Xaa Xaa Glu Ile
1               5                   10                  15

Xaa Xaa Leu Pro Asn Leu Xaa Xaa Xaa Gln Trp Xaa Ala Phe Ile Xaa
            20                  25                  30
```

Xaa Leu Xaa Gln Ser Xaa Xaa Leu Leu Xaa Glu Ala Lys Lys Leu Xaa
            35                  40                  45

Xaa Xaa Gln Ala Pro
    50

<210> SEQ ID NO 294
<211> LENGTH: 53
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (9)..(9)
<223> OTHER INFORMATION: Xaa is selected from H, Q, S, T, and V
<220> FEATURE:
<221> NAME/KEY: MISC_FEATURE
<222> LOCATION: (10)..(10)
<223> OTHER INFORMATION: Xaa is selected from I, L, M, and V
<220> FEATURE:
<221> NAME/KEY: MISC_FEATURE
<222> LOCATION: (11)..(11)
<223> OTHER INFORMATION: Xaa is selected from A, D, E, H, K, L, N, Q, R,
      S, T, and Y
<220> FEATURE:
<221> NAME/KEY: MISC_FEATURE
<222> LOCATION: (13)..(13)
<223> OTHER INFORMATION: Xaa is selected from N and W
<220> FEATURE:
<221> NAME/KEY: MISC_FEATURE
<222> LOCATION: (14)..(14)
<223> OTHER INFORMATION: Xaa is selected from A, D, E, H, N, Q, R, S,
      and T
<220> FEATURE:
<221> NAME/KEY: MISC_FEATURE
<222> LOCATION: (18)..(18)
<223> OTHER INFORMATION: Xaa is selected from A, E, G, H, K, L, Q, R, S,
      T, and Y
<220> FEATURE:
<221> NAME/KEY: MISC_FEATURE
<222> LOCATION: (23)..(23)
<223> OTHER INFORMATION: Xaa is selected from N and T
<220> FEATURE:
<221> NAME/KEY: MISC_FEATURE
<222> LOCATION: (24)..(24)
<223> OTHER INFORMATION: Xaa is selected from I, L, and V
<220> FEATURE:
<221> NAME/KEY: MISC_FEATURE
<222> LOCATION: (25)..(25)
<223> OTHER INFORMATION: Xaa is selected from A, D, E, H, K, N, Q, R, S,
      and T
<220> FEATURE:
<221> NAME/KEY: MISC_FEATURE
<222> LOCATION: (28)..(28)
<223> OTHER INFORMATION: Xaa is selected from I, L, and V
<220> FEATURE:
<221> NAME/KEY: MISC_FEATURE
<222> LOCATION: (32)..(32)
<223> OTHER INFORMATION: Xaa is selected from D, E, G, H, N, S, and T
<220> FEATURE:
<221> NAME/KEY: MISC_FEATURE
<222> LOCATION: (33)..(33)
<223> OTHER INFORMATION: Xaa is selected from K and S
<220> FEATURE:
<221> NAME/KEY: MISC_FEATURE
<222> LOCATION: (35)..(35)
<223> OTHER INFORMATION: Xaa is selected from A, D, E, H, N, Q, S, T,
      and Y
<220> FEATURE:
<221> NAME/KEY: MISC_FEATURE
<222> LOCATION: (35)..(36)
<223> OTHER INFORMATION: an interconnecting loop selected from DDPS and
      RQPE
<220> FEATURE:
<221> NAME/KEY: MISC_FEATURE
<222> LOCATION: (38)..(38)
<223> OTHER INFORMATION: Xaa is selected from A and S
<220> FEATURE:
<221> NAME/KEY: MISC_FEATURE
<222> LOCATION: (39)..(39)
<223> OTHER INFORMATION: Xaa is selected from N and E
<220> FEATURE:
<221> NAME/KEY: MISC_FEATURE
<222> LOCATION: (42)..(42)
<223> OTHER INFORMATION: Xaa is selected from A, S, and C
<220> FEATURE:
<221> NAME/KEY: MISC_FEATURE
<222> LOCATION: (48)..(48)
<223> OTHER INFORMATION: Xaa is selected from E, N, and S
<220> FEATURE:
<221> NAME/KEY: MISC_FEATURE
<222> LOCATION: (49)..(49)
<223> OTHER INFORMATION: Xaa is selected from D, E, and S
<220> FEATURE:
<221> NAME/KEY: MISC_FEATURE
<222> LOCATION: (50)..(50)
<223> OTHER INFORMATION: Xaa is selected from A and S

<400> SEQUENCE: 294

```
Ala Glu Ala Lys Tyr Ala Lys Glu Xaa Xaa Xaa Ala Xaa Xaa Glu Ile
1               5                   10                  15

Asp Xaa Leu Pro Asn Leu Xaa Xaa Xaa Gln Trp Xaa Ala Phe Ile Xaa
            20                  25                  30

Xaa Leu Xaa Gln Ser Xaa Xaa Leu Leu Xaa Glu Ala Lys Lys Leu Xaa
        35                  40                  45

Xaa Xaa Gln Ala Pro
    50
```

<210> SEQ ID NO 295
<211> LENGTH: 5
<212> TYPE: PRT
<213> ORGANISM: Artificial Sequence
<220> FEATURE:
<223> OTHER INFORMATION: linking moiety
<220> FEATURE:
<221> NAME/KEY: MISC_FEATURE
<222> LOCATION: (3)..(3)
<223> OTHER INFORMATION: Xaa is selected from D, E, and A

<400> SEQUENCE: 295

```
Lys Val Xaa Gly Ser
1               5
```

<210> SEQ ID NO 296
<211> LENGTH: 16
<212> TYPE: PRT
<213> ORGANISM: Artificial Sequence
<220> FEATURE:
<223> OTHER INFORMATION: Modified C5 binding motif
<220> FEATURE:
<221> NAME/KEY: MISC_FEATURE
<222> LOCATION: (1)..(1)
<223> OTHER INFORMATION: a C5 binding motif
<220> FEATURE:
<221> NAME/KEY: MISC_FEATURE
<222> LOCATION: (1)..(1)
<223> OTHER INFORMATION: an interconnecting loop selected from DDPS and RQPE
<220> FEATURE:
<221> NAME/KEY: MISC_FEATURE
<222> LOCATION: (3)..(3)
<223> OTHER INFORMATION: Xaa is selected from A and S
<220> FEATURE:
<221> NAME/KEY: MISC_FEATURE
<222> LOCATION: (4)..(4)
<223> OTHER INFORMATION: Xaa is selected from N and E
<220> FEATURE:
<221> NAME/KEY: MISC_FEATURE
<222> LOCATION: (7)..(7)

```
<223> OTHER INFORMATION: Xaa is selected from A, S, and C
<220> FEATURE:
<221> NAME/KEY: MISC_FEATURE
<222> LOCATION: (13)..(13)
<223> OTHER INFORMATION: Xaa is selected from E, N, and S
<220> FEATURE:
<221> NAME/KEY: MISC_FEATURE
<222> LOCATION: (14)..(14)
<223> OTHER INFORMATION: Xaa is selected from D, E, and S
<220> FEATURE:
<221> NAME/KEY: MISC_FEATURE
<222> LOCATION: (15)..(15)
<223> OTHER INFORMATION: Xaa is selected from A and S

<400> SEQUENCE: 296

Gln Ser Xaa Xaa Leu Leu Xaa Glu Ala Lys Lys Leu Xaa Xaa Xaa Gln
1               5                   10                  15

<210> SEQ ID NO 297
<211> LENGTH: 5
<212> TYPE: PRT
<213> ORGANISM: Artificial Sequence
<220> FEATURE:
<223> OTHER INFORMATION: linking moiety

<400> SEQUENCE: 297

Lys Val Glu Gly Ser
1               5

<210> SEQ ID NO 298
<211> LENGTH: 5
<212> TYPE: PRT
<213> ORGANISM: Artificial Sequence
<220> FEATURE:
<223> OTHER INFORMATION: linking moiety

<400> SEQUENCE: 298

Lys Val Ala Gly Ser
1               5

<210> SEQ ID NO 299
<211> LENGTH: 12
<212> TYPE: PRT
<213> ORGANISM: Artificial Sequence
<220> FEATURE:
<223> OTHER INFORMATION: protein Z variant
<220> FEATURE:
<221> NAME/KEY: MISC_FEATURE
<222> LOCATION: (12)..(12)
<223> OTHER INFORMATION: Z variant

<400> SEQUENCE: 299

Met Gly Ser Ser His His His His His His Leu Gln
1               5                   10
```

STABLE POLYPEPTIDES BINDING TO HUMAN COMPLEMENT C5

CROSS-REFERENCE TO RELATED APPLICATIONS

This application is a U.S. National Stage Application of PCT/EP2014/068282 filed Aug. 28, 2014, which claims priority to Swedish Patent Application 1350986-4 filed Aug. 28, 2013, both of which are incorporated by reference in their entireties.

TECHNICAL FIELD

The present invention relates to polypeptides that bind to human complement component 5 (C5) and to the use of such polypeptides in therapy.

BACKGROUND ART

The complement protein C5 is a central component of the complement system; a key part of the innate immune system. The complement system is an intricate immune surveillance system with numerous tasks in tightly controlled, diverse processes. It functions as a first line host defense system against infection by other organisms, and also in discriminating healthy host tissues from cellular debris and apoptotic and necrotic cells. Furthermore, it is involved in clearance of immune complexes, regulation of the adaptive immune response, promotion of tissue regeneration, angiogenesis, mobilization of stem cells and development of the central nervous system (Woodruff et al. Mol Immunol 2011, 48 (14):1631-1642; Ricklin et al. Nat Immunol 2010, 11(9):785-795). Any trigger, for example erroneous or unrestricted activation or insufficient regulation, that disturbs the fine balance of complement activation and regulation may lead to pathologic conditions including self-attack of the host's cells leading to extensive tissue damage.

The complement system consists of about 30 proteins. There are three pathways to initiate complement; the classical pathway that employs C1q to recognize immune complexes on the surface of cells; the lectin pathway that is initiated when mannose-binding lectin (MBL) recognizes certain sugars; and the alternative pathway that is initiated spontaneously by hydrolysis of complement factor 3 (C3), a process suppressed by certain mammalian cell surface molecules not present on invading pathogens. The alternative pathway also acts as an amplification loop for the complement system. All three pathways converge at the level of C3. Cleavage of C3 into C3a and C3b leads to the formation of a convertase that in turn cleaves complement factor 5 (C5) into C5a and C5b. C5a is a very potent attractant of various immune cells while C5b oligomerizes with C6-9 to form a pore known as the membrane attack complex (MAC) or sometimes the terminal complement complex (TCC). Activation of the complement system leads to a number of mechanisms with the purpose of neutralizing the pathogen; formation of MAC on the surface of a cell such as an invading bacteria leads to lysis, deposition of C3 and C4 cleavage products C3b and C4b aids opsonization leading to phagocytosis of the pathogen by macrophages and anaphylatoxins such as C3a and C5a attracts monocytes and neutrophils to the site of activation, up-regulates surface markers leading to increased immunologic susceptibility and to the release of cytokines.

C5 is a 190-kDa glycoprotein comprised of 2 disulfide-linked polypeptide chains, alpha and beta, with a molecular mass of 115 and 75 kDa, respectively (Tack et al. Biochem 1979, 18:1490-1497). Haviland et al. (J Immun 1991, 146: 362-368) constructed the complete cDNA sequence of human complement pro-05, which is predicted to encode a 1,676-amino acid pro-molecule that contains an 18-amino acid leader peptide and a 4-amino acid linker separating the beta and alpha chains (SEQ ID NO: 251). Since C5 is common to all pathways of complement activation, blocking C5 will stop the progression of the cascade regardless of the stimuli and thereby prevent the deleterious properties of terminal complement activation while leaving the immuno-protective and immunoregulatory functions of the proximal complement cascade intact.

The complement system's key role in the defense against pathogens in general makes it an interesting target for pharmaceutical intervention. This is emphasized by the fact that many mutations or impaired regulation of complement is involved in various diseases and conditions. These include increased susceptibility to auto-immune diseases such as systemic lupus erythematosis (SLE) where deposition of immune complexes triggers the classical pathway (Manderson et al. Annu Rev Immunol 2004, 22:431-456). In addition, mutations of the complement proteins C1-C5 often result in SLE or SLE like symptoms. Other autoimmune diseases with a strong involvement of the complement system are rheumatoid arthritis (RA) where immune complexes may activate complement in the RA joint, Sjögren's syndrome, dermatomyositis and other autoantibody driven diseases such as Guillain-Barré syndrome (GBS), Fisher syndrome (Kaida et al. J. Neuroimmun 2010, 223:5-12), different types of vasculitis, systemic sclerosis, anti-glomerular basement membrane (anti-GBM) and anti-phospholipid syndrome (APS) (Chen et al. J Autoimmun 2010, 34:J276-J286). Furthermore, complement inhibition have been proven effective in animal models of such different conditions as periodontitis (Abe et al. J Immunol 2012, 189:5442-5448), wound healing (Cazender et al. Clin Dev Immunol 2012, on-line publication), tumor growth (Markiewski et al. Nat Immunol 2008, 9:1225-1235) and diseases of the eye such as uveitis and age-related macular degeneration (AMD) (Copland et al. Clin Exp Immunol 2009, 159:303-314).

Antibodies targeted to human complement C5 are known from, e.g., WO 95/29697; WO 02/30985; and WO 2004/007553. Eculizumab (SOLIRIS) is a humanized monoclonal antibody directed against protein C5 and prevents cleavage of C5 into C5a and C5b. Eculizumab has been shown to be effective in treating paroxysmal nocturnal hemoglobinuria (PNH), a rare and sometimes life threatening disease of the blood characterized by intravascular hemolytic anemia, thrombophilia and bone marrow failure, and is approved for this indication. Eculizumab was also recently approved by the FDA for treatment of atypical hemolytic syndrome (aHUS), a rare but life threatening disease caused by loss of control of the alternative complement pathway leading to over-activation manifested as thrombotic microangiopathy (TMA) leading to constant risk of damage to vital organs such as kidney, heart and the brain. In aHUS, transplantation of the damaged organ only temporarily helps the patient as the liver continues to produce the mutated form of controlling protein (most often complement factor H or other proteins of the alternative pathway). A related disease with a transient acute pathophysiology is HUS caused by infection of Shiga toxin positive *E. coli* (STEC-HUS) and there are promising clinical data suggesting efficacy also for this condition (Lapeyraque et al, N Engl J Med 2011, 364:2561-2563). Finally, the C5 blocking antibody Eculizumab has proven efficacious in preventing antibody mediated rejection (AMR) in recipients of highly mismatched kidneys (Stegall, M. D. et al. Am J Transplant 2011, 11:2405-2413), and in treating autoimmune neuropathies such as neuromyelitis optica and myasthenia gravis (Pittock et al. Lancet Neurol 2013, 12:554-562; Howard et al. Muscle Nerve 2013, 48:76-84).

Apart from full length antibodies, single-chain variable fragments (scFV), minibodies and aptamers targeting C5 are described in literature. These C5 inhibitors may bind to different sites (epitopes) on the C5 molecule and may have different modes of action. For example, whereas Eculizumab interacts with C5 at some distance of the convertase cleavage site, the minibody MUBODINA interacts with the cleavage site of C5. The C5 inhibitory protein *Ornithodoros moubata* Complement Inhibitor (OmCI, Nunn, M. A. et al. J Immunol 2005, 174:2084-2091) from soft tick *Ornithodoros moubata* has been hypothesized to bind to the distal end of the CUB-05d-MG8 superdomain, which is close to the convertase cleavage site (Fredslund et al. Nat Immunol 2008, 9 (7):753-760). In contrast to the three proteins mentioned above inhibiting cleavage of C5, the monoclonal antibody TNX-558 binds to a C5a epitope present both on intact C5 and released C5a without inhibiting the cleavage of C5. (Fung et al. Clin Exp Immunol 2003, 133 (2):160-169).

C5 binding polypeptides, comprising a C5 binding motif, are disclosed in the International Patent Application No. PCT/SE2013/050139, published as WO 2013/126006. In particular, WO 2013/126006 discloses a C5 binding motif, BM, consisting of the amino acid sequence $$EX_2X_3X_4A\ X_6X_7EID\ X_{11}LPNL\ X_{16}X_{17}X_{18}QW$$
$$X_{21}AFIX_{25}\ X_{26}LX_{28}D, \quad \text{(SEQ ID NO: 288)}$$

wherein, independently of each other,
$X_2$ is selected from H, Q, S, T and V;
$X_3$ is selected from I, L, M and V;
$X_4$ is selected from A, D, E, H, K, L, N, Q, R, S, T and Y;
$X_6$ is selected from N and W;
$X_7$ is selected from A, D, E, H, N, Q, R, S and T;
$X_{11}$ is selected from A, E, G, H, K, L, Q, R, S, T and Y;
$X_{16}$ is selected from N and T;
$X_{17}$ is selected from I, L and V;
$X_{18}$ is selected from A, D, E, H, K, N, Q, R, S and T;
$X_{21}$ is selected from I, L and V;
$X_{25}$ is selected from D, E, G, H, N, S and T;
$X_{26}$ is selected from K and S; and
$X_{28}$ is selected from A, D, E, H, N, Q, S, T and Y.

Examples of specific C5 binding motifs, as previously disclosed in WO 2013/126006, are shown as SEQ ID NO: 1-248 in the present patent application.

It is known from WO 2013/126006 that additional peptides or polypeptides may improve stabilization of C5 binding polypeptides. One example of such a polypeptide is the albumin binding domain (ABD) shown as SEQ ID NO: 250 in the present description. Other examples of suitable albumin binding domains are disclosed in WO 2009/016043 and WO 2012/004384. An ABD-extended polypeptide binds to serum albumin in vivo, and benefits from its longer half-life, which increases the net half-life of the polypeptide itself (see e.g. WO 91/01743).

The continued provision of agents with comparable C5 blocking activity remains a matter of substantial interest within the field. In particular, there is a continued need for molecules that prevent the terminal complement cascade as well as the formation of the pro-inflammatory molecule C5a. Of great interest is also a provision of uses of such molecules in the treatment of disease.

BRIEF DESCRIPTION OF THE DRAWINGS

FIG. 6A shows a gel of HER2 binding polypeptides wherein the lanes show lane 1: Mw, lane 2: (0) Z02891 (SEQ ID NO: 272), lane 3: (2 w) Z02891 (SEQ ID NO: 272), lane 4: Mw, lane 5: (0) Z17341 (SEQ ID NO: 273), lane 6: (2 w) Z17341 (SEQ ID NO: 273), lane 7: (0) Z17342 (SEQ ID NO: 274), lane 8: (2 w) Z17342 (SEQ ID NO: 274). FIG. 6B is a gel of PDGF-Rβ binding polypeptides wherein the lanes show: lane 1: Mw, lane 2: (0) Z15805 (SEQ ID NO: 275), lane 3: (2 w) Z15805 (SEQ ID NO: 275), lane 4: Mw, lane 5: (0) Z17343 (SEQ ID NO: 276), lane 6: (2 w) Z17343 (SEQ ID NO: 276), lane 7: (0) Z17344 (SEQ ID NO: 277), lane 8: (2 w) Z17344 (SEQ ID NO: 277). FIG. 6C shows a gel of FcRn binding polypeptides wherein the lanes show: lane 1: (0) Z10103 (SEQ ID NO: 278), lane 2: (2 w) Z10103 (SEQ ID NO: 278), lane 3: Mw, lane 4: (0) Z17347 (SEQ ID NO: 279), lane 5: (2 w) Z17347 (SEQ ID NO: 279), lane 6: (0) Z17348 (SEQ ID NO: 280), lane 7: (2 w) Z17348 (SEQ ID NO: 280). The diagonal bands seen in FIG. 6C is an artefact resulting from an imprint from a second gel stained in the same container. FIG. 6D is a gel of CAIX binding polypeptides wherein the lanes show lane 1: Mw, lane 2: (0) Z09782 (SEQ ID NO: 281), lane 3: (2 w) Z09782 (SEQ ID NO: 281), lane 4: Mw, lane 5: (0) Z17351 (SEQ ID NO: 282), lane 6: (2 w) Z17351 (SEQ ID NO: 282), lane 7: (0) Z17352 (SEQ ID NO: 283), lane 8: (2 w) Z17352 (SEQ ID NO: 283); lane 9: (0) Z17355 (SEQ ID NO: 284), lane 10: (2 w) Z17355 (SEQ ID NO: 284), lane 11: (0) Z17357 (SEQ ID NO: 285), lane 12: (2 w) Z17357 (SEQ ID NO: 285), lane 13: (0) Z17359 (SEQ ID NO: 286), lane 14: (2 w) Z17359 (SEQ ID NO: 286), lane 15: (0) Z17360 (SEQ ID NO: 287), lane 16: (2 w) Z17360 (SEQ ID NO: 287).

FIG. 7A-M is a table showing the amino acid sequences of:

Figure 1:
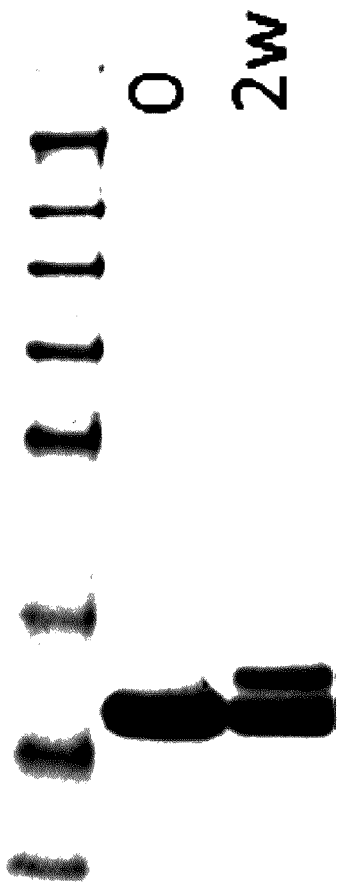
FIG. 1 illustrates an SDS-PAGE gel wherein the bands represent the C5 binding compound PSI0242 (SEQ ID NO: 249) (0) prior to stability test; and (2 w) after 2 weeks stability test.
Figure 2:
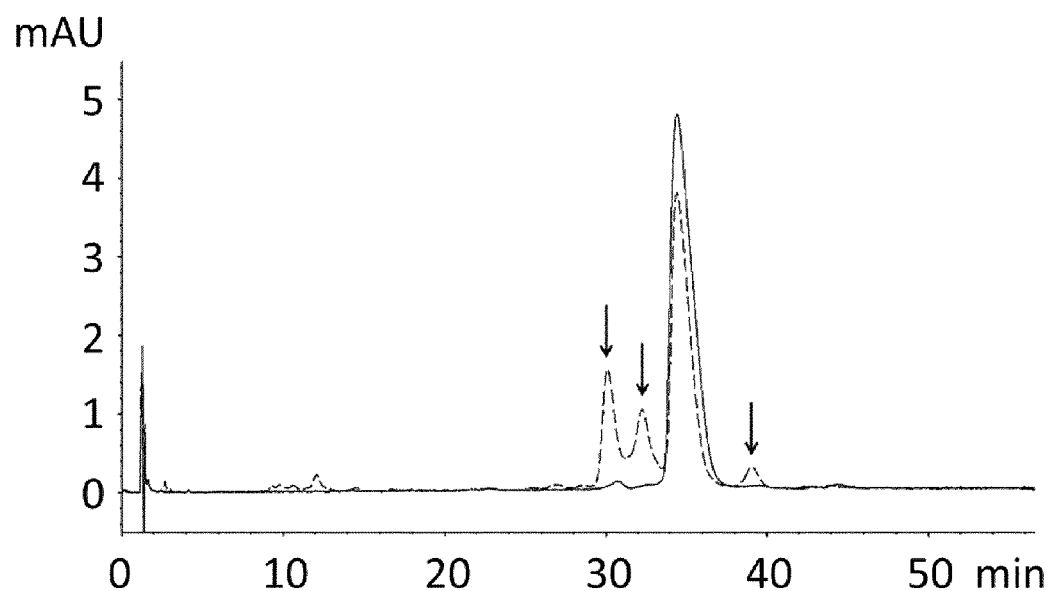
FIG. 2 is a chromatogram from reversed phase HPLC of PSI0242 (SEQ ID NO: 249) prior to stability test (solid line) and after 2 weeks stability test (dotted line).

examples of C5 binding motifs (SEQ ID NO: 1-248);
the C5 binding compound designated PSI0242 (SEQ NO: 249);
an albumin binding domain (SEQ ID NO: 250);
the Swiss-Prot entry P01031 of human C5 (SEQ ID NO:251) wherein the α-chain corresponds to amino acid residues 678-1676 and the β-chain corresponds to amino acid residues 19-673;
examples of modified C5 binding polypeptides (SEQ ID NO: 260, 265-267).
examples of modified C5 binding compounds (SEQ ID NO: 252-259, 261-264, 268-270).
- examples of polypeptide variants with binding affinity for other target molecules (SEQ ID NO: 272, 275, 278, 281)
- examples of stability improved polypeptide variants with binding affinity for other targets with (SEQ ID NO: 273-274, 276-277, 279-280, 282-287).

DISCLOSURE OF THE INVENTION

It has surprisingly been found that C5 binding polypeptides and compounds, wherein the amino acid sequences have been modified in specific positions, have improved stability when compared to previously known C5 binding polypeptides and compounds.

Consequently, this invention provides a polypeptide capable of binding human complement component 5 (C5), said polypeptide being selected from:

(a) a polypeptide comprising the amino acid sequence (SEQ ID NO: 289)
$[BM]-[L2]-QSX_{42}X_{43}LLX_{46}EAKKLX_{52}X_{53}X_{54}Q$ wherein, independently of each other,
[BM] is a C5 binding motif;
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S, provided that $X_{53}$ is not D when $X_{52}$ is N; and
$X_{54}$ is selected from A and S; and (b) a polypeptide which has at least 89% amino acid sequence identity with the polypeptide of (a), provided that $X_{53}$ is not D when $X_{52}$ is N.

The inventors have surprisingly found that modification or substitution of amino acid residue(s) in certain position(s) of the amino acid sequence of the C5 binding polypeptides as described in WO 2013/126006 improves stability of the C5 binding polypeptides while biological activity, such as binding affinity for human complement component 5 (C5) and inhibition of complement pathway function, is essentially retained. Thus, the biological activity of the modified C5 binding polypeptides is comparable to the biological activity of the known C5 binding polypeptides. Stability testing of the C5 binding polypeptides of the present invention demonstrates that substitution in either $X_{52}$, from N to E or S, or $X_{53}$, from D to E or S, improves stability. It has moreover been found that specific amino acid substitution in [L2] independently may promote stability.

The terms "C5 binding" and "binding affinity for C5" as used in this specification refers to a property of a polypeptide which may be tested for example by the use of surface plasmon resonance technology, such as in a Biacore instrument (GE Healthcare). C5 binding affinity may e.g. be tested in an experiment in which C5 is immobilized on a sensor chip of a Biacore instrument, and the sample containing the polypeptide to be tested is passed over the chip. Alternatively, the polypeptide to be tested is immobilized on a sensor chip of the instrument, and a sample containing C5, or fragment thereof, is passed over the chip. The skilled person may then interpret the results obtained by such experiments to establish at least a qualitative measure of the binding of the polypeptide to C5. If a quantitative measure is desired, for example to determine the apparent equilibrium dissociation constant $K_D$ for the interaction, surface plasmon resonance methods may also be used. Binding values may for example be defined in a Biacore 2000 instrument (GE Healthcare). C5 is immobilized on a sensor chip of the measurement, and samples of the polypeptide whose affinity is to be determined are prepared by serial dilution and injected over the chip. $K_D$ values may then be calculated from the results using for example the 1:1 Langmuir binding model of the BIAevaluation software provided by the instrument manufacturer. The C5 or fragment thereof used in the $K_D$ determination may for example comprise the amino acid sequence represented by SEQ ID NO: 251. Examples of how C5 binding affinity may be tested are given herein, see Example 3 and 5.

In a preferred form of the invention, said polypeptide is selected from:

(a) a polypeptide comprising the amino acid sequence (SEQ ID NO: 290)
$AEAKYAK-[BM]-[L2]-QSX_{42}X_{43}LLX_{46}EAKKLX_{52}X_{53}X_{54}QAP$ wherein, independently of each other,
[BM], [L2], $X_{42}$, $X_{43}$, $X_{46}$, $X_{52}$, $X_{53}$ and $X_{54}$ are as defined above; and (b) a polypeptide which has at least 90% amino acid sequence identity with the polypeptide of (a), provided that $X_{53}$ is not D when $X_{52}$ is N.

As previously disclosed in WO 2013/126006, the C5 binding polypeptide according to the invention may form part of a three-helix bundle protein domain. Said C5 binding motif [BM] essentially may form part of two alpha helices, with an interconnecting loop, within said three-helix bundle. A second interconnecting loop, referred to herein as [L2], connects the C5 binding motif to the third alpha helix, referred to as the "Backbone".

In one embodiment, the C5 binding motif [BM] is essentially as disclosed in WO 2013/126006. However, according to the present invention the C5 binding motif preferably consists of 28, rather than 29, amino acids, and may in addition carry further amino acid substitutions.

Thus in one embodiment, said [BM] carries at least one further amino acid substitution, e.g. in position 17, when compared to the [BM] as disclosed in WO 2013/126006. Thus, said [BM] is a polypeptide selected from:

(a) a polypeptide comprising the amino acid sequence (SEQ ID NO: 291)
$EX_9X_{10}X_{11}A\ X_{13}X_{14}EIDX_{17}X_{18}LPNLX_{23}X_{24}X_{25}$ $QWX_{28}AFIX_{32}X_{33}LX_{35};$ wherein, independently of each other,
$X_9$ is selected from H, Q, S, T and V;
$X_{10}$ is selected from I, L, M and V;
$X_{11}$ is selected from A, D, E, H, K, L, N, Q, R, S, T and Y;

$X_{13}$ is selected from N and W;
$X_{14}$ is selected from A, D, E, H, N, Q, R, S and T;
$X_{17}$ is selected from D and E;
$X_{18}$ is selected from A, E, G, H, K, L, Q, R, S, T and Y;
$X_{23}$ is selected from N and T;
$X_{24}$ is selected from I, L and V;
$X_{25}$ is selected from A, D, E, H, K, N, Q, R, S and T;
$X_{28}$ is selected from I, L and V;
$X_{32}$ is selected from A, D, E, G, H, N, S and T;
$X_{33}$ is selected from K and S;
$X_{35}$ is selected from A, D, E, H, N, Q, S, T and Y; and (b) a polypeptide which has at least 85% amino acid sequence identity with the polypeptide of (a).

In a preferred embodiment, the C5 binding motif [BM] is essentially as disclosed in WO 2013/126006. Said [BM] is accordingly a polypeptide selected from:

(a) a polypeptide comprising the amino acid sequence (SEQ ID NO: 292)
EX$_9$X$_{10}$X$_{11}$A X$_{13}$X$_{14}$EIDX$_{18}$LPNLX$_{23}$X$_{24}$X$_{25}$

QWX$_{28}$AFIX$_{32}$X$_{33}$LX$_{35}$;

wherein, independently of each other,
$X_9$ is selected from H, Q, S, T and V;
$X_{10}$ is selected from I, L, M and V;
$X_{11}$ is selected from A, D, E, H, K, L, N, Q, R, S, T and Y;
$X_{13}$ is selected from N and W;
$X_{14}$ is selected from A, D, E, H, N, Q, R, S and T;
$X_{18}$ is selected from A, E, G, H, K, L, Q, R, S, T and Y;
$X_{23}$ is selected from N and T;
$X_{24}$ is selected from I, L and V;
$X_{25}$ is selected from A, D, E, H, K, N, Q, R, S and T;
$X_{28}$ is selected from I, L and V;
$X_{32}$ is selected from D, E, G, H, N, S and T;
$X_{33}$ is selected from K and S;
$X_{35}$ is selected from A, D, E, H, N, Q, S, T and Y; and (b) a polypeptide which has at least 85% amino acid sequence identity with the polypeptide of (a).

In a further preferred aspect, [BM] comprises or consists of an amino acid sequence selected from the group consisting of positions 1-28 in SEQ ID NOS: 1-248. More preferably, [BM] comprises or consists of the amino acid sequence shown as positions 1-28 in SEQ ID NO: 1.

In a further aspect, the C5 binding polypeptide according to the invention is selected from:

(a) a polypeptide comprising the amino acid sequence (SEQ ID NO: 293)
AEAKYAKEX$_9$X$_{10}$X$_{11}$AX$_{13}$X$_{14}$EIX$_{17}$X$_{18}$LPNLX$_{23}$

X$_{24}$X$_{25}$QWX$_{28}$AFIX$_{32}$X$_{33}$LX$_{35}$-[L2]-

QSX$_{42}$X$_{43}$LLX$_{46}$EAKKLX$_{52}$X$_{53}$X$_{54}$QAP;

wherein, independently of each other,
$X_9$ is selected from H, Q, S, T and V;
$X_{10}$ is selected from I, L, M and V;
$X_{11}$ is selected from A, D, E, H, K, L, N, Q, R, S, T and Y;
$X_{13}$ is selected from N and W;
$X_{14}$ is selected from A, D, E, H, N, Q, R, S and T;
$X_{17}$ is selected from D and E;
$X_{18}$ is selected from A, E, G, H, K, L, Q, R, S, T and Y;
$X_{23}$ is selected from N and T;
$X_{24}$ is selected from I, L and V;
$X_{25}$ is selected from A, D, E, H, K, N, Q, R, S and T;
$X_{28}$ is selected from I, L and V;
$X_{32}$ is selected from A, D, E, G, H, N, S and T;
$X_{33}$ is selected from K and S;
$X_{35}$ is selected from A, D, E, H, N, Q, S, T and Y;
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S, provided that $X_{53}$ is not D when $X_{52}$ is N; and
$X_{54}$ is selected from A and S; and (b) a polypeptide which has at least 90% amino acid sequence identity with the polypeptide of (a), provided that $X_{53}$ is not D when $X_{52}$ is N.

In a preferred embodiment, the C5 binding polypeptide according to the invention is selected from:

(a) a polypeptide comprising the amino acid sequence (SEQ ID NO: 294)
AEAKYAKEX$_9$X$_{10}$X$_{11}$AX$_{13}$X$_{14}$EIDX$_{18}$LPNLX$_{23}$X$_{24}$X$_{25}$

QWX$_{28}$AFIX$_{32}$X$_{33}$LX$_{35}$-[L2]-QSX$_{42}$X$_{43}$LLX$_{46}$

EAKKLX$_{52}$X$_{53}$X$_{54}$QAP;

wherein, independently of each other,
$X_9$ is selected from H, Q, S, T and V;
$X_{10}$ is selected from I, L, M and V;
$X_{11}$ is selected from A, D, E, H, K, L, N, Q, R, S, T and Y;
$X_{13}$ is selected from N and W;
$X_{14}$ is selected from A, D, E, H, N, Q, R, S and T;
$X_{18}$ is selected from A, E, G, H, K, L, Q, R, S, T and Y;
$X_{23}$ is selected from N and T;
$X_{24}$ is selected from I, L and V;
$X_{25}$ is selected from A, D, E, H, K, N, Q, R, S and T;
$X_{28}$ is selected from I, L and V;
$X_{32}$ is selected from D, E, G, H, N, S and T;
$X_{33}$ is selected from K and S;
$X_{35}$ is selected from A, D, E, H, N, Q, S, T and Y;
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S, provided that $X_{53}$ is not D when $X_{52}$ is N; and
$X_{54}$ is selected from A and S; and (b) a polypeptide which has at least 90% amino acid sequence identity with the polypeptide of (a), provided that $X_{53}$ is not D when $X_{52}$ is N.

In preferred forms of the invention, at least one of the following eighteen, optionally nineteen, conditions is fulfilled:
$X_9$ is V,
$X_{10}$ is L,
$X_{11}$ is E,
$X_{13}$ is W,
$X_{14}$ is D,
optionally $X_{17}$ is D, $X_{18}$ is R,
$X_{23}$ is T,
$X_{24}$ is I,
$X_{25}$ is E,
$X_{28}$ is L,
$X_{32}$ is N,
$X_{33}$ is K,
$X_{35}$ is D,
[L2] is DDPS,
$X_{42}$ is S,
$X_{43}$ is E,
$X_{46}$ is S,
$X_{54}$ is S.

More preferably, at least two, three, four, five, six, seven, eight, nine, ten, eleven, twelve, thirteen, fourteen, fifteen, sixteen, seventeen, eighteen or nineteen of the above conditions are fulfilled.

In an embodiment, $X_{52}$ and $X_{53}$ are independently selected from E and S. Preferably, (a) $X_{52}$ is S and $X_{53}$ is E, or (b) $X_{52}$ is E and $X_{53}$ is S.

In an embodiment, $X_{52}$ is S and $X_{53}$ is D.

In another embodiment, $X_{52}$ is N and $X_{53}$ is E.

In a further aspect, the polypeptide according to the invention comprises the amino sequence shown as SEQ ID NO: 260, SEQ ID NO: 265, SEQ ID NO: 266, or SEQ ID NO: 267.

In a further aspect, there is provided a compound capable of binding C5, said compound comprising:
a. at least one C5 binding polypeptide as defined above;
b. at least one albumin binding domain of streptococcal protein G, or a derivative thereof; and
c. optionally, at least one linking moiety for linking said at least one albumin binding domain or derivative thereof to the C or N terminal of said at least one C5 binding polypeptide.

Preferably, said albumin binding domain comprises the amino acid sequence shown as SEQ ID NO: 250.

Preferably, said linking moiety is a peptide comprising the amino acid sequence KVX$_{60}$GS (SEQ ID NO: 295), wherein $X_{60}$ is selected from D, E and A. When $X_{60}$ is D, a preferred compound comprises or consists of the amino sequence shown as SEQ ID NO: 253. When $X_{60}$ is E, preferred compounds comprise or consist of the amino sequence shown as SEQ ID NO: 261, SEQ ID NO: 263, SEQ ID NO: 264, SEQ ID NO: 269 or SEQ ID NO: 270. When $X_{60}$ is A, a preferred compound comprises or consists of the amino acid sequence shown as SEQ ID NO: 262. In the above listed amino acid sequences of the C5 binding compounds, amino acid residues 1-57 represent the amino acid sequence of a C5 binding polypeptide, residues 58-62 represent the amino acid sequence of a linker, and residues 63-108 represent the amino acid sequence of an albumin binding domain.

In an embodiment, the linking moiety is absent.

As discussed above, preferred C5 binding polypeptides according to the invention include those wherein $X_{52}$ and $X_{53}$ are independently selected from E and S.

Specifically, compounds according to the invention can be derived from PSI0242 (SEQ ID NO: 249) but have modifications in at least one of positions 52, 53 and 60. For instance, as shown in FIGS. 7A-M and the sequence listing, the preferred compound designated PSI0378 (SEQ ID NO: 261) carries the amino acid substitutions N52S, D53E and D60E; the preferred compound designated PSI0379 (SEQ ID NO: 262) carries the amino acid substitutions N52S, D53E and D60A; the preferred compound designated PSI0381 (SEQ ID NO: 263) carries the amino acid substitutions N52E, D53S and D60E; and the preferred compound designated PSI0383 (SEQ ID NO: 264) carries the amino acid substitutions N52S, D53E and D60E. Further, SEQ ID NO: 264 also carries substitutions in the loop [L2], namely D36R, D37Q and S39E. Moreover, the preferred compound designated PSI0403 (SEQ ID NO: 269) carries the amino acid substitutions D53E and D60E, and the preferred compound designated PSI0404 (SEQ ID NO: 270) carries the amino acid substitutions N52S and D60E.

As accounted for above, the inventors have surprisingly found that amino acid substitutions in certain positions of the amino acid sequence of the C5 binding polypeptides as described in WO 2013/126006 may improve stability. Such substitutions improve stability of the C5 binding compounds while biological activity, such as C5 binding capability and inhibition of hemolysis in vitro, is retained. Stability testing of the C5 binding compounds of the present invention demonstrate that for instance each of N52S ($X_{52}$) and D53E ($X_{53}$) (SEQ ID NO: 253) individually, as well as removal of D60 ($X_{60}$) (SEQ ID NO: 259 lacking linking moiety) improves stability. The combination of the substitutions N52S, D53E and D60E or D60A further improves the stability (SEQ ID NO: 261 and SEQ ID NO: 262). Each of the combined substitutions of N52S and D60E (SEQ ID NO: 270) and D53E and D60E (SEQ ID NO: 269) has similarly been found to improve stability. This indicates that each of the listed amino acid substitutions is involved in improving the stability of the polypeptide, and thus that each of these substitutions will provide further stabilized C5 binding polypeptides and compounds compared to previously known C5 binding polypeptides and compounds.

However, the skilled person will be able to identify polypeptides and/or compounds which have modifications in at least one of positions 52, 53 and 60, and/or in the loop [L2], but which also carry additional modifications like substitutions, small deletions, insertions or inversions, and nevertheless have substantially the disclosed biological activities and improved stability. Further, a C5 binding polypeptide and/or compound according to the invention could comprise further C terminal and/or N terminal amino acids that improve production, purification, stabilization in vivo or in vitro, coupling, or detection of the polypeptide.

In a further aspect of the invention, there is provided a compound capable of binding C5, said compound comprising:
a. at least one C5 binding polypeptide, said polypeptide being selected from:
  a-1. a polypeptide comprising the amino acid sequence (SEQ ID NO: 296)
[BM]-[L2]-QSX$_{42}$X$_{43}$LLX$_{46}$EAKKLX$_{52}$X$_{53}$X$_{54}$Q wherein, independently of each other,
[BM] is a C5 binding motif;
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S;
$X_{54}$ is selected from A and S; and
  a-2. a polypeptide which has at least 89% amino acid sequence identity with the polypeptide of a-1;
b. at least one albumin binding domain of streptococcal protein G, or a derivative thereof; and
c. at least one linking moiety for linking said at least one albumin binding domain or derivative thereof to the C or N terminal of said at least one C5 binding polypeptide; wherein the linking moiety comprises or consists of KVEGS (SEQ ID NO: 297) or KVAGS (SEQ ID NO: 298); or wherein said linking moiety is absent.

It has been found that removal of D60 or an amino acid substitution in position 60 of SEQ ID NO: 249 alone improves stability of the C5 binding compounds of the invention compared to previously known C5 binding compounds. Preferably, the linking moiety is KVEGS (SEQ ID NO: 297) ($X_{60}$=E) while $X_{52}X_{53}$ may be ND, and an example of a preferred compound carrying such a linking moiety is PSI0410 (SEQ ID NO: 268). In another preferred embodiment, D60 and the entire linking moiety is absent and an example of such a compound is the preferred compound designated PSI0369 (SEQ ID NO: 259).

In embodiments of the above aspect, [BM] and the albumin binding domain are as defined above in related aspects. Preferably, [L2] is DDPS.

In a further aspect, there is provided a compound capable of binding C5, said compound comprising:
a. at least one C5 binding polypeptide, said polypeptide being selected from:
  a-1. a polypeptide comprising the amino acid sequence $$[BM]-[L2]-QSX_{42}X_{43}LLX_{46}EAKKLX_{52}X_{53}X_{54}Q$$
(SEQ ID NO: 296)

wherein, independently of each other,
  [BM] is a C5 binding motif;
  [L2] is RQPE;
  $X_{42}$ is selected from A and S;
  $X_{43}$ is selected from N and E;
  $X_{46}$ is selected from A, S and C;
  $X_{52}$ is selected from E, N and S;
  $X_{53}$ is selected from D, E and S;
  $X_{54}$ is selected from A and S; and
  a-2. a polypeptide which has at least 89% amino acid sequence identity with the polypeptide of a-1;
b. at least one albumin binding domain of streptococcal protein G, or a derivative thereof; and
c. optionally, at least one linking moiety for linking said at least one albumin binding domain or derivative thereof to the C or N terminal of said at least one C5 binding polypeptide.

Figure 3:
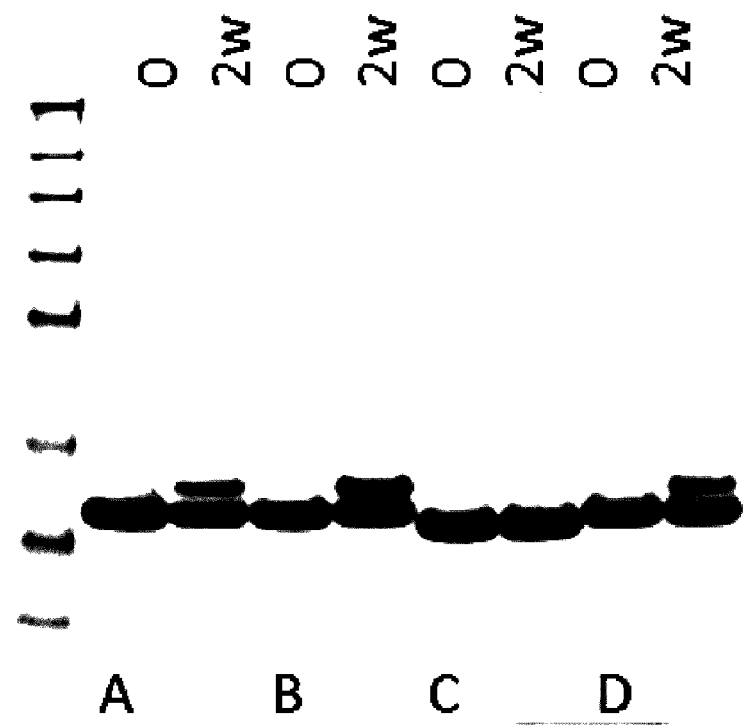
FIG. 3 illustrates an SDS-PAGE gel wherein the first lane contains SeeBlue 2P size marker and the bands represent (0) the initial samples; and (2 w) the samples after 2 weeks stability test. Lane A: SEQ ID NO: 249; Lane B: SEQ ID NO: 261; Lane C: SEQ ID NO: 262; Lane D: SEQ ID NO: 264.

Specific amino acid substitutions in the loop [L2] have been found to improve stability of the C5 binding compounds (e.g. SEQ ID NO: 252) of the invention compared to previously known C5 binding compounds. In embodiments of the above aspect, said [BM] and albumin binding domain are individually as defined above in related aspects. Preferably, said linking moiety is a peptide comprising the amino acid sequence KV$X_{60}$GS (SEQ ID NO: 295), wherein $X_{60}$ is selected from D, E and A.

The invention includes polynucleotides which encode polypeptides according to the invention. Further included in the invention are vectors, such as expression vectors, comprising polynucleotides which encode polypeptides according to the invention. Included are also host cells which comprise such vectors.

Included in the invention are C5 binding polypeptides and compounds as described above, for use in therapy. In particular, the C5 binding polypeptides and compounds according to the invention are useful in methods for the treatment and/or prophylaxis of C5-related conditions, such as inflammatory diseases; autoimmune diseases; infectious diseases; cardiovascular diseases; neurodegenerative disorders; graft injury; eye diseases; kidney diseases; pulmonary diseases; haematological diseases such as paroxysmal nocturnal hemoglobinuria (PNH); allergic diseases and dermatological diseases.

In methods for treatment and/or prophylaxis, the said C5 binding polypeptide or compound can preferably be administered intravenously, subcutaneously, by inhalation, nasally, orally, intravitreally, or topically.

EXAMPLES

Example 1

Stability Test of Known C5 Inhibitor

The C5 binding compound designated PSI0242 (SEQ ID NO: 249) was formulated in 25 mM NaP/125 mM NaCl pH 7.0 and subjected to an accelerated stability study for 2 weeks at 37° C. The stability was measured by the appearance of new variants after the stability testing by SDS-PAGE and Reversed Phase HPLC (RPC). In both analyses the initial sample and the one subjected to the stability study were run in parallel. For the SDS-PAGE, 7.5 μg protein was loaded into each well. The RPC was run on an Agilent 1100 HPLC using a Mobile Phase A consisting of 0.1% trifluoroacetic acid (TFA) in water, and using a Mobile Phase B consisting of 0.1% TFA/45% MeOH/45% isopropylamine (IPA)/10% water.

The results show that new forms of the protein are formed during incubation, these new forms visualized as bands in SDS-PAGE (FIG. 1) and as new peaks in Reversed Phase HPLC (RPC) chromatograms (FIG. 2). In FIG. 2, the main peak after 2 weeks incubation corresponds to 57% of the original protein sample.

Positions 1-60 in SEQ ID NO: 249 correspond to the polypeptide Z06175a, previously disclosed in WO 2013/126006 as SEQ ID NO: 753. PSI0242 (SEQ ID NO: 249) was produced essentially as disclosed in WO 2013/126006.

Example 2

Stability of Modified C5 Binding Polypeptides and Compounds

Modified C5 binding polypeptides and compounds were synthesized and purified essentially as described in WO 2013/126006.

Briefly, DNA encoding C5 binding Z variants was *E. coli* codon optimized and synthesized by GeneArt, GmbH. The synthetic genes representing the C5 binding Z variants were subcloned and expressed in *E. coli*.

Intracellularly expressed Z variants were purified using conventional chromatography methods. Homogenization and clarification was performed by sonication followed by centrifugation and filtration. Anion exchange chromatography was used as capture step. Further purification was obtained by hydrophobic interaction chromatography. The purifications were executed at acidic conditions (pH 5.5). Polishing and buffer exchange was performed by size exclusion chromatography.

The purified proteins were formulated in 25 mM NaP/125 mM NaCl pH 7.0 and subjected to an accelerated stability study for 2 weeks at 37° C. The stability was measured by the appearance of new variants after the stability testing by SDS-PAGE and Reversed Phase HPLC (RPC). In both analyses the initial sample and the one subjected to the stability study were run in parallel. For the SDS-PAGE, 7.5

μg protein was loaded into each well. An example of a resulting gel is shown in FIG. 3.

Figure 4:
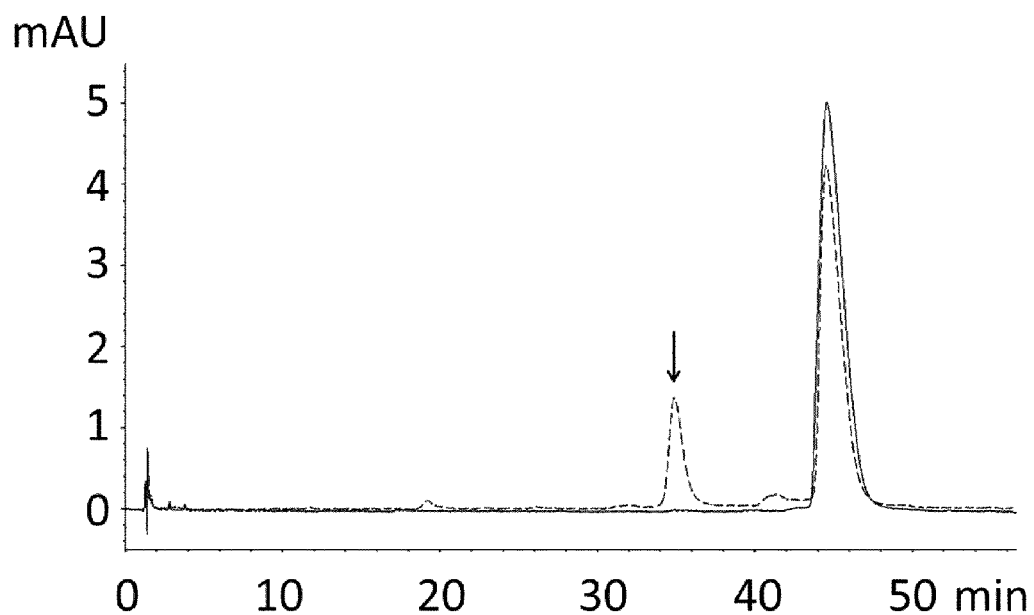
FIG. 4 is a chromatogram from reversed phase HPLC of a C5 binding compound (SEQ ID NO: 253) prior to stability test (solid line) and after 2 weeks stability test (dotted line).

The RPC was run on an Agilent 1100 HPLC using a Mobile Phase A consisting of 0.1% trifluoroacetic acid (TFA) in water, and a Mobile Phase B consisting of 0.1% TFA/45% MeOH/45% isopropylamine (IPA)/10% water. An example of a resulting chromatogram is shown in FIG. 4 for SEQ ID NO: 253.

The results of the stability testing are summarized in Table I, below.

TABLE I

| SEQ ID NO: | Name | SDS-PAGE bands | RPC prepeaks | Main peak (% of total protein) | RPC post peaks |
|---|---|---|---|---|---|
| 249 | PSI0242 | 2 | 2 | 57 | 1 |
| 252 | PSI0332 | 2 | 1 | 57 | 1 |
| 253 | PSI0334 | 1 | 1 | 73 | 0 |
| 254 | PSI0335 | 2 | 2 | 57 | 1 |
| 255 | PSI0336 | 2 | 2 | 57 | 1 |
| 256 | PSI0337 | 2 | 2 | 57 | 1 |
| 257 | PSI0339 | 2 | 2 | 57 | 1 |
| 258 | PSI0340 | 2 | 2 | 67 | 1 |
| 259 | PSI0369 | 2 | 1 | 90 | 1 |
| 260 | PSI0377 | 1 | 0 | 77 | 0 |
| 261 | PSI0378 | 1 | 0 | 89 | 0 |
| 262 | PSI0379 | 1 | 0 | 88 | 0 |
| 263 | PSI0381 | 1 | 0 | 87 | 0 |
| 264 | PSI0383 | 1 | 0 | 91 | 0 |
| 267 | PSI0400 | 1 | 0 | 91 | 0 |
| 268 | PSI0410 | 1 | 1 | 72 | 1 |
| 269 | PSI0403 | 1 | 1 | 77 | 1 |
| 270 | PSI0404 | 1 | 1 | 88 | 0 |

It can be concluded from Table I that certain modified C5 binding polypeptides or compounds have improved properties, such as increased stability, when compared with PSI0242. Such improved C5 binding polypeptides or compounds include PSI0334 (SEQ ID NO: 253), PSI0340 (SEQ ID NO: 258), PSI0369 (SEQ ID NO: 259), PSI0377 (SEQ ID NO: 260), PSI0378 (SEQ ID NO: 261), PSI0379 (SEQ ID NO: 262), PSI0381 (SEQ ID NO: 263), PSI0383 (SEQ ID NO: 264), PSI0400 (SEQ ID NO: 267), PSI0410 (SEQ ID NO: 268), PSI0403 (SEQ ID NO: 269) and PSI0404 (SEQ ID NO: 270). In six of the mentioned variants (SEQ ID NO: 253, 260, 261, 262, 264 and 267), the amino acid residues in positions 52-53 have been substituted from ND (cf PSI0242) to SE. In SEQ ID NO: 263, the corresponding substitution is from ND to ES. In SEQ ID NO: 269 only the amino acid residue in position 53 has been substituted from D to E, while in SEQ ID NO: 270 the amino acid residue in position 52 has been substituted from N to S.

Further, PSI0378 (SEQ ID NO: 261), PSI0381 (SEQ ID NO: 263), PSI0383 (SEQ ID NO: 264), PSI0410 (SEQ ID NO: 268), PSI0403 (SEQ ID NO: 269) and PSI0404 (SEQ ID NO: 270) have in common an amino acid residue substitution from D to E in position 60.

Figure 5:
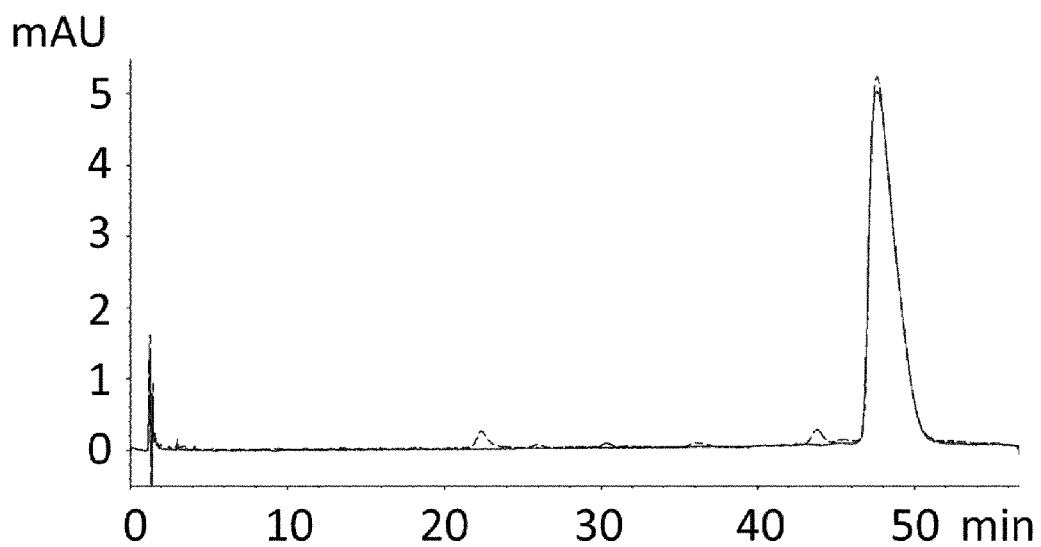
FIG. 5 is a chromatogram from reversed phase HPLC of a C5 binding compound (SEQ ID NO: 264) prior to stability test (solid line) and after 2 weeks stability test (dotted line).
Figure 6B:
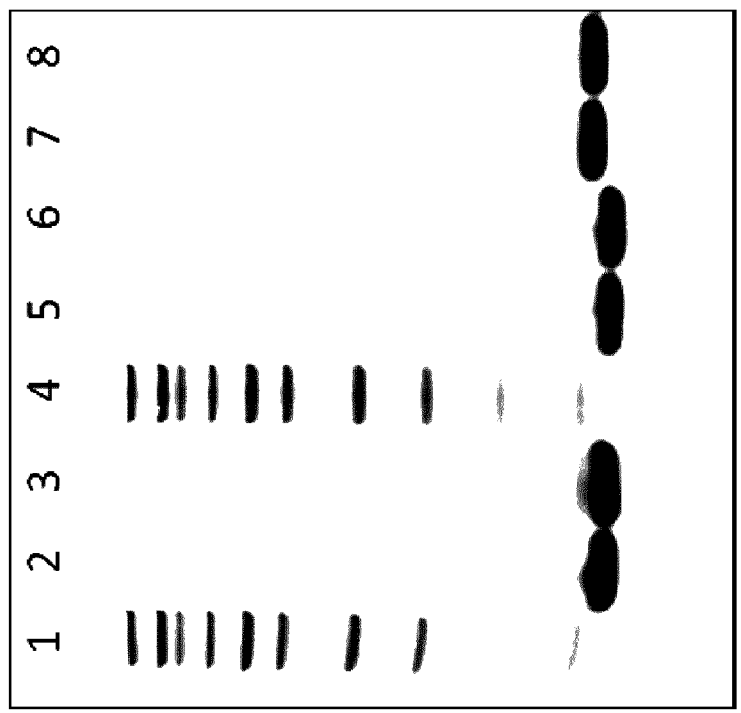
FIG. 6A-D show images of SDS-PAGE gels comparing original and modified polypeptide variants (0) before and (2 w) after 2 weeks stability test. The molecular size marker (Mw) was NOVEX Sharp Pre-stained Protein Standard (216, 160, 110, 80, 60, 50, 40, 30, 20, 15, 10, 3.5 kDa).
Figure 6A:
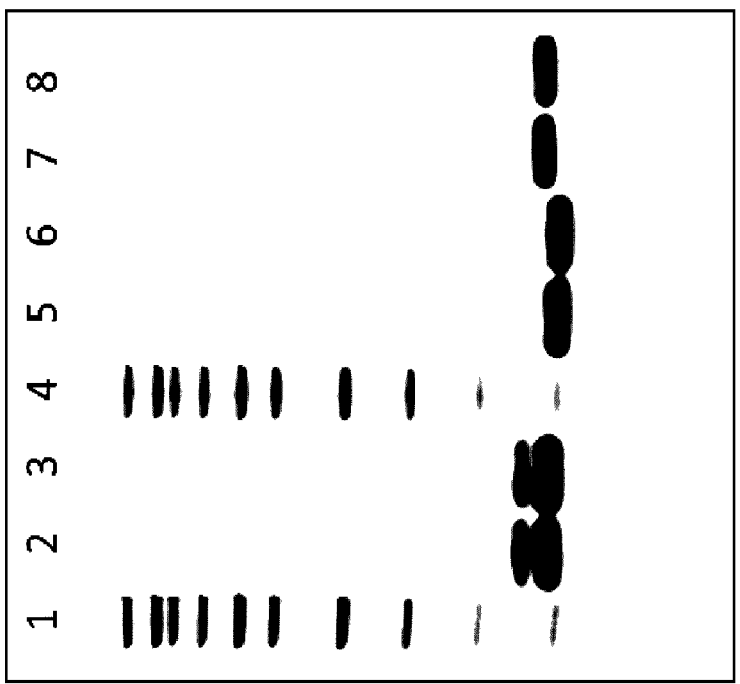
Figure 6C:
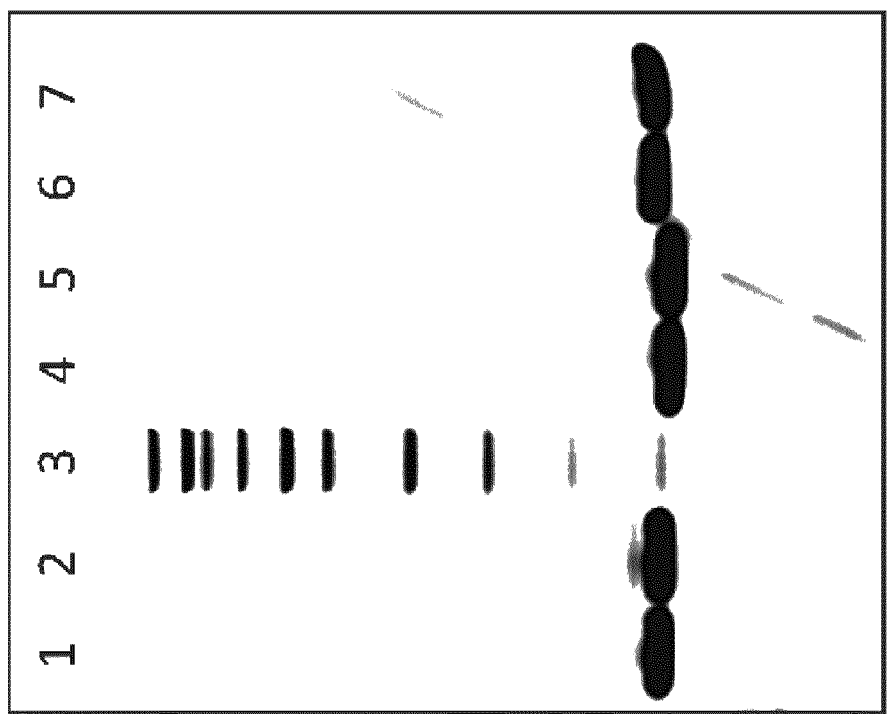
Figure 6D:
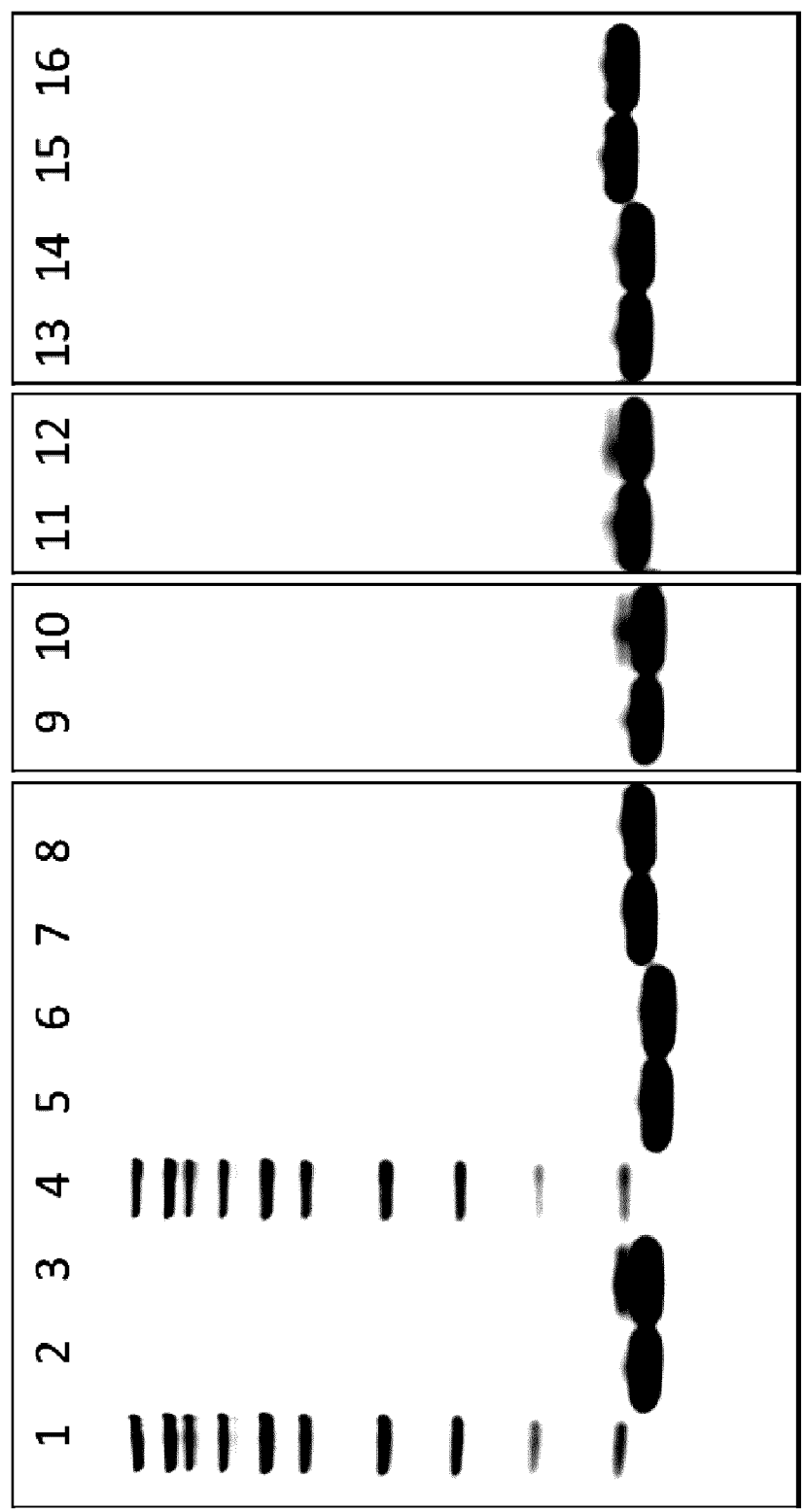

The combined benefit of stability enhancing substitutions in position 52 or 53 and position 60 can be seen in FIG. 5, showing the chromatogram of PSI0383 (SEQ ID NO: 264). In PSI0379 (SEQ ID NO: 262) the substitution in position 60 is from D to A.

In PSI0369 (SEQ ID NO: 259) the linker moeity (including D60) is altogether removed, yielding a more stable C5 binding compound and indicating the influence of position 60 upon stability of the C5 binding compounds.

Example 3

Binding of Modified Compounds to Human C5

Human serum albumin was immobilized to Amine Reactive $2^{nd}$ generation (AR2G) Dip and Read Biosensors (Pall Life sciences (ForteBio) Cat #18-5092) by amine coupling. PSI0242 (SEQ ID NO: 249; 1 μM) and C5 binding compounds (1 μM) in read buffer (HBS-EP Buffer ready-to-use 200 ml, GE Healthcare #BR100188) were loaded, each onto a separate sensor with HSA, for 120 seconds followed by a base line recording for 60 seconds in read buffer before being subjected to human C5 (Quidel Cat #403) in concentrations ranging from 0.79 nM to 25 nM in read buffer with a regeneration cycle and a base line recording between each concentration. Regeneration conditions for the sensors were 10 mM Glycine, pH 2 (three pulses with 30 seconds and running buffer for 60 seconds). Each spectrogram was reference subtracted against an analogous construct containing an albumin binding domain (SEQ ID NO: 250) but without the C5 binding capacity. The data were analyzed according to Langmuir 1:1 model using ForteBio Analysis 7.1 (Pall Life sciences (ForteBio) kinetics software).

The $K_D$ of the interaction with C5 relative to PSI0242 (SEQ ID NO: 249) is shown in Table II. The $K_D$ of PSI0242 varied from 1-3 nM in different runs.

The results in Table II indicate that C5 binding compounds according to the invention have a binding capacity to human C5 which is similar to that of the polypeptide PSI0242 (SEQ ID NO: 249) disclosed in WO 2013/126006.

TABLE III

| SEQ ID NO: | Name | Rel. $K_D$ |
|---|---|---|
| 249 | PSI0242 | 1.0 |
| 253 | PSI0334 | 1.1 |
| 261 | PSI0378 | 1.3 |
| 263 | PSI0381 | 23 |
| 264 | PSI0383 | 2.1 |

Example 4

Stability of Chemically Synthesized C5 Binding Polypeptide

A chemically synthesized PSI0400 (SEQ ID NO: 267) was ordered from BACHEM AG. The stability of the polypeptide was tested according to the same methodology as in Example 2. The results of the stability testing are shown in Table III.

TABLE III

| SEQ ID NO: | Name | SDS-PAGE bands | RPC prepeaks | Main peak (% of total protein) | RPC post peaks |
|---|---|---|---|---|---|
| 267 | PSI0400 | 1 | 0 | 91 | 0 |

The stability of the PSI0400 was comparable to the polypeptides that were produced in *E. coli* in Example 2.

The integrity of the fold of PSI0400 (SEQ ID NO: 267) was compared to a recombinant C5 binding polypeptide (PSI0257, SEQ ID NO: 271), produced in accordance with the methods of Example 2, using far UV circular dichroism (CD) spectra.

The CD spectra were recorded by a J-720 CD spectropolarimeter (Jasco, Japan). The samples were diluted to 0.17 mg/ml protein concentration using Pi buffer (5 mM Na—K—PO$_4$, pH 7.0). A CD spectrum of Pi buffer was firstly recorded, then spectra were recorded for each of the samples and lastly for the Pi buffer again. As the two buffer spectra coincide, the firstly recorded spectrum was used as the buffer spectrum. The buffer spectrum was smoothened using the Savitzky-Golay procedure with convolution width of 25. The other spectra were smoothened according to the same procedure with a convolution width of 15. The smoothened buffer spectrum was then subtracted from each of the other smoothened spectra. The CDNN program was used to estimate the secondary content of the proteins and the resulting estimations are presented in Table IV. The results showed that neither the two amino acid substitutions at position 52 and 53 nor the polypeptide production by chemical synthesis influence the secondary structure content of the chemically synthesized polypeptide. The integrity of the secondary structure content was compared to the recombinantly produced PSI0257 (SEQ ID NO: 271).

TABLE IV

|  | SEQ ID NO: 271 | SEQ ID NO: 267 |
|---|---|---|
| Helix | 63% | 69% |
| Antiparallel | 3% | 2% |
| Parallel | 3% | 3% |
| Beta-Turn | 13% | 12% |
| Rndm. Coil | 13% | 11% |

Example 5

Binding of Modified Compounds and Polypeptides to Human C5

The binding affinity of the C5 binding compounds PSI0242 (SEQ ID NO: 249), PSI0340 (SEQ ID NO: 258), PSI0378 (SEQ ID NO: 261), and PSI0410 (SEQ ID NO: 268) and the C5 binding polypeptide PSI0400 (SEQ ID NO: 267) for human C5 was analyzed using a Biacore T200 instrument (GE Healthcare). Human C5 (A403, Quidel Corporation) was coupled to a CM5 sensor chip (900 RU) using amine coupling chemistry according to the manufacturer's protocol. The coupling was performed by injecting hC5 at a concentration of 7.5 μg/mL in 10 mM Na-acetate buffer pH=5 (GE Healthcare). The reference cell was treated with the same reagents but without injecting human C5. Binding of the C5 binders to immobilized hC5 was studied with the single cycle kinetics method, in which five concentrations of sample, typically 25, 12.5, 6.25, 3.12 and 1.56 nM in HBS-EP buffer (10 mM HEPES pH 7.4, 150 mM NaCl, 3 mM EDTA, 0.005% Surfactant P20, GE Healthcare) were injected one after the other at a flow rate of 30 μL/min at 25° C. in the same cycle without regeneration between injections. Data from the reference cell were subtracted to compensate for bulk refractive index changes. In most cases, an injection of HBS-EP was also included as control so that the sensorgrams were double blanked. The surfaces were regenerated in HBS-EP buffer. Kinetic constants were calculated from the sensorgrams using the Langmuir 1:1 analyte model of the Biacore T200 Evaluation Software version 1.0. The resulting K$_D$ values of the interactions are tabulated in the Table V.

TABLE V

| SEQ ID NO: | Name | K$_D$ (nM) |
|---|---|---|
| 249 | PSI0242 | 1.3 |
| 258 | PSI0340 | 2.5 |
| 261 | PSI0378 | 2.1 |
| 267 | PSI0400 | 0.53 |
| 268 | PSI0410 | 1.3 |

The stability enhancing amino acid substitutions are not detrimental for the ability of the molecules to bind to C5 and thus do not influence their biological activities.

Example 6

Inhibition of Hemolysis

For studies of classical complement pathway function and inhibition thereof by the C5 binding compounds PSI0378 (SEQ ID NO: 261) and PSI0410 (SEQ ID NO: 268), and C5 binding polypeptide PSI0400 (SEQ ID NO: 267), sheep erythrocytes were prepared from fresh sheep whole blood in Alsever's solution (Swedish National Veterinary Institute) and thereafter treated with rabbit anti-sheep erythrocyte antiserum (Sigma) to become antibody sensitized sheep erythrocyte (EA). The whole process was conducted under aseptic conditions. All other reagents were from commercial sources.

The in vitro assay was run in 96-well U-form microtiter plate by consecutive additions of a test protein, a complement serum and EA suspension. The final concentrations of all reagents, in a total reaction volume of 50 μL per well and at pH 7.3-7.4, were: 0.15 mM CaCl 2; 0.5 mM MgCl 2; 3 mM NaN 3; 138 mM NaCl; 0.1% gelatin; 1.8 mM sodium barbital; 3.1 mM barbituric acid; 5 million EA; complement protein C5 serum at suitable dilution, and C5 binding compound or polypeptide at desired concentrations.

The C5 binding compounds and polypeptide were pre-incubated with the above described complement serum for 20 min on ice prior to starting the reaction by the addition of EA suspension. The hemolytic reaction was allowed to proceed at 37° C. during agitation for 45 min and was then optionally ended by addition of 100 μL ice-cold saline containing 0.02% Tween 20. The cells were centrifuged to the bottom and the upper portion, corresponding to 100 μL supernatant, was transferred to a transparent microplate having half-area and flat-bottom wells. The reaction results were analyzed as optical density using a microtiter plate reader at a wavelength of 415 nm.

On all test occasions, a control sample (PSI0242, SEQ ID NO: 249) and vehicle were included in each plate to define values for uninhibited and fully inhibited reactions, respectively. These values were used to calculate the % inhibition of the complement hemolysis at any given sample concentration. The inhibitory potencies (IC 50-values) of tested C5 binding compounds and polypeptide were defined by applying the same assay in the presence of a controlled concentration of human C5 added to C5 depleted serum. For highly potent inhibitors (low nanomolar to sub-nanomolar), a final C5 concentration of the reaction mixture was controlled at 0.1 nM, which was optionally established by using C5 depleted or deficient sera. The results are presented below in Table VI.

TABLE VI

| SEQ ID NO: | Name | Potency (%) | IC 50 (nM) |
|---|---|---|---|
| 249 | PSI0242 | 100 | 0.47 |
| 261 | PSI0378 | 83 | 0.58 |
| 267 | PSI0400 | — | 4 |
| 268 | PSI0410 | 107 | 0.49 |

The results from the hemolysis assay show that the improved C5 binding compounds SEQ ID NO: 261 and 268 are comparable to the reference compound. The C5 binding polypeptide SEQ ID NO: 267 was functional in the assay but since it does not contain an albumin binding domain the results cannot be directly compared to the reference compound.

Example 7

Binding to Human Albumin

For assessment of C5 binding compounds binding affinity for albumin, a human albumin ELISA utilizing recombinant human albumin (coating) and commercially available antibodies (primary and detecting) purchased from Novozymes, Affibody AB and DakoCytomation, respectively, was used. A method standard prepared from PSI0242 (SEQ ID NO:249), comprising a C5 binding polypeptide and an albumin binding domain of streptococcal protein G, was used for quantification of samples. A 96-well microplate was coated with recombinant human albumin. The plate was then washed with phosphate buffered saline containing 0.05 Tween 20 (PBST) and blocked for 1-2 hours with 1% casein in PBS. After a plate wash, the standard, method controls, control sample and test samples are added to the plate. After incubation for 2 hours, unbound material was removed by a wash. A goat Anti-AFFIBODY IgG (Affibody AB, cat no. 20.1000.01.0005) was added to the wells and the plate was incubated for 1.5 hours to allow binding to the bound C5 binding compounds. After a wash, rabbit anti-goat IgG HRP was allowed to bind to the goat antibodies for 1 h. After a final wash, the amount of bound HRP was detected by addition of TMB substrate, which was converted to a blue product by the enzyme. Addition of 1 M hydrochloric acid after 30 minutes stopped the reaction and the color of the well contents changed from blue to yellow. The absorbance at 450 nm was measured photometrically, using the absorbance at 650 nm as a reference wavelength. The color intensity was proportional to the amount of PSI0242 (SEQ ID NO:249) and the sample concentrations were determined from the standard curve.

The C5 binding compounds comprising an albumin binding domain of streptococcal protein G proved capable of binding to human albumin and the data is presented in Table VII below.

TABLE VII

| SEQ ID NO: | Name | % of total protein content |
|---|---|---|
| 249 | PSI0242 | 103 |
| 261 | PSI0378 | 85 |
| 268 | PSI0410 | 150 |

The results from the assay showed that both of the investigated stability improved C5 binding compounds maintain their ability to bind human albumin.

Example 8

3 Month Stability Test of C5 Binding Polypeptides/Compounds

The C5 binding polypeptides/compounds that showed an improved stability compared to PSI0242 in the 2 weeks stability test at 37° C. (Example 2) were subjected to a longer 3 month stability test at 37° C. The setup of the stability test was as described in Example 2 and the evaluation of the stability was made by measuring the main peak of the chromatogram percentage of the total protein content by Reversed Phase HPLC (RPC), the RPC method was performed as described in example 2. The 2 weeks data from example 2 is included in Table VIII below to make the interpretation easier.

TABLE VIII

| SEQ ID NO: | Name | 2 weeks, 37° C. Main peak (% of total protein) | 3 months, 37° C. Main peak (% of total protein) |
|---|---|---|---|
| 253 | PSI0334 | 73 | 16 |
| 261 | PSI0378 | 89 | 59 |
| 262 | PSI0379 | 88 | 58 |
| 263 | PSI0381 | 87 | 46 |
| 264 | PSI0383 | 91 | 59 |
| 268 | PSI0410 | 72 | 16 |
| 269 | PSI0403 | 77 | 35 |
| 270 | PSI0404 | 88 | 46 |

C5 binding compounds with amino acid substitutions in position 52, 53 from ND to SE and a replacement in position 60 from D to E or A (SEQ ID NO: 261, 264, and 262) compared to PSI0242 have a higher proportion of protein in the original form after 3 months at 37° C. than PSI0242 (SEQ ID NO: 249) has after 2 weeks at the same conditions. The other compounds also displayed an increased stability.

Example 9

Stability of Similarly Modified Polypeptides

Previously known polypeptide variants derived from protein Z (Grönwall et al. J Biotechnol 2007, 128:162-183) with binding affinity for other target molecules than C5 were similarly modified in specific positions of the amino acid sequence in order improve stability. Selection and production of the original polypeptide variants with binding affinity for the human epidermal growth factor receptor 2 (HER2), the platelet-derived growth factor receptor beta (PDGF-Rβ), the neonatal Fc receptor (FcRn), and the carbonic anhydrase IX (CAIX) is disclosed in e.g. WO 2009/080810, WO 2009/077175, PCT/EP2014/055299, and WO 2014/096163. The stability improved polypeptide variants were produced by site-directed mutagenesis at selected positions of the amino acid sequence. The stability improving amino acid substitutions in the polypeptide variants Z02891 (SEQ ID NO: 272), targeting HER2; Z15805 (SEQ ID NO: 275), targeting PDGF-Rβ; Z10103 (SEQ ID NO: 278), targeting FcRn; and Z09782 (SEQ ID NO: 281), targeting CAIX, are specified below in Table IX. These stability improved polypeptide variants differ from the C5 binding polypeptides of the present invention for example in that they have a binding motif [BM] with binding affinity for HER2, PDGF-Rβ, FcRn, and CAIX.

All variants were cloned with an N-terminal 6× Histidine-tag (His6) and the achieved constructs encoded polypeptides in the format MGSSHHHHHHLQ-[Z#####] (SEQ ID NO: 299). Mutations were introduced in the plasmids of the polypeptide variants using overlapping oligonucleotide primer pairs encoding the desired amino acid substitutions and by applying established molecular biology techniques. The correct plasmid sequences were verified by DNA sequencing.

*E coli* (strain T7E2) cells (GeneBridge) were transformed with plasmids containing the gene fragments encoding the original and the modified polypeptides. The cells were cultivated at 37° C. in TSB-YE medium supplemented with 50 µg/ml kanamycin and protein expression was subsequently induced by addition of IPTG. Pelleted cells were disrupted using a FASTPREP-24 homogenizer (Nordic Biolabs) and cell debris was removed by centrifugation. Each supernatant containing the polypeptide variant as a His6-tagged protein was purified by immobilized metal ion affinity chromatography (IMAC) using His GRAVITRAP columns (GE Healthcare) according to the manufacturers instructions. Purified polypeptide variants were buffer exchanged to phosphate-buffered saline (PBS; 1.47 mM KH2PO4, 8.1 mM Na2HPO4, 137 mM NaCl, 2.68 mM KCl, pH 7.4) using PD-10 desalting columns (GE Healthcare). The correct identity of each polypeptide was verified by SDS-PAGE and HPLC-MS.

TABLE IX

| SEQ ID NO: | Name | Target | Amino acid substitutions | Original vs modified |
|---|---|---|---|---|
| 272 | Z02891 | HER2 | — | Original |
| 273 | Z17341 | HER2 | N52S, D53E | Modified |
| 274 | Z17342 | HER2 | D36R, D37Q, S39E, N52S, D53E | Modified |
| 275 | Z15805 | PDGF-Rβ | — | Original |
| 276 | Z17343 | PDGF-Rβ | N52S, D53E | Modified |
| 277 | Z17344 | PDGF-Rβ | D36R, D37Q, S39E, N52S, D53E | Modified |
| 278 | Z10103 | FcRn | — | Original |
| 279 | Z17347 | FcRn | N52S, D53E | Modified |
| 280 | Z17348 | FcRn | D36R, D37Q, S39E, N52S, D53E | Modified |
| 281 | Z09782 | CAIX | — | Original |
| 282 | Z17351 | CAIX | N52S, D53E | Modified |
| 283 | Z17352 | CAIX | D36R, D37Q, S39E, N52S, D53E | Modified |
| 284 | Z17355 | CAIX | D53E | Modified |
| 285 | Z17357 | CAIX | D36R, D37Q, S39E, D53E | Modified |
| 286 | Z17359 | CAIX | N52S | Modified |
| 287 | Z17360 | CAIX | D36R, D37Q, S39E, N52S | Modified |

Apart from the substitutions of one of (SEQ ID NO: 284-287) or both of (SEQ ID NO: 273-274, 276-277, 279-280, 282-283) N52 and D53, substitutions were also performed in the positions corresponding to the loop [L2]. Thus, in the polypeptide variants of SEQ ID NO: 274, 277, 280, 283, 285, and 287, [L2] is RQPE.

For carrying out the stability testing, the polypeptide variants, formulated in PBS pH 7.4, were diluted to 1 mg/ml and 200 µl aliquotes were incubated at 37° C. for 2 weeks. Samples collected prior to and after the stability test were analyzed by SDS-PAGE using 10% Bis-Tris NuPAGE gels (Invitrogen) and loading 5 µg protein into each well. Resulting Coomassie blue stained gels are shown in FIG. 6A-D. The stability was assessed by the appearance of new variants after incubation at the elevated temperature and mutated variants were compared to respective original polypeptide.

All polypeptide variants with the modifications as outlined in Table IX showed improved stability compared to the respective original polypeptide in the sense that a second band just above the main band observed for samples of the original polypeptide was not visible in samples of the modified polypeptides with the substitution D53E and/or N52S, see FIG. 6A-D. Polypeptides with the substitutions D53E and/or N52S combined with the substitutions D36R, D37Q and S39E showed similar profiles on the SDS-PAGE gel. The substitution D53E alone or in combination with the substitutions D36R, D37Q and S39E seemed to reduce the amount of the specie with an alternative confirmation observed as a second band on the SDS-PAGE gel, but could not completely prevent the formation of this species.

In addition, the binding capability of the modified polypeptide variants was tested. All polypeptide variants retained their binding affinity for their target after being modified (results not shown).

The results presented above for the polypeptide variants having binding affinity for other target molecules than C5 correspond well with the results presented for the C5 binding polypeptides and compounds of the present invention (see e.g. Example 2 and 4). Thus, the specific amino acid modifications as described herein appear to have a stabilizing effect irrespective of the amino acid sequence of the [BM]. The amino acid modifications or substitutions as described herein are thus considered to improve stability of all the C5 binding polypeptides and compounds as described herein and in WO 2013/126006.

The invention claimed is:

1. A polypeptide capable of binding human complement component 5 (C5), said polypeptide comprising the amino acid sequence

[BM]-[L2]-QSX $X_{24}$ is selected from I, L and V;
$X_{25}$ is selected from A, D, E, H, K, N, Q, R, S and T;
$X_{28}$ is selected from I, L and V; $X_{32}$ is selected from D, E, G, H, N, S and T;
$X_{33}$ is selected from K and S; and $X_{35}$ is selected from A, D, E, H, N, Q, S, T and Y; and
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S,
provided that $X_{53}$ is not D when $X_{52}$ is N; and $X_{54}$ is selected from A and S.

2. The polypeptide according to claim 1, said polypeptide comprising the amino acid sequence (SEQ ID NO: 290)
AEAKYAK-[BM]-[L2]-QSX$_{42}$X$_{43}$LLX$_{46}$EAKKLX$_{2}$X$_{53}$X$_{54}$QAP wherein, independently of each other, [BM], [L2], $X_{42}$, $X_{43}$, $X_{46}$, $X_{52}$, $X_{53}$ and $X_{54}$ are as defined in claim 1.

3. The polypeptide according to claim 1, wherein $X_{52}$ and $X_{53}$ are independently selected from E and S.

4. The polypeptide according to claim 3, wherein (a) $X_{52}$ is S and $X_{53}$ is E, or (b) $X_{52}$ is E and $X_{53}$ is S.

5. The polypeptide according to claim 1, wherein $X_{52}$ is S and $X_{53}$ is D.

6. The polypeptide according to claim 1, wherein $X_{52}$ is N and $X_{53}$ is E.

7. The polypeptide according to claim 1 comprising the amino acid sequence (SEQ ID NO: 294)
AEAKYAKEX$_{9}$X$_{10}$X$_{11}$AX$_{13}$X$_{14}$EIDX$_{18}$LPNLX$_{23}$X$_{24}$X$_{25}$QWX$_{28}$ AFIX$_{32}$X$_{33}$LX$_{35}$-[L2]-QSX$_{42}$X$_{43}$LLX$_{46}$EAKKLX$_{52}$X$_{53}$X$_{54}$QAP;

wherein, independently of each other,
$X_{9}$ is selected from H, Q, S, T and V;
$X_{10}$ is selected from I, L, M and V;
$X_{11}$ is selected from A, D, E, H, K, L, N, Q, R, S, T and Y;
$X_{13}$ is selected from N and W;
$X_{14}$ is selected from A, D, E, H, N, Q, R, S and T;
$X_{18}$ is selected from A, E, G, H, K, L, Q, R, S, T and Y;
$X_{23}$ is selected from N and T;
$X_{24}$ is selected from I, L and V;
$X_{25}$ is selected from A, D, E, H, K, N, Q, R, S and T;
$X_{28}$ is selected from I, L and V;
$X_{32}$ is selected from D, E, G, H, N, S and T;
$X_{33}$ is selected from K and S;
$X_{35}$ is selected from A, D, E, H, N, Q, S, T and Y;
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S, provided that $X_{53}$ is not D when $X_{52}$ is N; and $X_{54}$ is selected from A and S.

8. The polypeptide according to claim 1, wherein at least one of the following conditions is fulfilled:
$X_{9}$ is V,
$X_{10}$ is L,
$X_{11}$ is E,
$X_{13}$ is W,
$X_{14}$ is D, $X_{18}$ is R,
$X_{23}$ is T,
$X_{24}$ is I,
$X_{25}$ is E,
$X_{28}$ is L,
$X_{32}$ is N,
$X_{33}$ is K,
$X_{35}$ is D,
[L2] is DDPS,
$X_{42}$ is S,
$X_{43}$ is E,
$X_{46}$ is S,
$X_{54}$ is S.

9. The polypeptide according to claim 1, wherein [BM] comprises the amino acid sequence selected from the group consisting of positions 1-28 in SEQ ID NOS: 1-248.

10. The polypeptide according to claim 9, wherein [BM] comprises the amino acid sequence shown as positions 1-28 in SEQ ID NO: 1.

11. The polypeptide according to claim 1, selected from a polypeptide comprising the amino sequence shown as SEQ ID NO: 260, SEQ ID NO: 265, SEQ ID NO: 266, or SEQ ID NO: 267.

12. A compound capable of binding C5, said compound comprising:
a) at least one C5 binding polypeptide, said polypeptide comprising the amino acid sequence (SEQ ID NO: 296)
[BM]-[L2]-QSX$_{42}$X$_{43}$LLX$_{46}$EAKKLX$_{52}$X$_{53}$X$_{54}$Q wherein, independently of each other, [BM] is a C5 binding motif comprising the amino acid sequence (SEQ ID NO: 292)
EX$_{9}$X$_{10}$X$_{11}$AX$_{13}$X$_{14}$EIDX$_{18}$LPNLX$_{23}$X$_{24}$X$_{25}$

QWX$_{28}$AFIX$_{32}$X$_{33}$LX$_{35}$;

wherein, independently of each other,
$X_{9}$ is selected from H, Q, S, T and V;
$X_{10}$ is selected from I, L, M and V;
$X_{11}$ is selected from A, D, E, H, K, L, N, Q, R, S, T and Y;
$X_{13}$ is selected from N and W;
$X_{14}$ is selected from A, D, E, H, N, Q, R, S and T;
$X_{18}$ is selected from A, E, G, H, K, L, Q, R, S, T and Y;
$X_{23}$ is selected from N and T;
$X_{24}$ is selected from I, L and V;
$X_{25}$ is selected from A, D, E, H, K, N, Q, R, S and T;
$X_{28}$ is selected from I, L and V;
$X_{32}$ is selected from D, E, G, H, N, S and T;
$X_{33}$ is selected from K and S; and
$X_{35}$ is selected from A, D, E, H, N, Q, S, T and Y;
[L2] is selected from DDPS and RQPE;
$X_{42}$ is selected from A and S;
$X_{43}$ is selected from N and E;
$X_{46}$ is selected from A, S and C;
$X_{52}$ is selected from E, N and S;
$X_{53}$ is selected from D, E and S;
$X_{54}$ is selected from A and S;
b) at least one albumin binding domain of streptococcal protein G; and
c) at least one linking moiety for linking said at least one albumin binding domain to the C or N terminal of said at least one C5 binding polypeptide; wherein the linking moiety comprises KVEGS (SEQ ID NO:297) or KVAGS (SEQ ID NO:298); or wherein said linking moiety is absent.

13. A compound capable of binding C5, said compound comprising:
a) at least one C5 binding polypeptide, said polypeptide comprising the amino acid sequence

[BM]-[L2]-QSX$_{42}$X$_{43}$LLX$_{46}$EAKKLX$_{52}$X$_{53}$X$_{54}$Q     (SEQ ID NO: 296)

wherein, independently of each other,
[BM] is a C5 binding motif comprising the amino acid sequence EX$_9$X$_{10}$X$_{11}$AX$_{13}$X$_{14}$EIDX$_{18}$LPNLX$_{23}$X$_{24}$X$_{25}$     (SEQ ID NO: 292)

QWX$_{28}$AFIX$_{32}$X$_{33}$LX$_{35}$;

wherein, independently of each other,
X$_9$ is selected from H, Q, S, T and V;
X$_{10}$ is selected from I, L, M and V;
X$_{11}$ is selected from A, D, E, H, K, L, N, Q, R, S, T and Y;
X$_{13}$ is selected from N and W;
X$_{14}$ is selected from A, D, E, H, N, Q, R, S and T;
X$_{15}$ is selected from A, E, G, H, K, L, Q, R, S, T and Y;
X$_{23}$ is selected from N and T;
X$_{24}$ is selected from I, L and V;
X$_{25}$ is selected from A, D, E, H, K, N, Q, R, S and T;
X$_{28}$ is selected from I, L and V;
X$_{32}$ is selected from D, E, G, H, N, S and T;
X$_{33}$ is selected from K and S; and
X$_{35}$ is selected from A, D, E, H, N, Q, S, T and Y; and
[L2] is RQPE;
X$_{42}$ is selected from A and S;
X$_{43}$ is selected from N and E;
X$_{46}$ is selected from A, S and C;
X$_{52}$ is selected from E, N and S;
X$_{53}$ is selected from D, E and S;
X$_{54}$ is selected from A and S;
b) at least one albumin binding domain of streptococcal protein G; and
c) optionally, at least one linking moiety for linking said at least one albumin binding domain to the C or N terminal of said at least one C5 binding polypeptide.

14. The polypeptide according to claim 7, wherein at least one of the following conditions is fulfilled:

$X_9$ is V,
$X_{10}$ is L,
$X_{11}$ is E,
$X_{13}$ is W,
$X_{14}$ is D,
$X_{15}$ is R,
$X_{23}$ is T,
$X_{24}$ is I,
$X_{25}$ is E,
$X_{28}$ is L,
$X_{32}$ is N,
$X_{33}$ is K,
$X_{35}$ is D,
[L2] is DDPS,
$X_{42}$ is S,
$X_{43}$ is E,
$X_{46}$ is S,
$X_{54}$ is S.

* * * * *

UNITED STATES PATENT AND TRADEMARK OFFICE
CERTIFICATE OF CORRECTION

PATENT NO. : 9,994,626 B2
APPLICATION NO. : 14/914290
DATED : June 12, 2018
INVENTOR(S) : Joakim Nilsson et al.

Page 1 of 1

It is certified that error appears in the above-identified patent and that said Letters Patent is hereby corrected as shown below:

In the Claims

Claim 1, Column 169, Line 63, please replace the current amino acid sequence ID NO: 289 with the below:

(SEQ ID NO:289)
[*BM*]-[L2]-QSX$_{42}$X$_{43}$LLX$_{46}$EAKKLX$_{52}$X$_{53}$X$_{54}$Q

Claim 2, Column 171, Line 19, please replace the current amino acid sequence ID NO: 290 with the below:

(SEQ ID NO:290)
AEAKYAK-[*BM*]-[L2]-QSX$_{42}$X$_{43}$LLX$_{46}$EAKKLX$_{52}$X$_{53}$X$_{54}$QAP

Claim 13, Column 173, Line 28, please replace with the below:
X$_{18}$ is selected from A, E, G, H, K, L, Q, R, S, T and Y;

Claim 14, Column 174, Line 21, please replace with the below:
X$_{18}$ is R,

Signed and Sealed this
Fifth Day of February, 2019

Andrei Iancu
*Director of the United States Patent and Trademark Office*